United States Patent
Fischer et al.

(10) Patent No.: US 10,654,845 B2
(45) Date of Patent: *May 19, 2020

(54) 2-(HET)ARYL-SUBSTITUTED FUSED BICYCLIC HETEROCYCLE DERIVATIVES AS PESTICIDES

(71) Applicant: BAYER CROPSCIENCE AKTIENGESELLSCHAFT, Monheim Am Rhein (DE)

(72) Inventors: Ruediger Fischer, Pulheim (DE); David Wilcke, Duesseldorf (DE); Kerstin Ilg, Cologne (DE); Daniela Portz, Vettweiss (DE); Ulrich Goergens, Ratingen (DE); Sascha Eilmus, Leichlingen (DE); Olga Malsam, Roesrath (DE); Andreas Turberg, Haan (DE); Sebastian Horstmann, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,871

(22) PCT Filed: Feb. 2, 2016

(86) PCT No.: PCT/EP2016/052105
§ 371 (c)(1),
(2) Date: Aug. 1, 2017

(87) PCT Pub. No.: WO2016/124557
PCT Pub. Date: Aug. 11, 2016

(65) Prior Publication Data
US 2018/0016273 A1    Jan. 18, 2018

(30) Foreign Application Priority Data

Feb. 5, 2015 (EP) .................... 15153948
Jun. 11, 2015 (EP) .................... 15171696

(51) Int. Cl.
C07D 471/04 (2006.01)
A01N 43/90 (2006.01)
A01N 47/40 (2006.01)

(52) U.S. Cl.
CPC ........... *C07D 471/04* (2013.01); *A01N 43/90* (2013.01); *A01N 47/40* (2013.01)

(58) Field of Classification Search
CPC .................... C07D 471/04
See application file for complete search history.

(56) References Cited

U.S. PATENT DOCUMENTS

| | | | |
|---|---|---|---|
| 4,603,139 A | * | 7/1986 | King .................... C07D 471/04 514/337 |
| 10,087,192 B2 | | 10/2018 | Fischer et al. |
| 2013/0150414 A1 | | 6/2013 | Kagabu et al. |
| 2014/0194290 A1 | | 7/2014 | Takahashi et al. |
| 2014/0275025 A1 | | 9/2014 | Anderskewitz et al. |
| 2014/0275026 A1 | | 9/2014 | Wang et al. |
| 2017/0073342 A1 | | 3/2017 | Fischer et al. |
| 2018/0002345 A1 | | 1/2018 | Fischer et al. |

FOREIGN PATENT DOCUMENTS

| | | |
|---|---|---|
| EP | 0693066 A1 | 1/1996 |
| EP | 1671967 A1 | 6/2006 |
| JP | 2014-208695 A | 11/2014 |
| WO | 94/24124 A1 | 10/1994 |
| WO | 2007034277 A1 | 3/2007 |
| WO | 2010/125985 A1 | 11/2010 |
| WO | 2010142426 A1 | 12/2010 |
| WO | 2012/074135 A1 | 6/2012 |
| WO | 2012/086848 A1 | 6/2012 |
| WO | 2013/018928 A1 | 2/2013 |
| WO | 2014/148451 A1 | 9/2014 |

(Continued)

OTHER PUBLICATIONS

Pozharskii et. al. Heterocycles in Life and Society Wiley, 1997, pp. 1-6.*
Johnson, A.W. Invitation to Organic Chemistry 1999 Jones and Bartlett: Mississauga, Canada, p. 24.*
Bpuerstinger et al., "Antiviral 2,5-disubstituted imidazol4,5-clpyridines: Further optimization of anti-hepatitis C virus activity" Bioorganic & Medicinal Chemistry Letters, Bd. 17, Nr. 15, 2007, p. 5111-5114.
Chemical Abstracts Service, Feb. 27, 2017. p. 1. XP002755051.
Chemical Abstracts Service, Jun. 20, 2013. p. 1. XP002755052.

(Continued)

*Primary Examiner* — David K O'Dell
(74) *Attorney, Agent, or Firm* — McBee Moore & Vanik IP, LLC

(57) ABSTRACT

The invention relates to novel compounds of the formula (I)

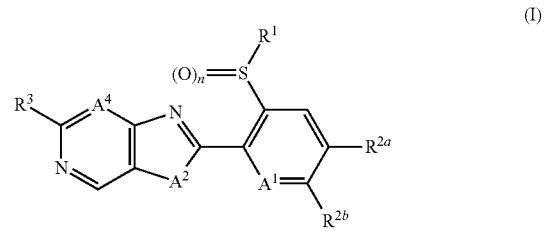

in which the $R^1$, $R^{2a}$, $R^{2b}$, $R^3$, $A^1$, $A^2$, $A^4$ and n have the meanings given above, to their use as acaricides and/or insecticides for controlling animal pests and to processes and intermediates for their preparation.

13 Claims, No Drawings

(56) References Cited

FOREIGN PATENT DOCUMENTS

| WO | 2014148451 A1 | 9/2014 | | |
|---|---|---|---|---|
| WO | 2014206909 A1 | 12/2014 | | |
| WO | 2015/000715 A1 | 1/2015 | | |
| WO | 2015/121136 A1 | 8/2015 | | |
| WO | 2016/002594 A1 | 1/2016 | | |
| WO | WO-2016026848 A1 * | 2/2016 | ........... | C07D 213/79 |
| WO | 2016091731 A1 | 6/2016 | | |
| WO | 2016116338 A1 | 7/2016 | | |
| WO | 2016124563 A1 | 8/2016 | | |
| WO | 2014/142292 A1 | 2/2017 | | |
| WO | WO2015/002211 A1 | 2/2017 | | |

OTHER PUBLICATIONS

Chemical Abstracts Service, Dec. 5, 2012. p. 1. XP002755053.
Chemical Abstracts Service, Dec. 2, 2012. p. 1. XP002755054.
Chemical Abstracts Service, Nov. 23, 2012. p. 1. XP002755055.
Chemical Abstracts Service, Apr. 18, 2011. p. 1. XP002755056.
Chemical Abstracts Service, Apr. 5, 2011. p. 1. XP002755057.
Chemical Abstracts Service, Jan. 7, 2011. p. 1. XP002755058.

* cited by examiner

2-(HET)ARYL-SUBSTITUTED FUSED BICYCLIC HETEROCYCLE DERIVATIVES AS PESTICIDES

CROSS REFERENCE TO RELATED APPLICATIONS

This application is a § 371 National State Application of PCT/EP2016/052105, filed Feb. 2, 2016, which claims priority to European Application Nos. 15153948.3 filed Feb. 5, 2015 and 15171696.6 filed Jun. 11, 2015.

BACKGROUND

Field of the Invention

The present invention relates to novel 2-(het)aryl-substituted fused bicyclic heterocycle derivatives of the formula (I), to the use thereof as acaricides and/or insecticides for controlling animal pests, particularly arthropods and especially insects and arachnids, and to processes and intermediates for preparation thereof.

Description of Related Art 2-(Het)aryl-substituted fused bicyclic heterocycle derivatives having insecticidal properties have already been described in the literature, for example in WO 2010/125985, WO 2012/074135, WO 2012/086848, WO 2013/018928, WO 2014/142292 and WO 2014/148451, and also WO 2015/000715, WO 2015/121136 and WO 2015/002211.

However, the active compounds already known according to the documents cited above have some disadvantages on application, whether because they exhibit only a narrow range of application or because they do not have satisfactory insecticidal or acaricidal activity.

SUMMARY

Novel 2-(het)aryl-substituted fused bicyclic heterocycle derivatives have now been found, and these have advantages over the compounds already known, examples of which are better biological or environmental properties, a wider range of application methods, better insecticidal or acaricidal activity, and also good compatibility with crop plants. The 2-(het)aryl-substituted fused bicyclic heterocycle derivatives can be used in combination with further agents for improving efficacy, especially against insects that are difficult to control.

The present invention therefore provides novel compounds of the formula (I)

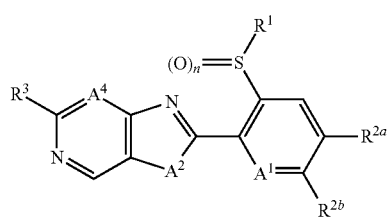

(I)

in which (configuration 1)
$A^1$ represents nitrogen, $=N^+—O^-$ or $=C—R^4$,
$A^2$ represents $—N—R^5$, oxygen or sulphur,
$A^4$ represents nitrogen, $=N^+—O^-$ or $=C—R^4$, $R^1$ represents $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$cycloalkyl, amino, $(C_1-C_6)$-alkylamino, di-$(C_1-C_6)$-alkylamino, $(C_3-C_8)$-cycloalkylamino, $(C_1-C_6)$-alkylcarbonylamino, $(C_1-C_6)$-alkylthio-$(C_1-C_6)$-alkyl, $(C_1-C_6)$-haloalkylthio-$(C_1-C_6)$-alkyl, $(C_1-C_6)$-alkylsulphinyl-$(C_1-C_6)$-alkyl, $(C_1-C_6)$-haloalkylsulphinyl-$(C_1-C_6)$-alkyl, $(C_1-C_6)$-alkylsulphonyl-$(C_1-C_6)$-alkyl, $(C_1-C_6)$-haloalkylsulphonyl-$(C_1-C_6)$-alkyl, $(C_1-C_6)$-alkoxy-$(C_1-C_6)$-alkylthio-$(C_1-C_6)$-alkyl, $(C_1-C_6)$-alkoxy-$(C_1-C_6)$-alkylsulphinyl-$(C_1-C_6)$-alkyl, $(C_1-C_6)$-alkoxy-$(C_1-C_6)$-alkylsulphonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkylsulphonylamino, aminosulphonyl-$(C_1-C_6)$-alkyl, $(C_1-C_6)$-alkylaminosulphonyl-$(C_1-C_6)$-alkyl, di-$(C_1-C_6)$-alkylaminosulphonyl-$(C_1-C_6)$-alkyl,
or represents $(C_1-C_6)$-alkyl, $(C_1-C_6)$-alkoxy, $(C_2-C_6)$-alkenyl, $(C_2-C_6)$-alkynyl, $(C_3-C_8)$-cycloalkyl, each of which is optionally mono- or polysubstituted by identical or different substituents from the group consisting of aryl, hetaryl and heterocyclyl, where aryl, hetaryl and heterocyclyl may each optionally be mono- or polysubstituted by identical or different substituents from the group consisting of halogen, cyano, nitro, hydroxy, amino, carboxy, carbamoyl, aminosulphonyl, $(C_1-C_6)$-alkyl, $(C_3-C_6)$-cycloalkyl, $(C_1-C_6)$-alkoxy, $(C_1-C_6)$-haloalkyl, $(C_1-C_6)$-haloalkoxy, $(C_1-C_6)$-alkylthio, $(C_1-C_6)$-alkylsulphinyl, $(C_1-C_6)$-alkylsulphonyl, $(C_1-C_6)$-alkylsulphimino, $(C_1-C_6)$-alkylsulphimino-$(C_1-C_6)$-alkyl, $(C_1-C_6)$-alkylsulphimino-$(C_2-C_6)$-alkylcarbonyl, $(C_1-C_6)$-alkylsulphoximino, $(C_1-C_6)$-alkylsulphoximino-$(C_1-C_6)$-alkyl, $(C_1-C_6)$-alkylsulphoximino-$(C_2-C_6)$alkylcarbonyl, $(C_1-C_6)$-alkoxycarbonyl, $(C_1-C_6)$-alkylcarbonyl, $(C_3-C_6)$-trialkylsilyl and benzyl, or
$R^1$ represents aryl, hetaryl or heterocyclyl, each of which is optionally mono- or polysubstituted by identical or different substituents from the group consisting of halogen, cyano, nitro, hydroxy, amino, carboxy, carbamoyl, $(C_1-C_6)$-alkyl, $(C_3-C_8)$-cycloalkyl, $(C_1-C_6)$-alkoxy, $(C_1-C_6)$-haloalkyl, $(C_1-C_6)$-haloalkoxy, $(C_1-C_6)$-alkylthio, $(C_1-C_6)$-alkylsulphinyl, $(C_1-C_6)$-alkylsulphonyl, $(C_1-C_6)$-alkylsulphimino, $(C_1-C_6)$-alkylsulphimino-$(C_1-C_6)$-alkyl, $(C_1-C_6)$-alkylsulphimino-$(C_2-C_6)$-alkylcarbonyl, $(C_1-C_6)$-alkylsulphoximino, $(C_1-C_6)$-alkylsulphoximino-$(C_1-C_6)$-alkyl, $(C_1-C_6)$-alkylsulphoximino-$(C_2-C_6)$-alkylcarbonyl, $(C_1-C_6)$-alkoxycarbonyl, $(C_1-C_6)$-alkylcarbonyl, $(C_3-C_6)$-trialkylsilyl, $(=O)$ (only in the case of heterocyclyl) and $(=O)_2$ (only in the case of heterocyclyl),
$R^{2a}$, $R^3$ and $R^4$ independently of one another represent hydrogen, cyano, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$cycloalkyl, halo-$(C_3-C_8)$cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-$ $C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, ($C_1$-$C_6$)-alkoxy-($C_1$-$C_6$)-alkylsulphinyl, ($C_1$-$C_6$)-alkylsulphinyl-($C_1$-$C_6$)-alkyl, ($C_1$-$C_6$)-alkylsulphonyl, ($C_1$-$C_6$)-haloalkylsulphonyl, ($C_1$-$C_6$)-alkoxy-($C_1$-$C_6$)-alkylsulphonyl, ($C_1$-$C_6$)-alkylsulphonyl-($C_1$-$C_6$)-alkyl, ($C_1$-$C_6$)-alkylsulphonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulphonylamino, ($C_1$-$C_6$)-alkylamino, di-($C_1$-$C_6$)-alkylamino, aminosulphonyl, ($C_1$-$C_6$)-alkylaminosulphonyl, di-($C_1$-$C_6$)-alkylaminosulphonyl, ($C_1$-$C_6$)-alkylsulphoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), represent aryl or hetaryl, each of which is optionally mono- or polysubstituted by identical or different substituents, where (in the case of hetaryl) at least one carbonyl group may optionally be present and/or where possible substituents are in each case as follows: cyano, carboxyl, halogen, nitro, acetyl, hydroxy, amino, SCN, tri-($C_1$-$C_6$)-alkylsilyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, ($C_1$-$C_6$)-alkoxy-($C_1$-$C_6$)-alkylsulphinyl, ($C_1$-$C_6$)-alkylsulphinyl-($C_1$-$C_6$)-alkyl, ($C_1$-$C_6$)-alkylsulphonyl, ($C_1$-$C_6$)-haloalkylsulphonyl, ($C_1$-$C_6$)-alkoxy-($C_1$-$C_6$)-alkylsulphonyl, ($C_1$-$C_6$)-alkylsulphonyl-($C_1$-$C_6$)-alkyl, ($C_1$-$C_6$)-alkylsulphonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulphonylamino, ($C_1$-$C_6$)-alkylamino, di-($C_1$-$C_6$)-alkylamino, aminosulphonyl, ($C_1$-$C_6$)-alkylaminosulphonyl, di-($C_1$-$C_6$)-alkylaminosulphonyl, ($C_1$-$C_6$)-alkylsulphoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, $R^{2b}$ represents a group selected from —C(=O)—$R^8$ (Q1), —C(=S)—$R^8$ (Q2), —C(=O)—$NR^{11}R^{12}$ (Q3), —C(=S)—$NR^{11}R^{12}$ (Q4), —S(O)$_m$—$R^{13}$ (Q5), —S=O(=NH)—$R^3$ (Q6), —S=O(=N—CN)—$R^3$ (Q7), —S(=N—CN)—$R^{13}$ (Q8), —S(O)$_2$—$NR^{11}R^{12}$ (Q9), —$NR^{11}R^{12}$ (Q10), —$NR^{11}$—$NR^{11}R^{12}$ (Q11), —$NR^{11}$—C(=O)—$R^8$ (Q12), —$NR^{11}$—C(=S)—$R^8$ (Q13), —$NR^{11}$—S(O)$_2$—$R^{13}$ (Q14), —N($R^{11}$)—O—$R^{13}$ (Q15), —N=S(=O)$_p$—$R^{14}R^{15}$ (Q16) and —O—$R^{13}$ (Q17), where, if $R^{2b}$ represents Q12 and $R^{11}$ represents hydrogen, $R^8$ does not represent ($C_1$-$C_6$)-alkyl, where, if $R^{2b}$ represents Q17, $R^{13}$ does not represent ($C_1$-$C_6$)-alkyl, where, if $R^{2b}$ represents Q5, Q6, Q7, Q8 or Q9, n represents 2, $R^5$ represents ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_6$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)cycloalkyl, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulphinyl-($C_1$-$C_6$)-alkyl, ($C_1$-$C_6$)-haloalkylsulphinyl-($C_1$-$C_6$)-alkyl, ($C_1$-$C_6$)-alkylsulphonyl-($C_1$-$C_6$)-alkyl, ($C_1$-$C_6$)-haloalkylsulphonyl-($C_1$-$C_6$)-alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulphinyl-($C_1$-$C_6$)-alkyl, ($C_1$-$C_6$)-alkoxy-($C_1$-$C_6$)-alkylsulphonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, aminocarbonyl-($C_1$-$C_6$)-alkyl, ($C_1$-$C_6$)-alkylamino-($C_1$-$C_6$)-alkyl, di-($C_1$-$C_6$)-alkylamino-($C_1$-$C_6$)-alkyl or ($C_3$-$C_8$)-cycloalkylamino-($C_1$-$C_6$)-alkyl, $R^8$ represents hydrogen or represents $C_1$-$C_6$-alkyl, $C_2$-$C_6$-alkenyl, $C_2$-$C_6$-alkynyl, $C_1$-$C_4$-alkoxy, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, a phenyl ring and a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O) OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, or $R^8$ represents a phenyl ring or a 3- to 6-membered aromatic, partially saturated or saturated heterocycle, where the heteroatoms are selected from the group consisting of N, S and O, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, or $R^9$, $R^{13}$, $R^{14}$, $R^{15}$ independently of one another represent $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, a phenyl ring or a 3- or 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, $R^9$, $R^{13}$, $R^{14}$, $R^{15}$ independently of one another represent a phenyl ring or a 3- to 6-membered aromatic, partially saturated or saturated heterocycle, where the heteroatoms are selected from the group consisting of N, S and O, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, $R^{11}$, $R^{12}$ independently of one another represent hydrogen or represent $R^9$, m represents 0, 1 or 2, n represents 0, 1 or 2, p represents 0 or 1.

DETAILED DESCRIPTION OF A PREFERRED EMBODIMENT

It has additionally been found that the compounds of the formula (I) have very good efficacy as pesticides, preferably as insecticides and/or acaricides, and additionally generally have very good plant compatibility, in particular with respect to crop plants.

A general definition of the compounds of the invention is provided by the formula (I). Preferred substituents or ranges of the radicals given in the formulae mentioned above and below are illustrated hereinafter:

Configuration 1-1:

$R^1$, $R^{2a}$, $R^{2b}$, $R^3$, $R^4$, $R^5$, $R^8$, $R^{11}$, $R^{12}$, $A^1$, $A^2$, $A^4$, m, n and p have the meanings given for Configuration 1 and $R^9$, $R^{13}$, $R^{14}$, $R^{15}$ independently of one another represent $C_1$-$C_6$-alkylsulphonyl or represent $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, a phenyl ring or a 3- or 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, $R^9$, $R^{13}$, $R^{14}$, $R^{15}$ independently of one another represent a phenyl ring or a 3- to 6-membered aromatic, partially saturated or saturated heterocycle, where the heteroatoms are selected from the group consisting of N, S and O, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, Configuration 1-2:

$A^1$ represents nitrogen, $=N^+$—$O^-$ or $=C$—$R^4$, $A^2$ represents —N—$R^5$, oxygen or sulphur, $A^4$ represents nitrogen, $=N^+$—$O^-$ or $=C$—$R^4$, $R^1$ represents ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_6$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_8$)-cycloalkyl-($C_3$-$C_8$)-cycloalkyl, ($C_1$-$C_6$)-alkyl($C_3$-$C_8$)-cycloalkyl, halo-($C_3$-$C_8$)cycloalkyl, amino, ($C_1$-$C_6$)-alkylamino, di-($C_1$-$C_6$)-alkylamino, ($C_3$-$C_8$)-cycloalkylamino, ($C_1$-$C_6$)-alkylcarbonylamino, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulphinyl-($C_1$-$C_6$)-alkyl, ($C_1$-$C_6$)-haloalkylsulphinyl-($C_1$-$C_6$)-alkyl, ($C_1$-$C_6$)-alkylsulphonyl-($C_1$-$C_6$)-alkyl, ($C_1$-$C_6$)-haloalkylsulphonyl-($C_1$-$C_6$)-alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulphinyl-($C_1$-$C_6$)-alkyl, ($C_1$-$C_6$)-alkoxy-($C_1$-$C_6$)-alkylsulphonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkylsulphonylamino, aminosulphonyl-($C_1$-$C_6$)-alkyl, ($C_1$-$C_6$)-alkylaminosulphonyl-($C_1$-$C_6$)-alkyl, di-($C_1$-$C_6$)-alkylaminosulphonyl-($C_1$-$C_6$)-alkyl, or represents ($C_1$-$C_6$)-alkyl, ($C_1$-$C_6$)-alkoxy, ($C_2$-$C_6$)-alkenyl, ($C_2$-$C_6$)-alkynyl, ($C_3$-$C_8$)-cycloalkyl, each of which is optionally mono- or polysubstituted by identical or different substituents from the group consisting of aryl, hetaryl and heterocyclyl, where aryl, hetaryl and heterocyclyl may each optionally be mono- or polysubstituted by identical or different substituents from the group consisting of halogen, cyano, nitro, hydroxy, amino, carboxy, carbamoyl, aminosulphonyl, ($C_1$-$C_6$)-alkyl, ($C_3$-$C_6$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, ($C_1$-$C_6$)-alkylsulphimino, ($C_1$-$C_6$)-alkylsulphimino-($C_1$-$C_6$)-alkyl, ($C_1$-$C_6$)-alkylsulphimino-($C_2$-$C_6$)-alkylcarbonyl, ($C_1$-$C_6$)-alkylsulphoximino, ($C_1$-$C_6$)-alkylsulphoximino-($C_1$-$C_6$)-alkyl, ($C_1$-$C_6$)-alkylsulphoximino-($C_2$-$C_6$)alkylcarbonyl, ($C_1$-$C_6$)-alkoxycarbonyl, ($C_1$-$C_6$)-alkylcarbonyl, ($C_3$-$C_6$)-trialkylsilyl and benzyl, or $R^1$ represents aryl, hetaryl or heterocyclyl, each of which is optionally mono- or polysubstituted by identical or different substituents from the group consisting of halogen, cyano, nitro, hydroxy, amino, carboxy, carbamoyl, ($C_1$-$C_6$)-alkyl, ($C_3$-$C_8$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, ($C_1$-$C_6$)-alkylsulphimino, ($C_1$-$C_6$)-alkylsulphimino-($C_1$-$C_6$)-alkyl, ($C_1$-$C_6$)-alkylsulphimino-($C_2$-$C_6$)-alkylcarbonyl, ($C_1$-$C_6$)-alkylsulphoximino, ($C_1$-$C_6$)-alkylsulphoximino-($C_1$-$C_6$)-alkyl, ($C_1$-$C_6$)-alkylsulphoximino-($C_2$-$C_6$)-alkylcarbonyl, ($C_1$-$C_6$)-alkoxycarbonyl, ($C_1$-$C_6$)-alkylcarbonyl, ($C_3$-$C_6$)-trialkylsilyl, (=O) (only in the case of heterocyclyl) and (=O)$_2$ (only in the case of heterocyclyl), $R^{2a}$, $R^3$ and $R^4$ independently of one another represent hydrogen, cyano, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)cycloalkyl, halo-($C_3$-$C_8$)cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkinyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, ($C_1$-$C_6$)-alkoxy-($C_1$-$C_6$)-alkylsulphinyl, ($C_1$-$C_6$)-alkylsulphinyl-($C_1$-$C_6$)-alkyl, ($C_1$-$C_6$)-alkylsulphonyl, ($C_1$-$C_6$)-haloalkylsulphonyl, ($C_1$-$C_6$)-alkoxy-($C_1$-$C_6$)-alkylsulphonyl, ($C_1$-$C_6$)-alkylsulphonyl-($C_1$-$C_6$)-alkyl, ($C_1$-$C_6$)-alkylsulphonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulphonylamino, ($C_1$-$C_6$)-alkylamino, di-($C_1$-$C_6$)-alkylamino, aminosulphonyl, ($C_1$-$C_6$)-alkylaminosulphonyl, di-($C_1$-$C_6$)-alkylaminosulphonyl, ($C_1$-$C_6$)-alkylsulphoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), represent aryl or hetaryl, each of which is optionally mono- or polysubstituted by identical or different substituents, where (in the case of hetaryl) at least one carbonyl group may optionally be present and/or where possible substituents are in each case as follows: cyano, carboxyl, halogen, nitro, acetyl, hydroxy, amino, SCN, tri-($C_1$-$C_6$)-alkylsilyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)- alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, ($C_1$-$C_6$)-alkoxy-($C_1$-$C_6$)-alkylsulphinyl, ($C_1$-$C_6$)-alkylsulphinyl-($C_1$-$C_6$)-alkyl, ($C_1$-$C_6$)-alkylsulphonyl, ($C_1$-$C_6$)-haloalkylsulphonyl, ($C_1$-$C_6$)-alkoxy-($C_1$-$C_6$)-alkylsulphonyl, ($C_1$-$C_6$)-alkylsulphonyl-($C_1$-$C_6$)-alkyl, ($C_1$-$C_6$)-alkylsulphonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulphonylamino, ($C_1$-$C_6$)-alkylamino, di-($C_1$-$C_6$)-alkylamino, aminosulphonyl, ($C_1$-$C_6$)-alkylaminosulphonyl, di-($C_1$-$C_6$)-alkylaminosulphonyl, ($C_1$-$C_6$)-alkylsulphoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, $R^{2b}$ represents a group selected from —C(=O)—$R^8$ (Q1), —C(=S)—$R^8$ (Q2), —C(=O)—$NR^{11}R^{12}$ (Q3), —C(=S)—$NR^{11}R^{12}$ (Q4), —S(O)$_m$—$R^{13}$ (Q5), —S=O(=NH)—$R^3$ (Q6), —S=O(=N—CN)—$R^3$ (Q7), —S(=N—CN)—$R^{13}$ (Q8), —S(O)$_2$—$NR^{11}R^{12}$ (Q9), —$NR^{11}R^{12}$ (Q10), —$NR^{11}$—$NR^{11}R^{12}$ (Q11), —$NR^{11}$—C(=O)—$R^8$ (Q12), —$NR^{11}$—C(=S)—$R^8$ (Q13), —$NR^{11}$—S(O)$_2$—$R^{13}$ (Q14), —N($R^{11}$)—O—$R^{13}$ (Q15), —N=S(=O)$_p$—$R^{14}R^{15}$ (Q16), —O—$R^{13}$ (Q17) or —$C^{11}$=$CR^8R^{12}$ (Q18), where, if $R^{2b}$ represents Q12 and $R^{11}$ represents hydrogen, $R^8$ does not represent ($C_1$-$C_6$)-alkyl, where, if $R^{2b}$ represents Q17, $R^{13}$ does not represent ($C_1$-$C_6$)-alkyl, where, if $R^{2b}$ represents Q5, Q6, Q7, Q8 or Q9, n represents 2, $R^5$ represents ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_6$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)cycloalkyl, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulphinyl-($C_1$-$C_6$)-alkyl, ($C_1$-$C_6$)-haloalkylsulphinyl-($C_1$-$C_6$)-alkyl, ($C_1$-$C_6$)-alkylsulphonyl-($C_1$-$C_6$)-alkyl, ($C_1$-$C_6$)-haloalkylsulphonyl-($C_1$-$C_6$)-alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulphinyl-($C_1$-$C_6$)-alkyl, ($C_1$-$C_6$)-alkoxy-($C_1$-$C_6$)-alkylsulphonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, aminocarbonyl-($C_1$-$C_6$)-alkyl, ($C_1$-$C_6$)-alkylamino-($C_1$-$C_6$)-alkyl, di-($C_1$-$C_6$)-alkylamino-($C_1$-$C_6$)-alkyl or ($C_3$-$C_8$)-cycloalkylamino-($C_1$-$C_6$)-alkyl, $R^8$ represents hydrogen or represents $C_1$-$C_6$-alkyl, $C_2$-$C_6$-alkenyl, $C_2$-$C_6$-alkynyl, $C_1$-$C_4$-alkoxy, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, a phenyl ring and a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O) OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, or $R^8$ represents a phenyl ring, a benzyl ring or a 3- to 6-membered aromatic, partially saturated or saturated heterocycle, where the heteroatoms are selected from the group consisting of N, S and O, where the phenyl ring or the benzyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, (C=O) OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, or $R^9$, $R^{13}$, $R^{14}$, $R^{15}$ independently of one another represent $C_1$-$C_6$-alkylsulphonyl or represent $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, each of which is optionally mono- or polysubstituted by identical or different substituents, where the substituents independently of one another may be selected from the group consisting of halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, a phenyl ring or a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, $R^9$, $R^{13}$, $R^{14}$, $R^{15}$ independently of one another represent a phenyl ring, a benzyl ring or a 3- to 6-membered aromatic, partially saturated or saturated heterocycle, where the heteroatoms are selected from the group consisting of N, S and O, where the phenyl ring, the benzyl ring or heterocycle may in each case optionally be mono- or polysubstituted by identical or different substituents, and where the substituents independently of one another may be selected from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)-alkylsilyl, ($C_1$-$C_4$-alkyl)($C_1$-$C_4$-alkoxy)imino, $R^{11}$, $R^{12}$ independently of one another represent hydrogen or represent $R^9$, m represents 0, 1 or 2, n represents 0, 1 or 2, p represents 0 or 1.

Configuration 2:

$A^1$ preferably represents nitrogen, =$N^+$—$O^-$ or =C—$R^4$, $A^2$ preferably represents —N—$R^5$, oxygen or sulphur, $A^4$ preferably represents =$N^+$—$O^-$ or =C—$R^4$, $R^1$ preferably represents ($C_1$-$C_4$)-alkyl, ($C_1$-$C_4$)-hydroxyalkyl, ($C_1$-$C_4$)-haloalkyl, ($C_1$-$C_4$)-cyanoalkyl, ($C_1$-$C_4$)-alkoxy-($C_1$-$C_4$)-alkyl, ($C_1$-$C_4$)-haloalkoxy-($C_1$-$C_4$)-alkyl, ($C_2$-$C_4$)-alkenyl, ($C_2$-$C_4$)-alkenyloxy-($C_1$-$C_4$)-alkyl, ($C_2$-$C_4$)-haloalkenyloxy-($C_1$-$C_4$)-alkyl, ($C_2$-$C_4$)-haloalkenyl, ($C_2$-$C_4$)-cyanoalkenyl, ($C_2$-$C_4$)-alkynyl, ($C_2$-$C_4$)-alkynyloxy-($C_1$-$C_4$)-alkyl, ($C_2$-$C_4$)-haloalkynyloxy-($C_1$-$C_4$)-alkyl, ($C_2$-$C_4$)-haloalkynyl, ($C_2$-$C_4$)-cyanoalkynyl, ($C_3$-$C_6$)-cycloalkyl, ($C_3$-$C_6$)-cycloalkyl-($C_3$-$C_6$)-cycloalkyl, ($C_1$-$C_4$)-alkyl($C_3$-$C_6$)-cycloalkyl, halo-($C_3$-$C_6$)-cycloalkyl, ($C_1$-$C_4$)-alkylamino, di-($C_1$-$C_4$)-alkylamino, ($C_3$-$C_6$)-cycloalkylamino, ($C_1$-$C_4$)-alkylcarbonylamino, ($C_1$-$C_4$)-alkylthio-($C_1$-$C_4$)-alkyl, ($C_1$-$C_4$)-haloalkylthio-($C_1$-$C_4$)-alkyl, ($C_1$-$C_4$)-alkylsulphinyl-($C_1$-$C_4$)-alkyl, ($C_1$-$C_4$)-haloalkylsulphinyl-($C_1$-$C_4$)-alkyl, ($C_1$-$C_4$)-alkylsulphonyl-($C_1$-$C_4$)-alkyl, ($C_1$-$C_4$)-alkylcarbonyl-($C_1$-$C_4$)-alkyl, ($C_1$-$C_4$)-haloalkylcarbonyl-($C_1$-$C_4$)-alkyl, ($C_1$-$C_4$)-alkylsulphonylamino, or represents ($C_1$-$C_4$)-alkyl, ($C_1$-$C_4$)-alkoxy, ($C_2$-$C_4$)-alkenyl, ($C_2$-$C_4$)-alkynyl, ($C_3$-$C_6$)cycloalkyl, each of which is optionally mono- or disubstituted by identical or different substituents from the group consisting of aryl, hetaryl and heterocyclyl, where aryl, hetaryl and heterocyclyl may in each case optionally be mono- or disubstituted by identical or different substituents from the group consisting of halogen, cyano, carbamoyl, aminosulphonyl, ($C_1$-$C_4$)-alkyl, ($C_3$-$C_4$)-cycloalkyl, ($C_1$-$C_4$)-alkoxy, ($C_1$-$C_4$)-haloalkyl, ($C_1$-$C_4$)-haloalkoxy, ($C_1$-$C_4$)-alkylthio, ($C_1$-$C_4$)-alkylsulphinyl, ($C_1$-$C_4$)-alkylsulphonyl, ($C_1$-$C_4$)-alkylsulphimino, or $R^1$ preferably represents aryl, hetaryl or heterocyclyl, each of which is optionally mono- or disubstituted by identical or different substituents from the group consisting of halogen, cyano, carbamoyl, ($C_1$-$C_4$)-alkyl, ($C_3$-$C_6$)-cycloalkyl, ($C_1$-$C_4$)-alkoxy, ($C_1$-$C_4$)-haloalkyl, ($C_1$-$C_4$)-haloalkoxy, ($C_1$-$C_4$)-alkylthio, ($C_1$-$C_4$)-alkylsulphinyl, ($C_1$-$C_4$)-alkylsulphonyl, ($C_1$-$C_4$)-alkylsulphimino, ($C_1$-$C_4$)-alkylsulphoximino, ($C_1$-$C_4$)-alkylcarbonyl, ($C_3$-$C_4$)-trialkylsilyl, (=O) (only in the case of heterocyclyl) and (=O)$_2$ (only in the case of heterocyclyl), $R^{2a}$, $R^3$ and $R^4$ independently of one another preferably represent hydrogen, cyano, halogen, nitro, acetyl, hydroxy, amino, SCN, tri-($C_1$-$C_4$)-alkylsilyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_4$)-alkyl, ($C_2$-$C_4$)-alkenyl, ($C_2$-$C_4$)-haloalkenyl, ($C_2$-$C_4$)-cyanoalkenyl, ($C_2$-$C_4$)-alkynyl, ($C_2$-$C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxy-($C_1$-$C_4$)-alkoxy, ($C_1$-$C_4$)-alkylhydroxyimino, ($C_1$-$C_4$)-alkoxyimino, ($C_1$-$C_4$)-alkyl-($C_1$-$C_4$)-alkoxyimino, ($C_1$-$C_4$)-haloalkyl-($C_1$-$C_4$)-alkoxyimino, ($C_1$-$C_4$)-alkylthio, ($C_1$-$C_4$)-haloalkylthio, ($C_1$-$C_4$)-alkylthio-($C_1$-$C_4$)-alkyl, ($C_1$-$C_4$)-alkylsulphinyl, ($C_1$-$C_4$)-haloalkylsulphinyl, ($C_1$-$C_4$)-alkylsulphinyl-($C_1$-$C_4$)-alkyl, ($C_1$-$C_4$)-alkylsulphonyl, ($C_1$-$C_4$)-haloalkylsulphonyl, ($C_1$-$C_4$)-alkylsulphonyl-($C_1$-$C_4$)-alkyl, ($C_1$-$C_4$)-alkylsulphonyloxy, ($C_1$-$C_4$)-alkylcarbonyl, ($C_1$-$C_4$)-haloalkylcarbonyl, aminocarbonyl, aminothiocarbonyl, ($C_1$-$C_4$)-alkylaminocarbonyl, di-($C_1$-$C_4$)-alkylaminocarbonyl, ($C_1$-$C_4$)-alkylsulphonylamino, ($C_1$-$C_4$)-alkylamino, di-($C_1$-$C_4$)-alkylamino, aminosulphonyl, ($C_1$-$C_4$)-alkylaminosulphonyl, di-($C_1$-$C_4$)-alkylaminosulphonyl, aminothiocarbonyl, NHCO—($C_1$-$C_4$)-alkyl (($C_1$-$C_4$)-alkylcarbonylamino), or represent phenyl or hetaryl, each of which is optionally mono- or disubstituted by identical or different substituents, where (in the case of hetaryl) at least one carbonyl group may optionally be present and/or where possible substituents are in each case as follows: cyano, halogen, nitro, acetyl, amino, ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_4$)-alkyl, ($C_2$-$C_4$)-alkenyl, ($C_2$-$C_4$)-haloalkenyl, ($C_2$-$C_4$)-cyanoalkenyl, ($C_2$-$C_4$)-alkynyl, ($C_2$-$C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxy-($C_1$-$C_4$)-alkoxy, ($C_1$-$C_4$)-alkylhydroxyimino, ($C_1$-$C_4$)-alkoxyimino, ($C_1$-$C_4$)-alkyl-($C_1$-$C_4$)-alkoxyimino, ($C_1$-$C_4$)-haloalkyl-($C_1$-$C_4$)-alkoxyimino, ($C_1$-$C_4$)-alkylthio, ($C_1$-$C_4$)-haloalkylthio, ($C_1$-$C_4$)-alkylthio-($C_1$-$C_4$)-alkyl, ($C_1$-$C_4$)-alkylsulphinyl, ($C_1$-$C_4$)-haloalkylsulphinyl, ($C_1$-$C_4$)-alkylsulphinyl-($C_1$-$C_4$)-alkyl, ($C_1$-$C_4$)-alkylsulphonyl, ($C_1$-$C_4$)-haloalkylsulphonyl, ($C_1$-$C_4$)-alkylsulphonyl-($C_1$-$C_4$)-alkyl, ($C_1$-$C_4$)-alkylsulphonyloxy, ($C_1$-$C_4$)-alkylcarbonyl, ($C_1$-$C_4$)-haloalkylcarbonyl, aminocarbonyl, ($C_1$-$C_4$)-alkylaminocarbonyl, di-($C_1$-$C_4$)-alkylaminocarbonyl, ($C_1$-$C_4$)-alkylsulphonylamino, ($C_1$-$C_4$)-alkylamino, di-($C_1$-$C_4$)-alkylamino, aminosulphonyl, $(C_1-C_4)$-alkylaminosulphonyl, di-$(C_1-C_4)$-alkylaminosulphonyl, $R^{2b}$ preferably represents a group selected from Q1, Q2, Q3, Q4, Q5, Q6, Q7, Q8, Q9, Q10, Q11, Q12, Q13, Q14, Q15, Q16, Q17 and Q18, where, if $R^{2b}$ represents Q12 and $R^{11}$ represents hydrogen, $R^8$ does not represent $(C_1-C_4)$-alkyl, where, if $R^{2b}$ represents Q17, $R^{13}$ does not represent $(C_1-C_4)$-alkyl, where, if $R^{2b}$ represents Q5, Q6, Q7, Q8 or Q9, n represents 2, $R^5$ preferably represents $(C_1-C_4)$-alkyl, $(C_1-C_4)$-haloalkyl, $(C_1-C_4)$-cyanoalkyl, $(C_1-C_4)$-hydroxyalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_4)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylthio-$(C_1-C_4)$-alkyl, $(C_1-C_4)$-haloalkylthio-$(C_1-C_4)$-alkyl, $(C_1-C_4)$-alkylsulphinyl-$(C_1-C_4)$-alkyl, $(C_1-C_4)$-haloalkylsulphinyl-$(C_1-C_4)$-alkyl, $(C_1-C_4)$-alkylsulphonyl-$(C_1-C_4)$-alkyl, $(C_1-C_4)$-haloalkylsulphonyl-$(C_1-C_4)$-alkyl, $(C_1-C_4)$-alkoxy-$(C_1-C_4)$-alkylthio-$(C_1-C_4)$-alkyl or $(C_1-C_4)$-alkylcarbonyl-$(C_1-C_4)$-alkyl, $R^8$ preferably represents hydrogen, represents $C_1-C_4$-alkyl, $C_3-C_6$-cycloalkyl or $C_1-C_4$-alkoxy, each of which is optionally mono- or polysubstituted by identical or different substituents, where the substituents independently of one another may be selected from the group consisting of halogen, cyano, a phenyl ring and a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen, cyano, $NO_2$, $C_1-C_4$-alkoxy and $C_1-C_4$-haloalkoxy, $R^8$ preferably represents a phenyl ring or a 3- to 6-membered aromatic, partially saturated or saturated heterocycle, where the heteroatoms are selected from the group consisting of N, S and O, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen and cyano, $R^9$, $R^{13}$, $R^{14}$, $R^{15}$ independently of one another preferably represent $C_1-C_4$-alkyl or $C_3-C_6$-cycloalkyl, each of which is optionally mono- or polysubstituted by identical or different substituents, where the substituents independently of one another may be selected from the group consisting of halogen, cyano, a phenyl ring and a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen, cyano, $NO_2$, $C_1-C_4$-alkoxy and $C_1-C_4$-haloalkoxy, $R^9$, $R^{13}$, $R^{14}$, $R^{15}$ independently of one another preferably represent a phenyl ring or a 3- to 6-membered aromatic, partially saturated or saturated heterocycle, where the heteroatoms are selected from the group consisting of N, S and O, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen and cyano, $R^{11}$, $R^{12}$ independently of one another preferably represent hydrogen or represent $R^9$, m preferably represents 0, 1 or 2, n preferably represents 0, 1 or 2, p preferably represents 0 or 1.

Configuration 2-1:

$R^1$, $R^{2a}$, $R^{2b}$, $R^3$, $R^4$, $R^5$, $R^{11}$, $R^{12}$, $A^1$, $A^2$, $A^4$, m, n and p have the meanings given for Configuration 1 and $R^8$ preferably represents hydrogen, represents $C_1-C_4$-alkyl, $C_3-C_6$-cycloalkyl, $C_3-C_6$-cycloalkyl-$C_1-C_4$-alkyl or $C_1-C_4$-alkoxy, each of which is optionally mono- or polysubstituted by identical or different substituents, where the substituents independently of one another may be selected from the group consisting of halogen, cyano, a phenyl ring and a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen, cyano, $NO_2$, $C_1-C_4$-alkoxy and $C_1-C_4$-haloalkoxy, $R^8$ preferably represents a phenyl ring or a 3- to 6-membered aromatic, partially saturated or saturated heterocycle, where the heteroatoms are selected from the group consisting of N, S and O, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen and cyano, $R^9$, $R^{13}$, $R^{14}$, $R^5$ independently of one another preferably represent $C_1-C_4$-alkylsulphonyl, represent $C_1-C_4$-alkyl or $C_3-C_6$-cycloalkyl, each of which is optionally mono- or polysubstituted by identical or different substituents, where the substituents independently of one another may be selected from the group consisting of halogen, cyano, a phenyl ring and a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen, cyano, $NO_2$, $C_1-C_4$-alkoxy and $C_1-C_4$-haloalkoxy, $R^9$, $R^{13}$, $R^{14}$, $R^5$ independently of one another preferably represent a phenyl ring or a 3- to 6-membered aromatic, partially saturated or saturated heterocycle, where the heteroatoms are selected from the group consisting of N, S and O, where the phenyl ring or heterocycle may in each case optionally be mono- or polysubstituted by identical or different substituents, and where the substituents independently of one another may be selected from the group consisting of $C_1-C_4$-alkyl, $C_1-C_4$-haloalkyl, halogen and cyano.

Configuration 2-2:

$A^1$ preferably represents nitrogen, $=N^+-O^-$ or $=C-R^4$, $A^2$ preferably represents $-N-R^5$, oxygen or sulphur, $A^4$ is preferably nitrogen, $=N^+-O^-$ or $=C-R^4$, $R^1$ preferably represents $(C_1-C_4)$-alkyl, $(C_1-C_4)$-hydroxyalkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-haloalkoxy-$(C_1-C_4)$-alkyl, ($C_2$-$C_4$)-alkenyl, ($C_2$-$C_4$)-alkenyloxy-($C_1$-$C_4$)-alkyl, ($C_2$-$C_4$)-haloalkenyloxy-($C_1$-$C_4$)-alkyl, ($C_2$-$C_4$)-haloalkenyl, ($C_2$-$C_4$)-cyanoalkenyl, ($C_2$-$C_4$)-alkynyl, ($C_2$-$C_4$)-alkynyloxy-($C_1$-$C_4$)-alkyl, ($C_2$-$C_4$)-haloalkynyloxy-($C_1$-$C_4$)-alkyl, ($C_2$-$C_4$)-haloalkynyl, ($C_2$-$C_4$)-cyanoalkynyl, ($C_3$-$C_6$)-cycloalkyl, ($C_3$-$C_6$)-cycloalkyl-($C_3$-$C_6$)-cycloalkyl, ($C_1$-$C_4$)-alkyl($C_3$-$C_6$)-cycloalkyl, halo-($C_3$-$C_6$)-cycloalkyl, ($C_1$-$C_4$)-alkylamino, di-($C_1$-$C_4$)-alkylamino, ($C_3$-$C_6$)-cycloalkylamino, ($C_1$-$C_4$)-alkylcarbonylamino, ($C_1$-$C_4$)-alkylthio-($C_1$-$C_4$)-alkyl, ($C_1$-$C_4$)-haloalkylthio-($C_1$-$C_4$)-alkyl, ($C_1$-$C_4$)-alkylsulphinyl-($C_1$-$C_4$)-alkyl, ($C_1$-$C_4$)-haloalkylsulphinyl-($C_1$-$C_4$)-alkyl, ($C_1$-$C_4$)-alkylsulphonyl-($C_1$-$C_4$)-alkyl, ($C_1$-$C_4$)-alkylcarbonyl-($C_1$-$C_4$)-alkyl, ($C_1$-$C_4$)-haloalkylcarbonyl-($C_1$-$C_4$)-alkyl, ($C_1$-$C_4$)-alkylsulphonylamino, or represents ($C_1$-$C_4$)-alkyl, ($C_1$-$C_4$)-alkoxy, ($C_2$-$C_4$)-alkenyl, ($C_2$-$C_4$)-alkynyl, ($C_3$-$C_6$) cycloalkyl, each of which is optionally mono- or disubstituted by identical or different substituents from the group consisting of aryl, hetaryl and heterocyclyl, where aryl, hetaryl and heterocyclyl may in each case optionally be mono- or disubstituted by identical or different substituents from the group consisting of halogen, cyano, carbamoyl, aminosulphonyl, ($C_1$-$C_4$)-alkyl, ($C_3$-$C_4$)-cycloalkyl, ($C_1$-$C_4$)-alkoxy, ($C_1$-$C_4$)-haloalkyl, ($C_1$-$C_4$)-haloalkoxy, ($C_1$-$C_4$)-alkylthio, ($C_1$-$C_4$)-alkylsulphinyl, ($C_1$-$C_4$)-alkylsulphonyl, ($C_1$-$C_4$)-alkylsulphimino, or $R^1$ preferably represents aryl, hetaryl or heterocyclyl, each of which is optionally mono- or disubstituted by identical or different substituents from the group consisting of halogen, cyano, carbamoyl, ($C_1$-$C_4$)-alkyl, ($C_3$-$C_6$)-cycloalkyl, ($C_1$-$C_4$)-alkoxy, ($C_1$-$C_4$)-haloalkyl, ($C_1$-$C_4$)-haloalkoxy, ($C_1$-$C_4$)-alkylthio, ($C_1$-$C_4$)-alkylsulphinyl, ($C_1$-$C_4$)-alkylsulphonyl, ($C_1$-$C_4$)-alkylsulphimino, ($C_1$-$C_4$)-alkylsulphoximino, ($C_1$-$C_4$)-alkylcarbonyl, ($C_3$-$C_4$)-trialkylsilyl, (=O) (only in the case of heterocyclyl) and (=O)$_2$ (only in the case of heterocyclyl), $R^{2a}$, $R^3$ and $R^4$ independently of one another preferably represent hydrogen, cyano, halogen, nitro, acetyl, hydroxy, amino, SCN, tri-($C_1$-$C_4$)-alkylsilyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_4$)-alkyl, ($C_2$-$C_4$)-alkenyl, ($C_2$-$C_4$)-haloalkenyl, ($C_2$-$C_4$)-cyanoalkenyl, ($C_2$-$C_4$)-alkynyl, ($C_2$-$C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxy-($C_1$-$C_4$)-alkoxy, ($C_1$-$C_4$)-alkylhydroxyimino, ($C_1$-$C_4$)-alkoxyimino, ($C_1$-$C_4$)-alkyl-($C_1$-$C_4$)-alkoxyimino, ($C_1$-$C_4$)-haloalkyl-($C_1$-$C_4$)-alkoxyimino, ($C_1$-$C_4$)-alkylthio, ($C_1$-$C_4$)-haloalkylthio, ($C_1$-$C_4$)-alkylthio-($C_1$-$C_4$)-alkyl, ($C_1$-$C_4$)-alkylsulphinyl, ($C_1$-$C_4$)-haloalkylsulphinyl, ($C_1$-$C_4$)-alkylsulphinyl-($C_1$-$C_4$)-alkyl, ($C_1$-$C_4$)-alkylsulphonyl, ($C_1$-$C_4$)-haloalkylsulphonyl, ($C_1$-$C_4$)-alkylsulphonyl-($C_1$-$C_4$)-alkyl, ($C_1$-$C_4$)-alkylsulphonyloxy, ($C_1$-$C_4$)-alkylcarbonyl, ($C_1$-$C_4$)-haloalkylcarbonyl, aminocarbonyl, aminothiocarbonyl, ($C_1$-$C_4$)-alkylaminocarbonyl, di-($C_1$-$C_4$)-alkylaminocarbonyl, ($C_1$-$C_4$)-alkylsulphonylamino, ($C_1$-$C_4$)-alkylamino, di-($C_1$-$C_4$)-alkylamino, aminosulphonyl, ($C_1$-$C_4$)-alkylaminosulphonyl, di-($C_1$-$C_4$)-alkylaminosulphonyl, aminothiocarbonyl, NHCO—($C_1$-$C_4$)-alkyl (($C_1$-$C_4$)-alkylcarbonylamino), or represent phenyl or hetaryl, each of which is optionally mono- or disubstituted by identical or different substituents, where (in the case of hetaryl) at least one carbonyl group may optionally be present and/or where possible substituents are in each case as follows: cyano, halogen, nitro, acetyl, amino, ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_4$)-alkyl, ($C_2$-$C_4$)-alkenyl, ($C_2$-$C_4$)-haloalkenyl, ($C_2$-$C_4$)-cyanoalkenyl, ($C_2$-$C_4$)-alkynyl, ($C_2$-$C_4$)-haloalkynyl, ($C_2$-$C_4$)-cyanoalkynyl, ($C_1$-$C_4$)-alkoxy, ($C_1$-$C_4$)-haloalkoxy, ($C_1$-$C_4$)-cyanoalkoxy, ($C_1$-$C_4$)-alkoxy-($C_1$-$C_4$)-alkoxy, ($C_1$-$C_4$)-alkylhydroxyimino, ($C_1$-$C_4$)-alkoxyimino, ($C_1$-$C_4$)-alkyl-($C_1$-$C_4$)-alkoxyimino, ($C_1$-$C_4$)-haloalkyl-($C_1$-$C_4$)-alkoxyimino, ($C_1$-$C_4$)-alkylthio, ($C_1$-$C_4$)-haloalkylthio, ($C_1$-$C_4$)-alkylthio-($C_1$-$C_4$)-alkyl, ($C_1$-$C_4$)-alkylsulphinyl, ($C_1$-$C_4$)-haloalkylsulphinyl, ($C_1$-$C_4$)-alkylsulphinyl-($C_1$-$C_4$)-alkyl, ($C_1$-$C_4$)-alkylsulphonyl, ($C_1$-$C_4$)-haloalkylsulphonyl, ($C_1$-$C_4$)-alkylsulphonyl-($C_1$-$C_4$)-alkyl, ($C_1$-$C_4$)-alkylsulphonyloxy, ($C_1$-$C_4$)-alkylcarbonyl, ($C_1$-$C_4$)-haloalkylcarbonyl, aminocarbonyl, ($C_1$-$C_4$)-alkylaminocarbonyl, di-($C_1$-$C_4$)-alkylaminocarbonyl, ($C_1$-$C_4$)-alkylsulphonylamino, ($C_1$-$C_4$)-alkylamino, di-($C_1$-$C_4$)-alkylamino, aminosulphonyl, ($C_1$-$C_4$)-alkylaminosulphonyl, di-($C_1$-$C_4$)-alkylaminosulphonyl, $R^{2b}$ preferably represents a group selected from Q1, Q2, Q3, Q4, Q5, Q6, Q8, Q9, Q10, Q11, Q12, Q13, Q14, Q15, Q16, Q17 and Q18, where, if $R^{2b}$ represents Q12 and $R^{11}$ represents hydrogen, $R^8$ does not represent ($C_1$-$C_4$)-alkyl, where, if $R^{2b}$ represents Q17, $R^{13}$ does not represent ($C_1$-$C_4$)-alkyl, where, if $R^{2b}$ represents Q5, Q6, Q8 or Q9, n represents 2, $R^5$ preferably represents ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_4$)-alkyl, ($C_1$-$C_4$)-haloalkoxy-($C_1$-$C_4$)-alkyl, ($C_2$-$C_4$)-alkenyl, ($C_2$-$C_4$)-alkenyloxy-($C_1$-$C_4$)-alkyl, ($C_2$-$C_4$)-haloalkenyloxy-($C_1$-$C_4$)-alkyl, ($C_2$-$C_4$)-haloalkenyl, ($C_2$-$C_4$)-cyanoalkenyl, ($C_2$-$C_4$)-alkynyl, ($C_2$-$C_4$)-alkynyloxy-($C_1$-$C_4$)-alkyl, ($C_2$-$C_4$)-haloalkynyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkylthio-($C_1$-$C_4$)-alkyl, ($C_1$-$C_4$)-haloalkylthio-($C_1$-$C_4$)-alkyl, ($C_1$-$C_4$)-alkylsulphinyl-($C_1$-$C_4$)-alkyl, ($C_1$-$C_4$)-haloalkylsulphinyl-($C_1$-$C_4$)-alkyl, ($C_1$-$C_4$)-alkylsulphonyl-($C_1$-$C_4$)-alkyl, ($C_1$-$C_4$)-haloalkylsulphonyl-($C_1$-$C_4$)-alkyl, ($C_1$-$C_4$)-alkoxy-($C_1$-$C_4$)-alkylthio-($C_1$-$C_4$)-alkyl or ($C_1$-$C_4$)-alkylcarbonyl-($C_1$-$C_4$)-alkyl, $R^8$ preferably represents hydrogen, represents $C_1$-$C_4$-alkyl, ($C_1$-$C_6$)-alkylthio-($C_1$-$C_6$)-alkyl, ($C_1$-$C_4$)-alkylsulphinyl-($C_1$-$C_4$)-alkyl, ($C_1$-$C_4$)-alkylsulphonyl-($C_1$-$C_4$)-alkyl, $C_3$-$C_6$-cycloalkyl, $C_3$-$C_6$-cycloalkyl-$C_1$-$C_4$-alkyl, $C_1$-$C_4$-alkoxy or $C_1$-$C_4$-alkoxy-$C_1$-$C_4$-alkyl, each of which is optionally mono- or polysubstituted by identical or different substituents, where the substituents independently of one another may be selected from halogen, cyano, a phenyl ring or a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1$-$C_4$-alkyl, $C_1$-$C_4$-haloalkyl, halogen, cyano, NO$_2$, $C_1$-$C_4$-alkoxy and $C_1$-$C_4$-haloalkoxy, $R^8$ preferably represents a phenyl ring, a benzyl ring or a 3- to 6-membered aromatic, partially saturated or saturated heterocycle, where the heteroatoms are selected from the group consisting of N, S and O, where the phenyl ring or the benzyl ring or heterocycle may in each case optionally be mono- or polysubstituted by identical or different substituents, and where the substituents independently of one another may be selected from the group consisting of $C_1$-$C_4$-alkyl, $C_1$-$C_4$-haloalkyl, halogen and cyano, $R^9$, $R^{13}$, $R^{14}$, $R^{15}$ independently of one another preferably represent $C_1$-$C_4$-alkylsulphonyl, represent $C_1$-$C_4$-alkyl or $C_3$-$C_6$-cycloalkyl, each of which is optionally mono- or polysubstituted by identical or different substituents, where the substituents independently of one another may be selected from the group consisting of halogen, cyano, a phenyl ring and a 3- to 6-membered aromatic, partially saturated or saturated heterocycle, where the phenyl ring or heterocycle may in each case optionally be mono- or polysubstituted by identical or different substituents, and where the substituents independently of one another may be selected from the group consisting of $C_1$-$C_4$-alkyl, $C_1$-$C_4$-haloalkyl, halogen, cyano, $NO_2$, $C_1$-$C_4$-alkoxy and $C_1$-$C_4$-haloalkoxy, $R^9$, $R^{13}$, $R^{14}$, $R^{15}$ independently of one another preferably represent a phenyl ring, a benzyl ring or a 3- to 6-membered aromatic, partially saturated or saturated heterocycle, where the heteroatoms are selected from the group consisting of N, S and O, where the phenyl ring or the benzyl ring or heterocycle may in each case optionally be mono- or polysubstituted by identical or different substituents, and where the substituents independently of one another may be selected from the group consisting of $C_1$-$C_4$-alkyl, $C_1$-$C_4$-haloalkyl, halogen and cyano, $R^{11}$, $R^{12}$ independently of one another preferably represent hydrogen or represent $R^9$, m preferably represents 0, 1 or 2,
n preferably represents 0, 1 or 2,
p preferably represents 0 or 1.

Configuration 3:
$A^1$ particularly preferably represents nitrogen or =C—$R^4$,
$A^2$ particularly preferably represents —N—$R^5$ or oxygen,
$A^4$ particularly preferably represents =C—H,
$R^1$ particularly preferably represents $(C_1$-$C_4)$-alkyl, $(C_1$-$C_4)$-hydroxyalkyl, $(C_1$-$C_4)$-haloalkyl, $(C_2$-$C_4)$-alkenyl, $(C_2$-$C_4)$-haloalkenyl, $(C_2$-$C_4)$-alkynyl, $(C_2$-$C_4)$-haloalkynyl, $(C_3$-$C_6)$-cycloalkyl, $(C_1$-$C_4)$-alkylthio-$(C_1$-$C_4)$-alkyl, $(C_1$-$C_4)$-alkylsulphinyl-$(C_1$-$C_4)$-alkyl or $(C_1$-$C_4)$-alkylsulphonyl-$(C_1$-$C_4)$-alkyl, $R^{2a}$ particularly preferably represents hydrogen, cyano, aminocarbonyl, halogen, $(C_1$-$C_4)$-alkyl, $(C_1$-$C_4)$-haloalkyl, $(C_1$-$C_4)$-haloalkoxy, $(C_1$-$C_4)$-alkylthio, $(C_1$-$C_4)$-alkylsulphinyl, $(C_1$-$C_4)$-alkylsulphonyl, $(C_1$-$C_4)$-haloalkylthio, $(C_1$-$C_4)$-haloalkylsulphinyl or $(C_1$-$C_4)$-haloalkylsulphonyl, $R^{2b}$ particularly preferably represents a group selected from Q1, Q2, Q3, Q4, Q5, Q6, Q7, Q8, Q9, Q10, Q11, Q12, Q13, Q14, Q15, Q16 and Q17,
  where, if $R^{2b}$ represents Q12 and $R^{11}$ represents hydrogen, $R^8$ does not represent methyl, ethyl, isopropyl, tert-butyl,
  where, if $R^{2b}$ represents Q17, $R^{13}$ does not represent methyl, ethyl, isopropyl, tert-butyl,
  where, if $R^{2b}$ represents Q5, Q6, Q7, Q8 or Q9, n represents 2, $R^3$ particularly preferably represents hydrogen, halogen, $(C_1$-$C_4)$-alkyl, $(C_1$-$C_4)$-haloalkyl, $(C_1$-$C_4)$-haloalkoxy, $(C_1$-$C_4)$-alkylthio, $(C_1$-$C_4)$-alkylsulphinyl, $(C_1$-$C_4)$-alkylsulphonyl, $(C_1$-$C_4)$-haloalkylthio, $(C_1$-$C_4)$-haloalkylsulphinyl or $(C_1$-$C_4)$-haloalkylsulphonyl, $R^4$ particularly preferably represents hydrogen, halogen, cyano or $(C_1$-$C_4)$-alkyl, $R^5$ particularly preferably represents $(C_1$-$C_4)$-alkyl or $(C_1$-$C_4)$-alkoxy-$(C_1$-$C_4)$-alkyl, $R^8$ particularly preferably represents hydrogen, represents methyl, ethyl, isopropyl, tert-butyl, methoxy or ethoxy, each of which is optionally monosubstituted by halogen, cyano, phenyl or pyridyl, where phenyl and pyridyl may each be mono- or disubstituted by identical or different substituents from the group consisting of trifluoromethyl, cyano, fluorine, chlorine, bromine and trifluoromethoxy, or $R^8$ particularly preferably represents phenyl, pyridyl or a 3- to 6-membered saturated heterocycle comprising 1-2 heteroatoms from the group consisting of N, S and O, where phenyl, pyridyl and the heterocycle may each optionally be mono- or disubstituted by identical or different substituents, and where the substituents independently of one another may be selected from $C_1$-$C_4$-alkyl, $C_1$-$C_4$-haloalkyl, halogen and cyano, $R^9$, $R^{13}$, $R^{14}$, $R^{15}$ independently of one another particularly preferably represent methyl, ethyl, isopropyl or tert-butyl, each of which may optionally be monosubstituted by halogen, cyano, phenyl or pyridyl, where phenyl and pyridyl may each optionally be mono- or disubstituted by identical or different substituents from the group consisting of trifluoromethyl, cyano, fluorine, chlorine and trifluoromethoxy, or $R^9$, $R^{13}$, $R^{14}$, $R^5$ independently of one another particularly preferably represent phenyl, pyridyl or a 3- to 6-membered saturated heterocycle comprising 1-2 heteroatoms from the group consisting of N, S and O, where phenyl, pyridyl and the heterocycle may each be mono- or disubstituted by identical or different substituents, and where the substituents independently of one another may be selected from the group consisting of $C_1$-$C_4$-alkyl, $C_1$-$C_4$-haloalkyl, halogen and cyano, $R^1$, $R^{12}$ independently of one another particularly preferably represent hydrogen or represent $R^9$, m particularly preferably represents 0, 1 or 2,
n particularly preferably represents 0, 1 or 2,
p particularly preferably represents 0 and 1.

Configuration 3-1:
$A^1$ particularly preferably represents nitrogen or =C—$R^4$,
$A^2$ particularly preferably represents —N—$R^5$ or oxygen,
$A^4$ particularly preferably represents =C—H,
$R^1$ particularly preferably represents $(C_1$-$C_4)$-alkyl, $(C_1$-$C_4)$-hydroxyalkyl, $(C_1$-$C_4)$-haloalkyl, $(C_2$-$C_4)$-alkenyl, $(C_2$-$C_4)$-haloalkenyl, $(C_2$-$C_4)$-alkynyl, $(C_2$-$C_4)$-haloalkynyl, $(C_3$-$C_6)$-cycloalkyl, $(C_1$-$C_4)$-alkylthio-$(C_1$-$C_4)$-alkyl, $(C_1$-$C_4)$-alkylsulphinyl-$(C_1$-$C_4)$-alkyl, $(C_1$-$C_4)$-alkylsulphonyl-$(C_1$-$C_4)$-alkyl or benzyl, $R^{2a}$ particularly preferably represents hydrogen, cyano, aminocarbonyl, halogen, $(C_1$-$C_4)$-alkyl, $(C_1$-$C_4)$-haloalkyl, $(C_1$-$C_4)$-haloalkoxy, $(C_1$-$C_4)$-alkylthio, $(C_1$-$C_4)$-alkylsulphinyl, $(C_1$-$C_4)$-alkylsulphonyl, $(C_1$-$C_4)$-haloalkylthio, $(C_1$-$C_4)$-haloalkylsulphinyl or $(C_1$-$C_4)$-haloalkylsulphonyl, $R^{2b}$ particularly preferably represents a group selected from Q1, Q2, Q3, Q4, Q5, Q6, Q7, Q8, Q9, Q10, Q11, Q12, Q13, Q14, Q15, Q16 and Q17,
  where, if $R^{2b}$ represents Q12 and $R^{11}$ represents hydrogen, $R^8$ does not represent $(C_1$-$C_4)$-alkyl,
  where, if $R^{2b}$ represents Q17, $R^3$ does not represent $(C_1$-$C_4)$-alkyl,
  where, if $R^{2b}$ represents Q5, Q6, Q7, Q8 or Q9, n represents 2, $R^3$ particularly preferably represents hydrogen, halogen, $(C_1$-$C_4)$-alkyl, $(C_1$-$C_4)$-haloalkyl, $(C_1$-$C_4)$-haloalkoxy, $(C_1-C_4)$-alkylthio, $(C_1-C_4)$-alkylsulphinyl, $(C_1-C_4)$-alkylsulphonyl, $(C_1-C_4)$-haloalkylthio, $(C_1-C_4)$-haloalkylsulphinyl or $(C_1-C_4)$-haloalkylsulphonyl, $R^4$ particularly preferably represents hydrogen, halogen, cyano or $(C_1-C_4)$-alkyl, $R^5$ particularly preferably represents $(C_1-C_4)$-alkyl or $(C_1-C_4)$-alkoxy-$(C_1-C_4)$-alkyl, $R^8$ particularly preferably represents hydrogen, represents $(C_1-C_4)$-alkyl, $(C_1-C_4)$-haloalkyl, $(C_1-C_4)$-alkoxyalkyl, $(C_3-C_6)$-cycloalkyl, $(C_3-C_6)$-cycloalkyl-$(C_1-C_4)$-alkyl or $(C_1-C_4)$-alkoxy, or $R^8$ particularly preferably represents phenyl, pyridyl or pyrazolyl, where phenyl, pyridyl and pyrazolyl may in each case optionally be mono- or disubstituted by identical or different substituents, and where the substituents independently of one another may be selected from the group consisting of $C_1-C_4$-alkyl, $C_1-C_4$-haloalkyl, halogen and cyano, $R^9$, $R^{13}$, $R^{14}$, $R^{15}$ independently of one another particularly preferably represent $(C_1-C_4)$-alkyl, benzyl or $(C_1-C_4)$-alkylsulphonyl, or $R^9$, $R^{13}$, $R^{14}$, $R^5$ independently of one another particularly preferably represent phenyl, pyridyl or pyrazolyl, where phenyl, pyridyl and pyrazolyl may in each case optionally be mono- or disubstituted by identical or different substituents, and where the substituents independently of one another may be selected from the group consisting of $C_1-C_4$-alkyl, $C_1-C_4$-haloalkyl, halogen and cyano, $R^{11}$, $R^{12}$ independently of one another particularly preferably represent hydrogen or represent $R^9$, m particularly preferably represents 0, 1 or 2, n particularly preferably represents 0, 1 or 2, p particularly preferably represents 0 and 1.

Configuration 3-2:

$A^1$ particularly preferably represents nitrogen or =C—$R^4$, $A^2$ particularly preferably represents —N—$R^5$ or oxygen, $A^4$ particularly preferably represents =C—H, $R^1$ particularly preferably represents $(C_1-C_4)$-alkyl, $(C_1-C_4)$-hydroxyalkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_1-C_4)$-alkylthio-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$-alkyl or benzyl, $R^{2a}$ particularly preferably represents hydrogen, cyano, aminocarbonyl, halogen, $(C_1-C_4)$-alkyl, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-haloalkylthio, $(C_1-C_4)$-haloalkylsulphinyl or $(C_1-C_4)$-haloalkylsulphonyl, $R^{2b}$ particularly preferably represents a group selected from Q1, Q3, Q4, Q5, Q6, Q8, Q9, Q10, Q11, Q12, Q13, Q14, Q17 and Q18, where, if $R^{2b}$ represents Q12 and $R^{11}$ represents hydrogen, $R^8$ does not represent $(C_1-C_4)$-alkyl, where, if $R^{2b}$ represents Q17, $R^3$ does not represent $(C_1-C_4)$-alkyl, where, if $R^{2b}$ represents Q5, Q6, Q8 or Q9, n represents 2, $R^3$ particularly preferably represents hydrogen, halogen, $(C_1-C_4)$-alkyl, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-haloalkylthio, $(C_1-C_4)$-haloalkylsulphinyl or $(C_1-C_4)$-haloalkylsulphonyl, $R^4$ particularly preferably represents hydrogen, halogen, cyano or $(C_1-C_4)$-alkyl, $R^5$ particularly preferably represents $(C_1-C_4)$-alkyl or $(C_1-C_4)$-alkoxy-$(C_1-C_4)$-alkyl, $R^8$ particularly preferably represents hydrogen, represents $(C_1-C_4)$-alkyl, $(C_1-C_4)$-haloalkyl, $(C_1-C_4)$-alkoxy-$(C_1-C_4)$-alkyl, $(C_1-C_6)$-alkylthio-$(C_1-C_6)$-alkyl, $(C_1-C_4)$-alkylsulphinyl-$(C_1-C_4)$-alkyl, $(C_1-C_4)$-alkylsulphonyl-$(C_1-C_4)$-alkyl, $(C_3-C_6)$-cycloalkyl, $(C_3-C_6)$-cycloalkyl-$(C_1-C_4)$-alkyl or $(C_1-C_4)$-alkoxy, or $R^8$ particularly preferably represents phenyl, benzyl, pyridyl, thiazolyl or pyrazolyl, where phenyl, benzyl, pyridyl, thiazolyl and pyrazolyl may in each case optionally be mono- or disubstituted by identical or different substituents, and where the substituents independently of one another may be selected from the group consisting of $C_1-C_4$-alkyl, $C_1-C_4$-haloalkyl, halogen and cyano, $R^9$, $R^{13}$, $R^{14}$, $R^{15}$ independently of one another particularly preferably represent $(C_1-C_4)$-alkyl, $(C_1-C_4)$-haloalkyl, acetyl, $(C_3-C_6)$-cycloalkyl, benzyl or $(C_1-C_4)$-alkylsulphonyl, or $R^9$, $R^{13}$, $R^{14}$, $R^{15}$ independently of one another particularly preferably represent phenyl, pyridyl or pyrazolyl, where phenyl, pyridyl and pyrazolyl may in each case optionally be mono- or disubstituted by identical or different substituents, and where the substituents independently of one another may be selected from the group consisting of $C_1-C_4$-alkyl, $C_1-C_4$-haloalkyl, halogen and cyano, $R^{11}$, $R^{12}$ independently of one another particularly preferably represent hydrogen or represent $R^9$, m particularly preferably represents 0, 1 or 2, n particularly preferably represents 0, 1 or 2.

Configuration 4:

$A^1$ very particularly preferably represents nitrogen or =C—$R^4$, $A^2$ very particularly preferably represents —N—$R^5$ or oxygen, $A^4$ very particularly preferably represents =C—H, $R^1$ very particularly preferably represents methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^{2a}$ very particularly preferably represents hydrogen, cyano, aminocarbonyl ($CONH_2$), fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl, trifluoromethylsulphinyl, fluorine or chlorine, $R^{2b}$ very particularly preferably represents a group selected from Q1, Q2, Q3, Q4, Q5, Q6, Q7, Q8, Q9, Q10, Q11, Q12, Q13, Q14, Q15, Q16 and Q17, where, if $R^{2b}$ represents Q12 and $R^{11}$ represents hydrogen, $R^8$ does not represent methyl, ethyl, isopropyl, tert-butyl, where, if $R^{2b}$ represents Q17, $R^{13}$ does not represent methyl, ethyl, isopropyl, tert-butyl, where, if $R^{2b}$ represents Q5, Q6, Q7, Q8 or Q9, n represents 2, $R^3$ very particularly preferably represents fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl or trifluoromethylsulphinyl, $R^4$ very particularly preferably represents hydrogen, fluorine, chlorine, bromine or cyano, $R^5$ very particularly preferably represents methyl, ethyl, isopropyl, methoxymethyl or methoxyethyl, $R^8$ very particularly preferably represents hydrogen, represents methyl, ethyl, isopropyl, tert-butyl, methoxy or ethoxy, each of which is optionally monosubstituted by halogen, cyano, phenyl or pyridyl, where phenyl and pyridyl may each be mono- or disubstituted by identical or different substituents from the group consisting of trifluoromethyl, cyano, fluorine, chlorine, bromine and trifluoromethoxy, or $R^8$ very particularly preferably represents phenyl, pyridyl or a 3- to 6-membered saturated heterocycle comprising 1-2 heteroatoms from the group consisting of N, S and O, where phenyl, pyridyl and the heterocycle may each optionally be mono- or disubstituted by identical or different substituents, and where the substituents independently of one another may be selected from $C_1$-$C_4$-alkyl, $C_1$-$C_4$-haloalkyl, halogen and cyano, $R^9$, $R^{13}$, $R^{14}$, $R^{15}$ independently of one another very particularly preferably represent methyl, ethyl, isopropyl or tert-butyl, each of which may optionally be monosubstituted by halogen, cyano, phenyl or pyridyl, where phenyl and pyridyl may each optionally be mono- or disubstituted by identical or different substituents from the group consisting of trifluoromethyl, cyano, fluorine, chlorine and trifluoromethoxy, or $R^9$, $R^{13}$, $R^{14}$, $R^{15}$ independently of one another very particularly preferably represent phenyl, pyridyl or a 3- to 6-membered saturated heterocycle comprising 1-2 heteroatoms from the group consisting of N, S and O, where phenyl, pyridyl and the heterocycle may each be mono- or disubstituted by identical or different substituents, and where the substituents independently of one another may be selected from the group consisting of $C_1$-$C_4$-alkyl, $C_1$-$C_4$-haloalkyl, halogen and cyano, $R^{11}$, $R^{12}$ independently of one another very particularly preferably represent hydrogen or represent $R^9$, m very particularly preferably represents 0, 1 or 2,
n very particularly preferably represents 0, 1 or 2,
p very particularly preferably represents 0 and 1.

Configuration 4-1:
$A^1$ very particularly preferably represents nitrogen or =C—$R^4$,
$A^2$ very particularly preferably represents —N—$R^5$ or oxygen,
$A^4$ very particularly preferably represents =C—H,
$R^1$ very particularly preferably represents methyl, ethyl, n-propyl, isopropyl, cyclopropyl, n-butyl, isobutyl, tert-butyl, cyclobutyl, benzyl, fluoromethyl, difluoromethyl, trifluoromethyl, fluoroethyl, difluoroethyl, trifluoroethyl, tetrafluoroethyl or pentafluoroethyl,
$R^{2a}$ very particularly preferably represents hydrogen, cyano, aminocarbonyl ($CONH_2$), fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl, trifluoromethylsulphinyl, fluorine or chlorine,
$R^{2b}$ very particularly preferably represents a group selected from Q1, Q2, Q3, Q4, Q5, Q6, Q7, Q8, Q9, Q10, Q11, Q12, Q13, Q14, Q15, Q16 and Q17,
where, if $R^{2b}$ represents Q12 and $R^{11}$ represents hydrogen, $R^8$ does not represent methyl, ethyl, isopropyl, tert-butyl,
where, if $R^{2b}$ represents Q17, $R^{13}$ does not represent methyl, ethyl, isopropyl, tert-butyl,
where, if $R^{2b}$ represents Q5, Q6, Q7, Q8 or Q9, n represents 2, $R^3$ very particularly preferably represents fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl or trifluoromethylsulphinyl,
$R^4$ very particularly preferably represents hydrogen, fluorine, chlorine, bromine or cyano,
$R^5$ very particularly preferably represents methyl, ethyl, isopropyl, methoxymethyl or methoxyethyl,
$R^8$ very particularly preferably represents hydrogen, represents methyl, ethyl, isopropyl, tert-butyl, trifluoromethyl, difluoromethyl, tetrafluoroethyl, pentafluoroethyl, methoxymethyl, cyclopropyl, cyclopropylmethyl, methoxy or ethoxy, or
$R^8$ very particularly preferably represents phenyl, pyridyl or pyrazolyl, where phenyl, pyridyl and pyrazolyl may in each case optionally be mono- or disubstituted by identical or different substituents, and where the substituents independently of one another may be selected from the group consisting of $C_1$-$C_4$-alkyl, $C_1$-$C_4$-haloalkyl, halogen and cyano,
$R^9$, $R^{13}$, $R^{14}$, $R^{15}$ independently of one another very particularly preferably represent methyl, ethyl, isopropyl, tert-butyl, benzyl or methylsulphonyl, or
$R^9$, $R^{13}$, $R^{14}$, $R^{15}$ independently of one another very particularly preferably represent phenyl, pyridyl or pyrazolyl, where phenyl, pyridyl and pyrazolyl may in each case optionally be mono- or disubstituted by identical or different substituents, and where the substituents independently of one another may be selected from the group consisting of $C_1$-$C_4$-alkyl, $C_1$-$C_4$-haloalkyl, halogen and cyano,
$R^{11}$, $R^{12}$ independently of one another very particularly preferably represent hydrogen or represent $R^9$,
m very particularly preferably represents 0, 1 or 2,
n very particularly preferably represents 0, 1 or 2,
p very particularly preferably represents 0 and 1.

Configuration 4-2:
$A^1$ very particularly preferably represents nitrogen or =C—$R^4$,
$A^2$ very particularly preferably represents —N—$R^5$ or oxygen,
$A^4$ very particularly preferably represents =C—H,
$R^1$ very particularly preferably represents methyl, ethyl, n-propyl, isopropyl, cyclopropyl, n-butyl, isobutyl, tert-butyl, cyclobutyl, benzyl, fluoromethyl, difluoromethyl, trifluoromethyl, fluoroethyl, difluoroethyl, trifluoroethyl, tetrafluoroethyl or pentafluoroethyl,
$R^{2a}$ very particularly preferably represents hydrogen, cyano, aminocarbonyl ($CONH_2$), fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl, trifluoromethylsulphinyl, fluorine or chlorine,
$R^{2b}$ very particularly preferably represents a group selected from
Q1, where $R^8$ represents methyl, ethyl, n-propyl, isopropyl, n-butyl, isobutyl, methoxy or ethoxy,
Q3, where $R^{11}$ represents hydrogen, methyl, ethyl, n-propyl, isopropyl or cyclopropyl and $R^{12}$ represents hydrogen, methyl, ethyl, n-propyl, isopropyl, n-butyl, isobutyl, tert-butyl, cyclopropyl or acetyl,
Q4, where $R^{11}$ represents hydrogen, methyl, ethyl, n-propyl, isopropyl or cyclopropyl and $R^{12}$ represents hydrogen, methyl, ethyl, n-propyl, isopropyl, n-butyl, isobutyl, tert-butyl, cyclopropyl or acetyl,
Q5, where m represents 0, 1 or 2 and $R^{13}$ represents methyl, ethyl, n-propyl, isopropyl, n-butyl, isobutyl, tert-butyl, phenyl or benzyl,
Q6, where $R^{13}$ represents methyl, ethyl, n-propyl, isopropyl, n-butyl, isobutyl or tert-butyl,
Q8, where $R^{13}$ represents methyl, ethyl, n-propyl, isopropyl, n-butyl, isobutyl or tert-butyl,
Q9, where $R^{11}$ represents hydrogen, methyl, ethyl, n-propyl, isopropyl or cyclopropyl and $R^{12}$ represents hydrogen, methyl, ethyl, n-propyl, isopropyl, n-butyl, isobutyl, tert-butyl, cyclopropyl or acetyl,
Q10, where $R^{11}$ represents hydrogen, methyl, ethyl, n-propyl, isopropyl, n-butyl, isobutyl, tert-butyl or cyclopropyl and $R^{12}$ represents hydrogen, methyl, ethyl, n-propyl, isopropyl, n-butyl, isobutyl, tert-butyl or cyclopropyl,
Q11, where $R^{11}$ represents hydrogen, methyl, ethyl, n-propyl, isopropyl, cyclopropyl or acetyl and $R^{12}$ represents hydrogen, methyl, ethyl, n-propyl, isopropyl, n-butyl, isobutyl, tert-butyl, cyclopropyl, phenyl or acetyl,
Q12, where $R^{11}$ represents hydrogen, methyl, ethyl, n-propyl, isopropyl or cyclopropyl and $R^8$ represents methyl, ethyl, n-propyl, isopropyl (only if $R^{11}$ does not represent hydrogen may $R^8$ represent methyl, ethyl, n-propyl or isopropyl), fluoromethyl, difluoromethyl, trifluoromethyl, fluoroethyl, difluoroethyl, trifluoroethyl, tetrafluoroethyl, pentafluoroethyl, $CH_2OCH_3$, $CH_2SCH_3$, $CH_2OC_2H_5$, $CH_2SOCH_3$, $CH_2SO_2CH_3$, $CH(CH_3)CH_2SCH_3$, $CH(CH_3)CH_2SOCH_3$, $CH(CH_3)CH_2SO_2CH_3$, $C_2H_4OC_2H_5$, $C_2H_4SC_2H_5$, $C_2H_4OC_2H_5$, $C_2H_4SOC_2H_5$, $C_2H_4SO_2C_2H_5$, $CH(CH_3)CH_2SC_2H_5$, $CH(CH_3)CH_2SOC_2H_5$, $CH(CH_3)CH_2SO_2C_2H_5$, cyclopropyl, cyclopropylmethyl, represents phenyl, benzyl, pyridyl or thiazolyl, each of which may optionally be monosubstituted by fluorine, chlorine or bromine,
Q13, where $R^8$ represents methyl, ethyl, n-propyl, isopropyl, n-butyl, isobutyl or tert-butyl and $R^{11}$ represents hydrogen, methyl, ethyl, n-propyl, isopropyl or cyclopropyl,
Q14, where $R^{11}$ represents hydrogen, methyl, ethyl, n-propyl, isopropyl, methylsulphonyl or cyclopropyl and $R^{13}$ represents methyl, ethyl, n-propyl, isopropyl, n-butyl, isobutyl, tert-butyl, cyclopropyl, fluoromethyl, difluoromethyl, trifluoromethyl, fluoroethyl, difluoroethyl, trifluoroethyl, tetrafluoroethyl or pentafluoroethyl,
Q17, where $R^{13}$ represents pyrazolyl which is optionally monosubstituted by trifluoromethyl,
Q18, where $R^8$ represents methyl, ethyl, n-propyl, isopropyl, n-butyl, isobutyl, tert-butyl, cyclopropyl or phenyl, $R^{11}$ represents hydrogen, methyl or ethyl and $R^{12}$ represents hydrogen, methyl or ethyl,
where, if $R^{2b}$ represents Q5, Q6, Q8 or Q9, n represents 2,
$R^3$ very particularly preferably represents fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl or trifluoromethylsulphinyl,
$R^4$ very particularly preferably represents hydrogen, fluorine, chlorine, bromine or cyano,
$R^5$ very particularly preferably represents methyl, ethyl, isopropyl, methoxymethyl or methoxyethyl,
n very particularly preferably represents 0, 1 or 2.

Configuration 5:
$A^1$ with emphasis represents nitrogen,
$A^2$ with emphasis represents —N—$R^5$,
$A^4$ with emphasis represents =C—H,
$R^1$ with emphasis represents ethyl or benzyl,
$R^{2a}$ with emphasis represents hydrogen,
$R^{2b}$ with emphasis represents a group selected from
    Q1, where $R^8$ represents methoxy,
    Q5, where m represents 0 or 2 and $R^{13}$ represents methyl, ethyl or isopropyl,
    Q10, where $R^{11}$ represents hydrogen or methylsulphonyl and $R^{12}$ represents hydrogen or methylsulphonyl,
    Q12, where $R^{11}$ represents hydrogen and $R^8$ represents trifluoromethyl, $CHF_2$, $CF_2CF_3$, $CF_2CHF_2$, $CH_2OCH_3$, cyclopropyl, cyclopropylmethyl (—$CH_2$-cyclopropyl) or phenyl,
    Q14, where $R^{11}$ represents hydrogen and $R^{13}$ represents methyl,
    Q17, where $R^{13}$ represents trifluoromethyl-1H-pyrazol-5-yl,
    where, if $R^{2b}$ represents Q5, n represents 2,
$R^3$ with emphasis represents trifluoromethyl,
$R^5$ with emphasis represents methyl,
n with emphasis represents 0, 1 or 2.

Configuration 5-2a:
$A^1$ with emphasis represents nitrogen,
$A^2$ with emphasis represents —N—$R^5$,
$A^4$ with emphasis represents =C—H,
$R^1$ with emphasis represents methyl, ethyl, n-propyl, isopropyl, n-butyl, isobutyl or tert-butyl,
$R^{2a}$ with emphasis represents hydrogen,
$R^{2b}$ with emphasis represents a group selected from
    Q1, where $R^8$ represents methoxy or ethoxy,
    Q3, where $R^{11}$ represents hydrogen or methyl and $R^{12}$ represents hydrogen, methyl, ethyl, n-propyl, isopropyl, n-butyl, isobutyl, tert-butyl or cyclopropyl,
    Q4, where $R^{11}$ represents hydrogen or methyl and $R^{12}$ represents methyl, ethyl, n-propyl, isopropyl, n-butyl, isobutyl, tert-butyl or cyclopropyl,
    Q5, where m represents 0, 1 or 2 and $R^{13}$ represents methyl, ethyl, n-propyl, isopropyl, n-butyl, isobutyl, tert-butyl, phenyl or benzyl,
    Q6, where $R^{13}$ represents methyl, ethyl, n-propyl, isopropyl, n-butyl, isobutyl or tert-butyl,
    Q8, where $R^{13}$ represents methyl, ethyl, n-propyl, isopropyl, n-butyl, isobutyl or tert-butyl,
    Q9, where $R^{11}$ represents hydrogen, methyl, ethyl, n-propyl, isopropyl or cyclopropyl and $R^2$ represents hydrogen, methyl, ethyl, n-propyl, isopropyl, n-butyl, isobutyl, tert-butyl or cyclopropyl,
    Q10, where $R^{11}$ represents hydrogen, methyl, ethyl, n-propyl, isopropyl or cyclopropyl and $R^{12}$ represents hydrogen, methyl, ethyl, n-propyl, isopropyl, n-butyl, isobutyl, tert-butyl or cyclopropyl,
    Q11, where $R^{11}$ represents hydrogen, methyl, ethyl, n-propyl, isopropyl, cyclopropyl or COmethyl (acetyl) and $R^{12}$ represents hydrogen, methyl, ethyl, n-propyl, isopropyl, n-butyl, isobutyl, tert-butyl, cyclopropyl or COmethyl (acetyl),
    Q12, where $R^{11}$ represents hydrogen or methyl and $R^8$ represents methyl, ethyl, n-propyl, isopropyl (only if $R^{11}$ does not represent hydrogen may $R^8$ represent methyl, ethyl, n-propyl, isopropyl), trifluoromethyl, $CHF_2$, $CF_2CF_3$, $CF_2CHF_2$, $CH_2OCH_3$, $CH_2SCH_3$, $CH_2OC_2H_5$, $CH_2SOCH_3$, $CH_2SO_2CH_3$, $CH(CH_3)CH_2SCH_3$, $CH(CH_3)CH_2SOCH_3$, $CH(CH_3)CH_2SO_2CH_3$, $C_2H_4OC_2H_5$, $C_2H_4SC_2H_5$, $C_2H_4OC_2H_5$, C$_2$H$_4$SOC$_2$H$_5$, C$_2$H$_4$SO$_2$C$_2$H$_5$, CH(CH$_3$)CH$_2$SC$_2$H$_5$, CH(CH$_3$)CH$_2$SOC$_2$H$_5$, CH(CH$_3$)CH$_2$SO$_2$C$_2$H$_5$, cyclopropyl, cyclopropylmethyl (—CH$_2$-cyclopropyl), phenyl, benzyl,

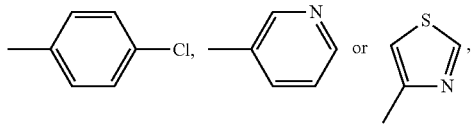

Q13, where R$^8$ represents methyl, ethyl, n-propyl, isopropyl, n-butyl, isobutyl, tert-butyl or cyclopropyl and R$^{11}$ represents hydrogen, methyl, ethyl, n-propyl, isopropyl or cyclopropyl, Q14, where R$^{11}$ represents hydrogen, methyl, ethyl, n-propyl, isopropyl, methylsulphonyl or cyclopropyl and R$^{13}$ represents methyl, ethyl, n-propyl, isopropyl, n-butyl, isobutyl, tert-butyl, cyclopropyl or trifluoromethyl, Q17, where R$^{13}$ represents trifluoromethyl-1H-pyrazol-5-yl

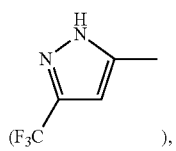

Q18, where R$^8$ represents cyclopropyl, R$^{11}$ represents hydrogen, methyl or ethyl and R$^{12}$ represents hydrogen, methyl or ethyl, where, if R$^{2b}$ represents Q5, Q6, Q8 or Q9, n represents 2, R$^3$ with emphasis represents fluoromethyl, difluoromethyl, trifluoromethyl, fluoroethyl, difluoroethyl, trifluoroethyl, tetrafluoroethyl or pentafluoroethyl, R$^5$ with emphasis represents methyl, ethyl or isopropyl, n with emphasis represents 0, 1 or 2.

Configuration 5-2b:

A$^1$ with emphasis represents nitrogen,
A$^2$ with emphasis represents —N—R$^5$,
A$^4$ with emphasis represents =C—H,
R$^1$ with emphasis represents ethyl,
R$^{2a}$ with emphasis represents hydrogen,
R$^{2b}$ with emphasis represents a group selected from Q1, where R$^8$ represents methoxy,
Q3, where R$^{11}$ represents hydrogen and R$^{12}$ represents hydrogen, methyl, ethyl or cyclopropyl,
Q4, where R$^{11}$ represents hydrogen and R$^{12}$ represents methyl, ethyl or cyclopropyl,
Q5, where m represents 0, 1 or 2 and R$^{13}$ represents methyl, ethyl, isopropyl, phenyl or benzyl,
Q6, where R$^{13}$ represents ethyl,
Q8, where R$^{13}$ represents methyl,
Q9, where R$^{11}$ represents hydrogen or methyl and R$^{12}$ represents methyl, ethyl or isopropyl,
Q10, where R$^{11}$ represents hydrogen or methyl and R$^{12}$ represents hydrogen, methyl or ethyl,
Q11, where R$^{11}$ represents hydrogen, methyl or COmethyl (acetyl) and R$^{12}$ represents hydrogen, methyl or COmethyl (acetyl),
Q12, where R$^{11}$ represents hydrogen or methyl and R$^8$ represents methyl (only if R$^{11}$ does not represent hydrogen), trifluoromethyl, CHF$_2$, CF$_2$CF$_3$, CF$_2$CHF$_2$, CH$_2$OCH$_3$, CH$_2$SCH$_3$, CH$_2$OC$_2$H$_5$, CH$_2$SOCH$_3$, CH$_2$SO$_2$CH$_3$, CH(CH$_3$)CH$_2$SCH$_3$, CH(CH$_3$)CH$_2$SOCH$_3$, CH(CH$_3$)CH$_2$SO$_2$CH$_3$, cyclopropyl, cyclopropylmethyl (—CH$_2$-cyclopropyl), phenyl, benzyl,

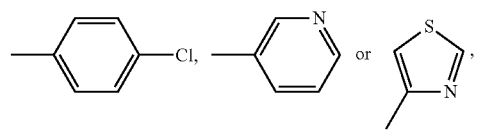

Q13, where R$^8$ represents methyl and R$^{11}$ represents hydrogen,
Q14, where R$^{11}$ represents hydrogen or methylsulphonyl and R$^3$ represents methyl, ethyl or trifluoromethyl,
Q17, where R$^{13}$ represents trifluoromethyl-1H-pyrazol-5-yl

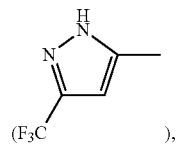

Q18, where R$^8$ represents cyclopropyl, R$^{11}$ represents hydrogen and R$^2$ represents hydrogen, where, if R$^{2b}$ represents Q5, Q6, Q8 or Q9, n represents 2, R$^3$ with emphasis represents trifluoromethyl or pentafluoroethyl, R$^5$ with emphasis represents methyl, n with emphasis represents 0, 1 or 2.

Configuration 6-2a:

A$^1$ especially represents nitrogen,
A$^2$ especially represents —N—R$^5$,
A$^4$ especially represents =C—H,
R$^1$ especially represents methyl, ethyl, n-propyl, isopropyl, n-butyl, isobutyl or tert-butyl,
R$^{2a}$ especially represents hydrogen,
R$^{2b}$ especially represents a group selected from

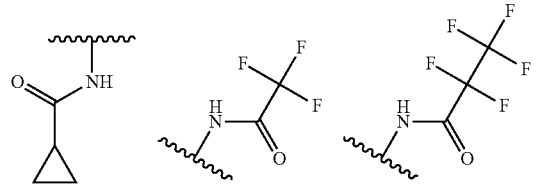

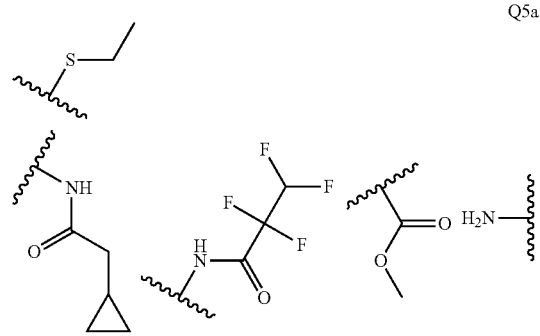

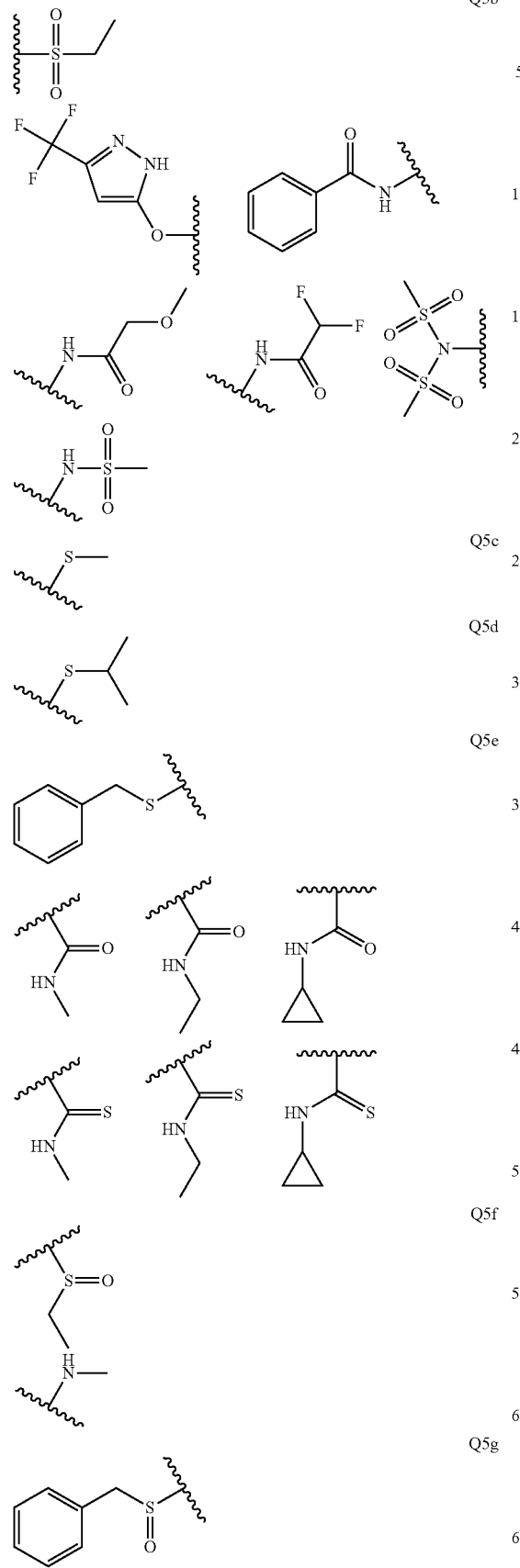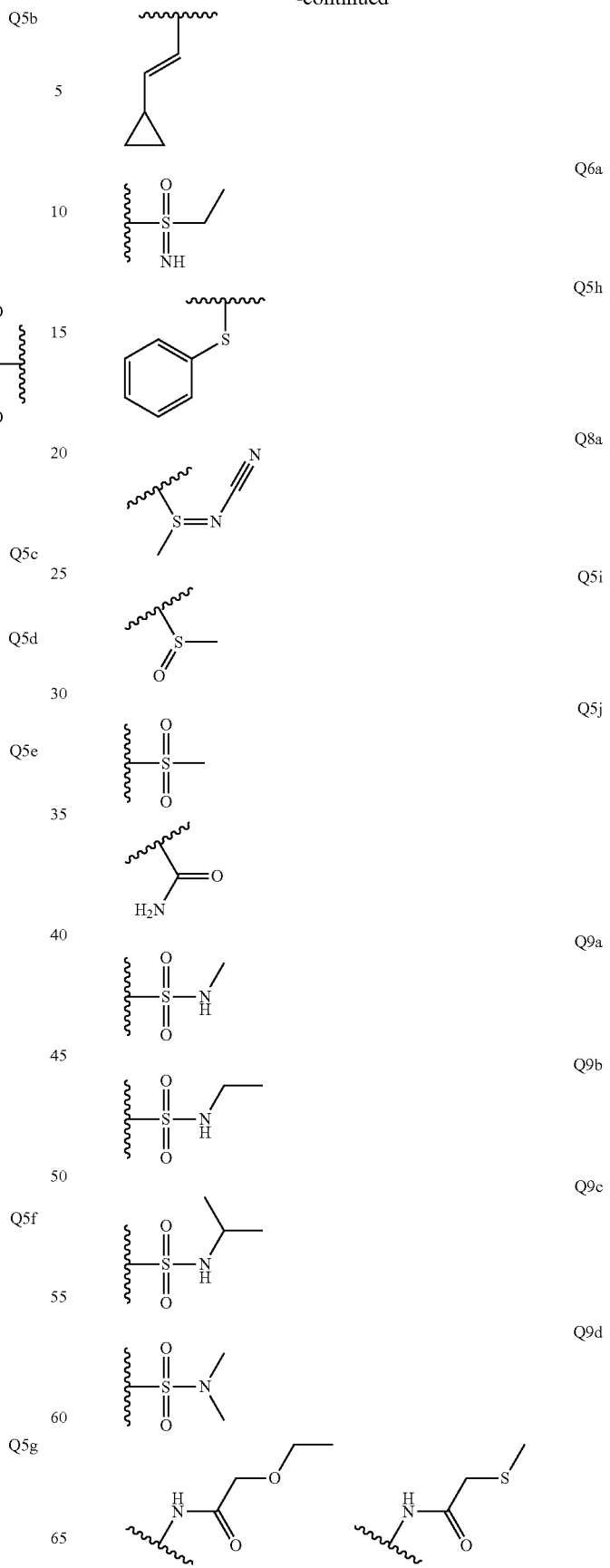

-continued

R³ especially represents fluoromethyl, difluoromethyl, trifluoromethyl, fluoroethyl, difluoroethyl, trifluoroethyl, tetrafluoroethyl or pentafluoroethyl, R⁵ especially represents methyl, ethyl or isopropyl, n especially represents 0 or 2, where, if $R^{2b}$ represents Q5a-j, Q6a, Q8a, Q9a-d, then n represents 2.

Configuration 6-2b:
$A^1$ especially represents nitrogen,
$A^2$ especially represents —N—$R^5$,
$A^4$ especially represents =C—H,
$R^1$ especially represents ethyl,
$R^{2a}$ especially represents hydrogen,
$R^{2b}$ has the meanings given in Configuration (6-2a),
$R^3$ especially represents trifluoromethyl or pentafluoroethyl,
$R^5$ especially represents methyl,
n especially represents 0 or 2, where, if $R^{2b}$ represents Q5a-j, Q6a, Q8a, Q9a-d, then n represents 2.

$A^1$ represents =N⁺—O⁻ means =N⁺(O⁻)—; $A^1$ represents =C—$R^4$ means =C($R^4$)— (identical to $CR^4$), $A^2$ represents —N—$R^5$ means —N($R^5$)— (identical to N—$R^5$); $A^4$ represents =N⁺—O⁻ means =N⁺(O⁻)—; $A^4$ represents =C—$R^4$ means =C($R^4$)— (identical to $CR^4$).

If $R^{2b}$ represents Q11 (—$NR^{11}$—$NR^{11}R^{12}$), then $R^{11}$ at one of the nitrogen atoms may have a meaning different from that at the other nitrogen atom, for example in compound 74 where $R^{11}$ at one of the nitrogen atoms represents methyl and at the other nitrogen atom represents hydrogen, $R^{12}$ in compound 74 represents hydrogen.

In a further embodiment, the invention relates to compounds of the formula (I-A)

where $R^1$, $R^{2a}$, $R^{2b}$, $R^3$, $R^5$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b) or configuration (6-2a) or configuration (6-2b).

In a further embodiment, the invention relates to compounds of the formula (I-A) where $R^{2b}$ represents Q1 and $R^1$, $R^{2a}$, $R^3$, $R^5$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I-A) where $R^{2b}$ represents Q2 and $R^1$, $R^{2a}$, $R^3$, $R^5$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-A) where $R^{2b}$ represents Q3 and $R^1$, $R^{2a}$, $R^3$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2b).

In a further embodiment, the invention relates to compounds of the formula (I-A) where $R^{2b}$ represents Q4 and $R^1$, $R^2$, $R^3$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2b).

In a further embodiment, the invention relates to compounds of the formula (I-A) where $R^{2b}$ represents Q5 and $R^1$, $R^{2a}$, $R^3$, $R^5$, $R^{13}$, m and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I-A) where $R^{2b}$ represents Q6 and $R^1$, $R^{2a}$, $R^3$, $R^5$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I-A) where $R^{2b}$ represents Q7 and $R^1$, $R^{2a}$, $R^3$, $R^5$, $R^{13}$ and n have the meanings described above, in particular the meanings described in configuration (1) or configuration (1-1) or configuration (1-2) or configuration (2) or configuration (2-1) or configuration (3) or configuration (3-1) or configuration (4) or configuration (4-1).

In a further embodiment, the invention relates to compounds of the formula (I-A) where $R^{2b}$ represents Q8 and $R^1$, $R^{2a}$, $R^3$, $R^5$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I-A) where $R^{2b}$ represents Q9 and $R^1$, $R^2$, $R^3$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2b).

In a further embodiment, the invention relates to compounds of the formula (I-A) where $R^{2b}$ represents Q10 and $R^1$, $R^{2a}$, $R^3$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I-A) where $R^{2b}$ represents Q11 and $R^1$, $R^{2a}$, $R^3$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2b).

In a further embodiment, the invention relates to compounds of the formula (I-A) where $R^{2b}$ represents Q12 and $R^1$, $R^{2a}$, $R^3$, $R^5$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I-A) where $R^{2b}$ represents Q13 and $R^1$, $R^2$, $R^3$, $R^5$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2b).

In a further embodiment, the invention relates to compounds of the formula (I-A) where $R^{2b}$ represents Q14 and $R^1$, $R^2$, $R^3$, $R^5$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I-A) where $R^{2b}$ represents Q15 and $R^1$, $R^2$, $R^3$, $R^5$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-A) where $R^{2b}$ represents Q16 and $R^1$, $R^2$, $R^3$, $R^5$, $R^{14}$, $R^{15}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-A) where $R^{2b}$ represents Q17 and $R^1$, $R^{2a}$, $R^3$, $R^5$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I-A) where $R^{2b}$ represents Q18 and $R^1$, $R^{2a}$, $R^3$, $R^5$, $R^8$, $R^{11}$, $R^{12}$ and n have the meanings described above, in particular the meanings described in configuration (1-2) or configuration (2-2) or configuration (3-2) or configuration (4-2) or configuration (5-2a) or configuration (5-2b).

In a further embodiment, the invention relates to compounds of the formula (I-B)

where $R^1$, $R^{2a}$, $R^{2b}$, $R^3$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q1 and $R^1$, $R^{2a}$, $R^3$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q2 and $R^1$, $R^{2a}$, $R^3$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-B) where $R^{2b}$ represents Q3 and $R^1$, $R^{2a}$, $R^3$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q4 and $R^1$, $R^{2a}$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q5 and $R^1$, $R^{2a}$, $R^3$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q6 and $R^1$, $R^{2a}$, $R^3$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q7 and $R^1$, $R^{2a}$, $R^3$, $R^{13}$ and n have the meanings described above, in particular the meanings described in configuration (1) or configuration (1-1) or configuration (1-2) or configuration (2) or configuration (2-1) or configuration (3) or configuration (3-1) or configuration (4) or configuration (4-1).

In a further embodiment, the invention relates to compounds of the formula (I-B) where $R^{2b}$ represents Q8 and $R^1$, $R^{2a}$, $R^3$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q9 and $R^1$, $R^{2a}$, $R^3$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q10 and $R^1$, $R^{2a}$, $R^3$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q11 and $R^1$, $R^{2a}$, $R^3$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q12 and $R^1$, $R^{2a}$, $R^3$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q13 and $R^1$, $R^{2a}$, $R^3$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q14 and $R^1$, $R^{2a}$, $R^3$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q15 and $R^1$, $R^{2a}$, $R^3$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-B) where $R^{2b}$ represents Q16 and $R^1$, $R^2$, $R^3$, $R^{14}$, $R^{15}$, p and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-B) where $R^{2b}$ represents Q17 and $R^1$, $R^2$, $R^3$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-B) where $R^{2b}$ represents Q18 and $R^1$, $R^{2a}$, $R^3$, $R^8$, $R^{11}$, $R^{12}$ and n have the meanings described above, in particular the meanings described in configuration (1-2) or configuration (2-2) or configuration (3-2) or configuration (4-2).

In a further embodiment, the invention relates to compounds of the formula (I-C)

where $R^1$, $R^{2a}$, $R^{2b}$, $R^3$, $R^4$, $R^5$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q1 and $R^1$, $R^{2a}$, $R^3$, $R^4$, $R^5$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q2 and $R^1$, $R^{2a}$, $R^3$, $R^4$, $R^5$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-C) where $R^{2b}$ represents Q3 and $R^1$, $R^{2a}$, $R^3$, $R^4$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q4 and $R^1$, $R^{2a}$, $R^3$, $R^4$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q5 and $R^1$, $R^{2a}$, $R^3$, $R^4$, $R^5$, $R^{13}$, m and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q6 and $R^1$, $R^{2a}$, $R^3$, $R^4$, $R^5$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q7 and $R^1$, $R^{2a}$, $R^3$, $R^5$, $R^{13}$ and n have the meanings described above, in particular the meanings described in configuration (1) or configuration (1-1) or configuration (1-2) or configuration (2) or configuration (2-1) or configuration (3) or configuration (3-1) or configuration (4) or configuration (4-1).

In a further embodiment, the invention relates to compounds of the formula (I-C) where $R^{2b}$ represents Q8 and $R^1$, $R^{2a}$, $R^3$, $R^4$, $R^5$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q9 and $R^1$, $R^{2a}$, $R^3$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q10 and $R^1$, $R^{2a}$, $R^3$, $R^4$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q11 and $R^1$, $R^{2a}$, $R^3$, $R^4$, $R^5$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q12 and $R^1$, $R^{2a}$, $R^3$, $R^4$, $R^5$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q13 and $R^1$, $R^2$, $R^3$, $R^4$, $R^5$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q14 and $R^1$, $R^2$, $R^3$, $R^4$, $R^5$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q15 and $R^1$, $R^2$, $R^3$, $R^4$, $R^5$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-C) where $R^{2b}$ represents Q16 and $R^1$, $R^2$, $R^3$, $R^5$, $R^{14}$, $R^{15}$, p and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-C) where $R^{2b}$ represents Q17 and $R^1$, $R^{2a}$, $R^3$, $R^4$, $R^5$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-C) where $R^{2b}$ represents Q18 and $R^1$, $R^{2a}$, $R^3$, $R^4$, $R^5$, $R^8$, $R^{11}$, $R^{12}$ and n have the meanings described above, in particular the meanings described in configuration (1-2) or configuration (2-2) or configuration (3-2) or configuration (4-2).

In a further embodiment, the invention relates to compounds of the formula (I-D)

where $R^1$, $R^{2a}$, $R^{2b}$, $R^3$, $R^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q1 and $R^1$, $R^{2a}$, $R^3$, $R^4$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q2 and $R^1$, $R^{2a}$, $R^3$, $R^4$, $R^8$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-D) where $R^{2b}$ represents Q3 and $R^1$, $R^{2a}$, $R^3$, $R^4$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q4 and $R^1$, $R^{2a}$, $R^3$, $R^4$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q5 and $R^1$, $R^{2a}$, $R^3$, $R^4$, $R^{13}$, m and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q6 and $R^1$, $R^{2a}$, $R^3$, $R^4$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q7 and $R^1$, $R^{2a}$, $R^3$, $R^{13}$ and n have the meanings described above, in particular the meanings described in configuration (1) or configuration (1-1) or configuration (1-2) or configuration (2) or configuration (2-1) or configuration (3) or configuration (3-1) or configuration (4) or configuration (4-1).

In a further embodiment, the invention relates to compounds of the formula (I-D) where $R^{2b}$ represents Q8 and $R^1$, $R^{2a}$, $R^3$, $R^4$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q9 and $R^1$, $R^{2a}$, $R^3$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q10 and $R^1$, $R^{2a}$, $R^3$, $R^4$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q11 and $R^1$, $R^{2a}$, $R^3$, $R^4$, $R^{11}$, $R^{12}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q12 and $R^1$, $R^{2a}$, $R^3$, $R^4$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q13 and $R^1$, $R^{2a}$, $R^3$, $R^4$, $R^8$, $R^{11}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q14 and $R^1$, $R^{2a}$, $R^3$, $R^4$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q15 and $R^1$, $R^{2a}$, $R^3$, $R^4$, $R^{11}$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-D) where $R^{2b}$ represents Q16 and $R^1$, $R^2$, $R^3$, $R^{14}$, $R^{15}$, p and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I-D) where $R^{2b}$ represents Q17 and $R^1$, $R^{2a}$, $R^3$, $R^4$, $R^{13}$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2).

In a further embodiment, the invention relates to compounds of the formula (I-D) where $R^{2b}$ represents Q18 and $R^1$, $R^{2a}$, $R^3$, $R^4$, $R^8$, $R^{11}$, $R^{12}$ and n have the meanings described above, in particular the meanings described in configuration (1-2) or configuration (2-2) or configuration (3-2) or configuration (4-2).

In a further embodiment, the invention relates to compounds of the formula (I(Q1))

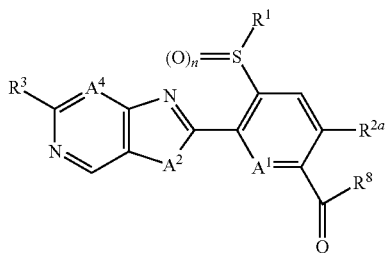

where R$^{2b}$ represents —C(=O)—R$^8$ (Q1) and where R$^1$, R$^{2a}$, R$^3$, R$^8$, A$^1$, A$^2$, A$^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I(Q2))

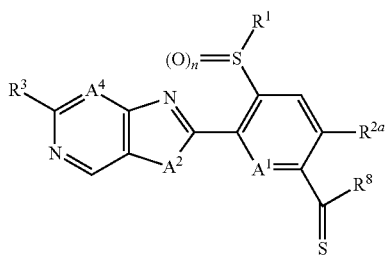

where R$^{2b}$ represents —C(=S)—R$^8$ (Q2) and where R$^1$, R$^{2a}$, R$^3$, R$^8$, A$^1$, A$^2$, A$^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I(Q3))

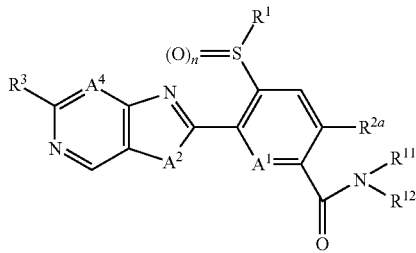

where R$^{2b}$ represents —C(=O)—NR$^{11}$R$^{12}$ (Q3) and where R$^1$, R$^{2a}$, R$^3$, R$^{11}$, R$^{12}$, A$^1$, A$^2$, A$^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I(Q4))

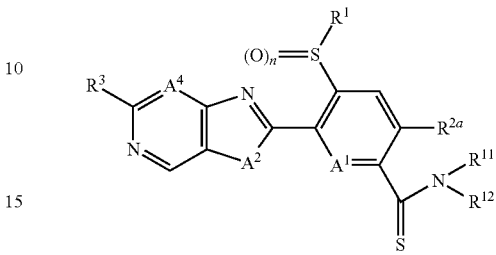

where R$^{2b}$ represents —C(=S)—NR$^{11}$R$^{12}$ (Q4) and where R$^1$, R$^{2a}$, R$^3$, R$^{11}$, R$^{12}$, A$^1$, A$^2$, A$^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I(Q5))

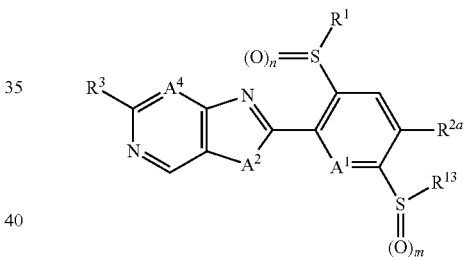

where R$^{2b}$ represents —S(O)$_m$—R$^{13}$ (Q5) and where R$^1$, R$^{2a}$, R$^3$, R$^{13}$, A$^1$, A$^2$, A$^4$, m and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I(Q6))

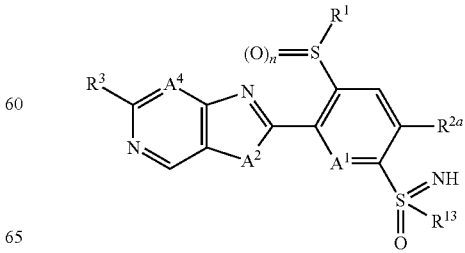

where $R^{2b}$ represents —S=O(=NH)—$R^{13}$ (Q6) and where $R^1$, $R^{2a}$, $R^3$, $R^{13}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I(Q7))

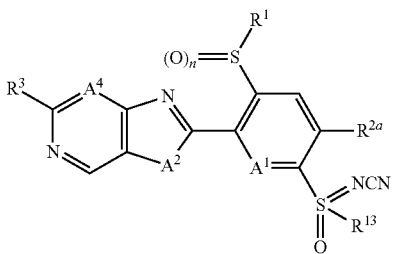

where $R^{2b}$ represents —S=O(=N—CN)—$R^{13}$ (Q7) and where $R^1$, $R^{2a}$, $R^3$, $R^{13}$, $A^1$, $A^2$, $A^4$ and n have the meanings described above, in particular the meanings described in configuration (1) or configuration (1-1) or configuration (1-2) or configuration (2) or configuration (2-1) or configuration (3) or configuration (3-1) or configuration (4) or configuration (4-1).

In a further embodiment, the invention relates to compounds of the formula (I(Q8))

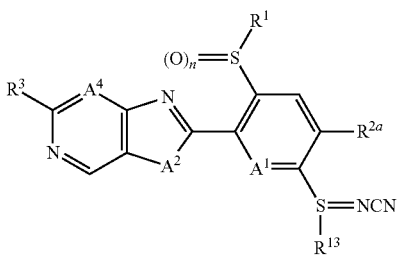

where $R^{2b}$ represents —S(=N—CN)—$R^{13}$ (Q8) and where $R^1$, $R^{2a}$, $R^3$, $R^{13}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I(Q9))

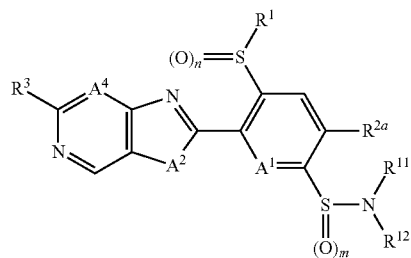

where $R^{2b}$ represents —S(O)$_2$—$NR^{11}R^{12}$ (Q9) and where $R^1$, $R^{2a}$, $R^3$, $R^{11}$, $R^{12}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I(Q10))

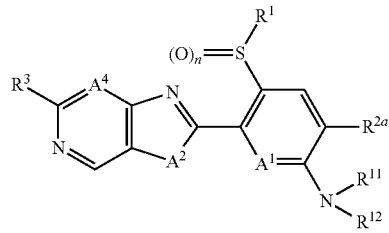

where $R^{2b}$ represents —$NR^{11}R^{12}$ (Q10) and where $R^1$, $R^{2a}$, $R^3$, $R^{11}$, $R^{12}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I(Q11))

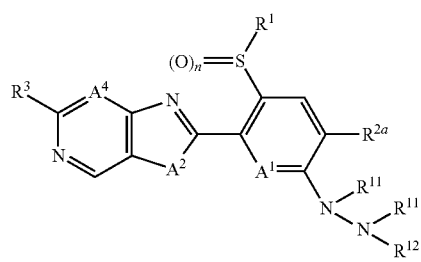

where $R^{2b}$ represents —$NR^{11}$—$NR^{11}R^{12}$ (Q11) and where $R^1$, $R^{2a}$, $R^3$, $R^{11}$, $R^{12}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I(Q12))

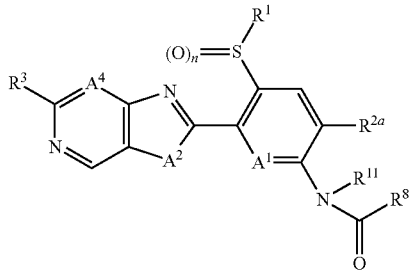

where $R^{2b}$ represents —NR$^{11}$—C(=O)—R$^8$ (Q12) and where $R^1$, $R^{2a}$, $R^3$, $R^8$, $R^{11}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I(Q13))

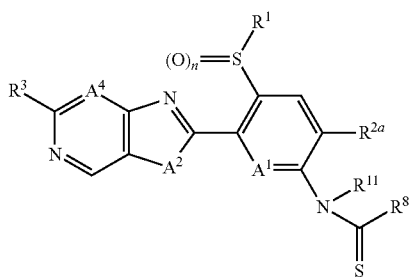

where $R^{2b}$ represents —NR$^{11}$—C(=S)—R$^8$ (Q13) and where $R^1$, $R^{2a}$, $R^3$, $R^8$, $R^{11}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

In a further embodiment, the invention relates to compounds of the formula (I(Q14))

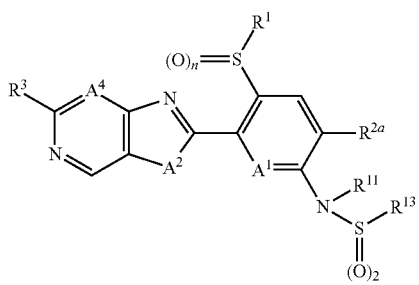

where $R^{2b}$ represents —NR$^{11}$—S(O)$_2$—R$^3$ (Q14) and where $R^1$, $R^{2a}$, $R^3$, $R^{11}$, $R^{13}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I(Q15))

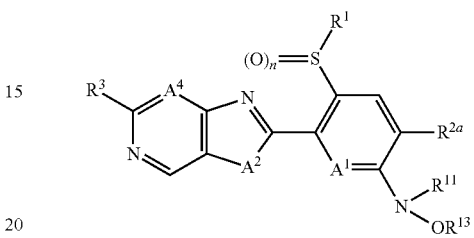

where $R^{2b}$ represents —N(R$^{11}$)—O—R$^{13}$ (Q15) and where $R^1$, $R^{2a}$, $R^3$, $R^{11}$, $R^{13}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I(Q16))

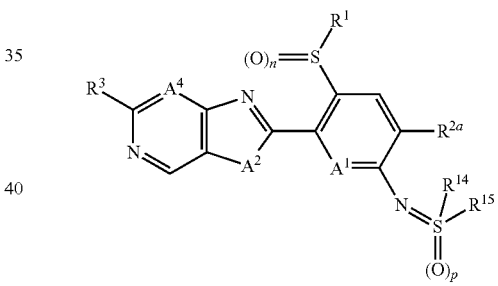

where $R^{2b}$ represents —N=S(O)$_p$—R$^{14}$R$^{15}$ (Q16) and where $R^1$, $R^{2a}$, $R^3$, $R^{11}$, $R^{13}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (4) or configuration (4-1).

In a further embodiment, the invention relates to compounds of the formula (I(Q17))

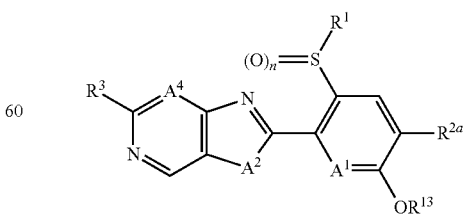

where $R^{2b}$ represents —O—R$^{13}$ (Q17) and where $R^1$, $R^{2a}$, $R^3$, $R^{13}$, $A^1$, $A^2$, $A^4$ and n have the meanings described above, in particular the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5) or configuration (5-2a) or configuration (5-2b).

In a further embodiment, the invention relates to compounds of the formula (I(Q18))

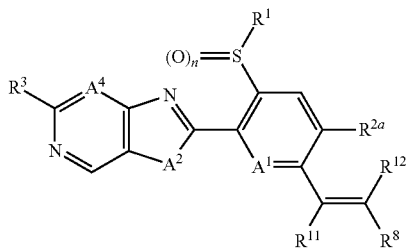

where $R^{2b}$ represents —$CR^{11}$=$CR^8R^{12}$ (Q18) and where $R^1$, $R^{2a}$, $R^3$, $R^8$, $R^{11}$, $R^{12}$, $A^1$, $A^2$, $A^4$ and n have the meanings described above, in particular the meanings described in configuration (1-2) or configuration (2-2) or configuration (3-2) or configuration (4-2) or configuration (5-2a) or configuration (5-2b).

In a further embodiment, the invention relates to compounds of the formula (I) where $R^1$, $R^{2a}$, $R^3$, $R^8$, $R^{11}$, $R^{12}$, $A^1$, $A^2$, $A^4$ and n have the meanings described above, in particular the meanings described in configuration (1) or configuration (1-1) or configuration (2) or configuration (2-1) or configuration (3) or configuration (3-1) or configuration (4) or configuration (4-1) and $R^{2b}$ represents a group selected from Q1, Q2, Q3 and Q4.

In a further embodiment, the invention relates to compounds of the formula (I) where $R^1$, $R^{2a}$, $R^3$, $R^{11}$, $R^{12}$, $R^{13}$, $A^1$, $A^2$, $A^4$, m and n have the meanings described above, in particular the meanings described in configuration (1) or configuration (1-1) or configuration (2) or configuration (2-1) or configuration (3) or configuration (3-1) or configuration (4) or configuration (4-1) and $R^{2b}$ represents a group selected from Q5, Q6, Q7, Q8 and Q9.

In a further embodiment, the invention relates to compounds of the formula (I) where $R^1$, $R^{2a}$, $R^3$, $R^8$, $R^1$, $R^{12}$, $R^{13}$, $R^{14}$, $R^5$, $A^1$, $A^2$, $A^4$, p and n have the meanings described above, in particular the meanings described in configuration (1) or configuration (1-1) or configuration (2) or configuration (2-1) or configuration (3) or configuration (3-1) or configuration (4) or configuration (4-1) and $R^{2b}$ represents a group selected from Q10, Q11, Q12, Q13, Q14, Q15 and Q16.

In a further embodiment, the invention relates to compounds of the formula (I) where $R^1$, $R^{2a}$, $R^3$, $R^8$, $R^{11}$, $R^{12}$, $R^3$, $R^{14}$, $R^{15}$, $A^1$, $A^2$, $A^4$, p and n have the meanings described above, in particular the meanings described in configuration (1) or configuration (1-1) or configuration (2) or configuration (2-1) or configuration (3) or configuration (3-1) or configuration (4) or configuration (4-1) and R2b represents a group selected from Q10, Q11, Q13, Q14, Q15 and Q16.

In a further embodiment, the invention relates to compounds of the formula (I) where $R^1$, $R^{2a}$, $R^3$, $R^{13}$, $A^1$, $A^2$, $A^4$ and n have the meanings described above, in particular the meanings described in configuration (1) or configuration (1-1) or configuration (2) or configuration (2-1) or configuration (3) or configuration (3-1) or configuration (4) or configuration (4-1) or configuration (5) and $R^{2b}$ represents a group selected from Q17.

In the preferred definitions, unless stated otherwise,
halogen is selected from the group consisting of fluorine, chlorine, bromine and iodine, preferably in turn from the group consisting of fluorine, chlorine and bromine,
aryl (including as part of a larger unit, for example arylalkyl) is selected from the group consisting of phenyl, naphthyl, anthryl, phenanthrenyl, and is preferably in turn phenyl,
hetaryl (synonymous with heteroaryl or aromatic heterocycle, including as part of a larger unit, for example hetarylalkyl) is selected from the group consisting of furyl, thienyl, pyrrolyl, pyrazolyl, imidazolyl, triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, pyridyl, pyrimidyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl,
heterocyclyl is a saturated 3-, 4-, 5- or 6-membered ring containing 1 or 2 nitrogen atoms and/or one oxygen atom and/or one sulphur atom, for example aziridinyl, oxiranyl, thiiranyl, azetidinyl, pyrrolidinyl, piperidinyl, oxetanyl, tetrahydrofuranyl, tetrahydropyranyl, dioxanyl, thietanyl, tetrahydrothiophenyl, tetrahydrothiopyranyl, piperazinyl, morpholinyl and thiomorpholinyl.

In the particularly preferred definitions, unless stated otherwise,
halogen is selected from the group consisting of fluorine, chlorine, bromine and iodine, preferably in turn from the group consisting of fluorine, chlorine and bromine,
aryl (including as part of a larger unit, for example arylalkyl) is selected from the group consisting of phenyl, naphthyl, anthryl, phenanthrenyl, and is preferably in turn phenyl,
hetaryl (including as part of a larger unit, for example hetarylalkyl) is selected from the group consisting of pyridyl, pyrimidyl, pyrazinyl, pyridazinyl, pyrazolyl, imidazolyl, triazolyl, thiazolyl and tetrazolyl,
heterocyclyl is selected from the group consisting of oxetanyl, tetrahydrofuryl and piperazinyl.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. From among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl.

Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms can be identical or different. In this case, halogen is fluorine, chlorine, bromine or iodine, especially fluorine, chlorine or bromine.

Unless stated otherwise, optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective ranges of preference.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the definitions listed above as being very particularly preferred.

Emphasis according to the invention is given to using compounds of the formula (I) which contain a combination of the meanings listed above as being emphasized.

Special emphasis according to the invention is given to using compounds of the formula (I) which contain a combination of the meanings listed above as being especially emphasized.

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

The compounds of the formula (I) according to the invention can be obtained by the processes shown in the following schemes:

Process A

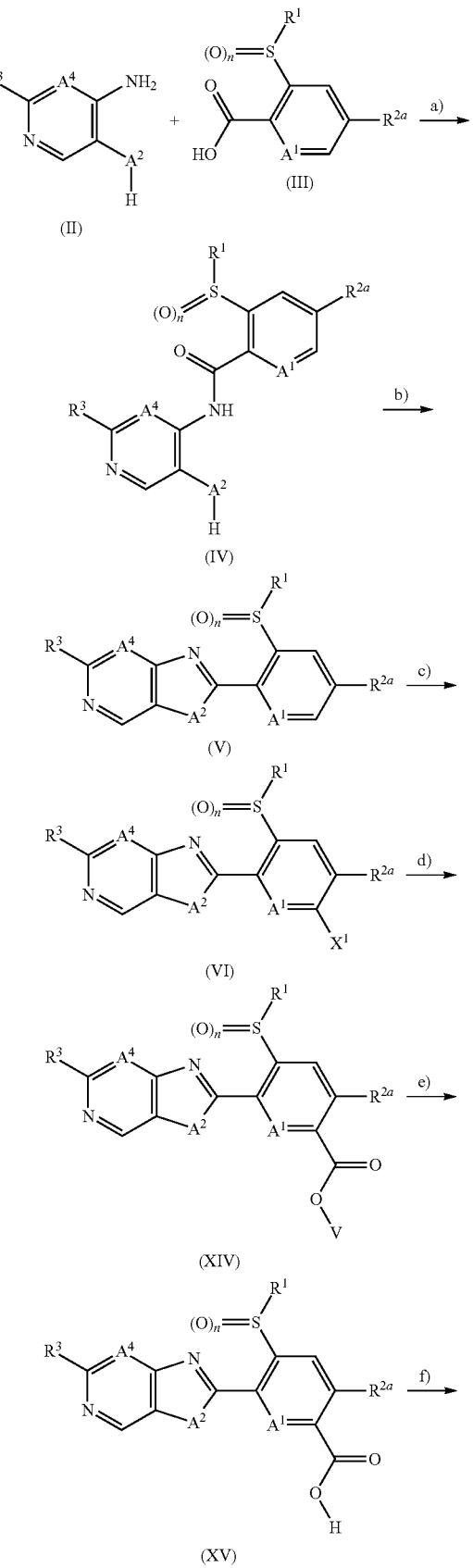

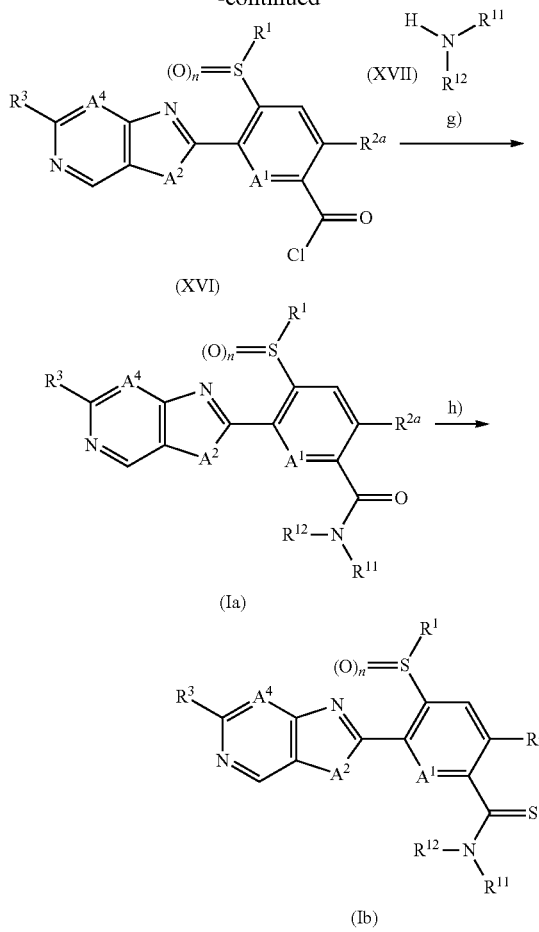

The radicals $R^1$, $R^{2a}$, $R^3$, $R^{11}$, $R^{12}$, $A^1$, $A^2$, $A^4$ and n have the meanings described above and $X^1$ represents halogen and V represents $(C_1\text{-}C_4)$-alkyl.

Step a)

The compounds of the formula (IV) can be prepared in analogy to the process described in U.S. Pat. No. 5,576,335 by the reaction of compounds of the formula (II) with carboxylic acids of the formula (III) in the presence of a condensing agent.

Compounds of the formula (II) are either commercially available or can be prepared by known methods, for example analogously to the processes described in US2003/69257 or WO2006/65703.

Carboxylic acids of the formula (III) are either commercially available or can be prepared by known methods, for example analogously to the processes described in US2010/234604, WO2012/61926 or Bioorganic and Medicinal Chemistry Letters, 18 (2008), 5023-5026.

The reaction of the compounds of the formula (II) with carboxylic acids of the formula (III) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

The reaction can be carried out under reduced pressure, at atmospheric pressure or under elevated pressure and at temperatures of 0 to 180° C.; with preference, the reaction is carried out at atmospheric pressure and temperatures of 20 to 140° C.

Step b)

The compounds of the formula (V) can be prepared by condensing the compounds of the formula (IV), for example analogously to the processes described in WO2012/86848.

The conversion to compounds of the formula (V) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be carried out under reduced pressure, at atmospheric pressure or under elevated pressure, and at temperatures of 0° C. to 200° C.

Step c)

The compounds of the formula (VI) can be prepared by halogenating the compounds of the formula (V), for example analogously to the processes described in U.S. Pat. No. 4,801,593. An example of a suitable halogenating agent is phosphorus oxychloride. Useful solvents or diluents include all inert organic solvents, for example aliphatic or aromatic hydrocarbons. Preference is given to using toluene.

In a further embodiment, the nitrogen ($A^1$=N) in the vicinity of the halogenation position is initially oxidized, for example analogously to the processes described in WO2008/112646. Examples of suitable oxidizing agents are meta-chloroperbenzoic acid and hydrogen peroxide. The reaction is preferably carried out in a solvent selected from customary solvents which are inert under the prevailing reaction conditions. Preference is given to halogenated hydrocarbons such as, for example, dichloromethane, chloroform, or to esters such as ethyl acetate. The subsequent halogenation is carried out as described above using a suitable halogenating agent such as, for example, phosphorus oxychloride.

Step d)

The compounds of the formula (XIV) can be prepared by carbonylation of the compounds of the formula (VI) analogously to S. A. Vinogradov, D. F. Wilson, Tetrahedron Letters 39 (1998), 8935-8938. The radical V is preferably methyl, ethyl, n-propyl or n-butyl. Suitable for use as catalysts for reaction d) are palladium phosphane complexes, for example a catalyst of palladium chloride, triphenylphosphane and DPPP (1,3-bis(diphenylphosphino)propane) (1:1:1). Preferred bases are, for example, Hünig's base (diisopropylethylamine) or DBU (1,8-diazabicyclo[5.4.0] undec-7-ene).

Steps e, f, g)

The ester of the formula (XIV) can be converted by standard methods, cf. DE 2221647, first into the acid of the formula (XV), for example using an alkali metal hydroxide such as sodium hydroxide or lithium hydroxide as base in an alcohol such as, for example, ethanol or a mixture of tetrahydrofuran and water as solvent.

The acid of the formula (XV) is then converted by standard methods into the acid chloride of the formula (XVI), for example using a chlorinating agent such as thionyl chloride or oxalyl chloride.

Further reaction with the amine of the formula (XVII) in a diluent such as, for example, dichloromethane or tetrahydrofuran, and in the presence of a base such as, for example, triethylamine or diisopropylethylamine, affords the compounds of the formula (Ia) (corresponds to formula I(Q3)) according to the invention.

Compounds of the formula (XVII) are either commercially available or can be prepared by known methods.

Step h)

Thioamides of the formula (Ib) (corresponds to formula I(Q4)) can be prepared from the carboxamides of the formula (Ia) by reaction with a sulfurizing agent, for example Lawesson's reagent or $P_4S_{10}$.

Process B

The radicals $R^1$, $R^{2a}$, $R^3$, $A^1$, $A^2$, $A^4$ and n have the meanings described above.

In a further embodiment of the invention, compounds of the formula (V) can be prepared in a one-stage process from the compounds of the formula (II) using compounds of the formula (III) in the presence of a condensing agent.

The conversion to compounds of the formula (V) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; alcohols such as methanol, ethanol or isopropanol; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

The reaction can be carried out in the presence of an acid or a base.

Examples of an acid which can be used in the reaction described are sulphonic acids such as methanesulphonic acid or para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

The reaction can be carried out in the presence of a suitable catalyst, for example 1-hydroxybenzotriazole.

The reaction can be carried out under reduced pressure, at atmospheric pressure or under elevated pressure, and at temperatures of 0° C. to 200° C.

The further conversion of the compounds of the formula (V) to compounds of the formula (I) is carried out analogously to process A.

Process C

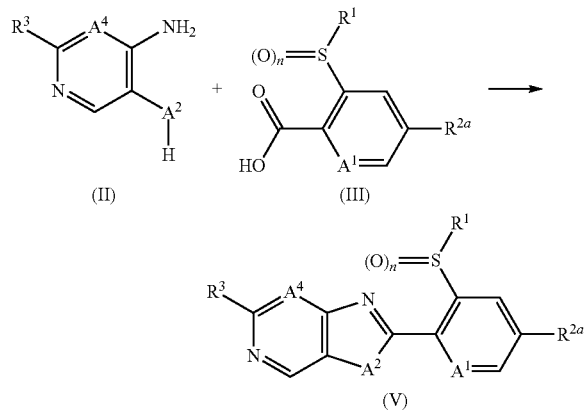

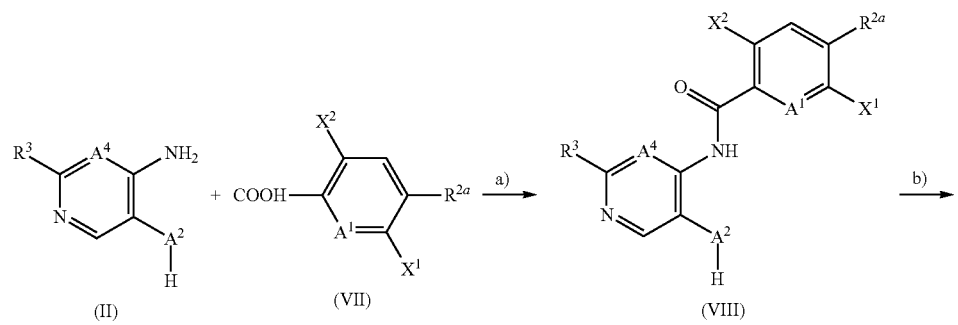

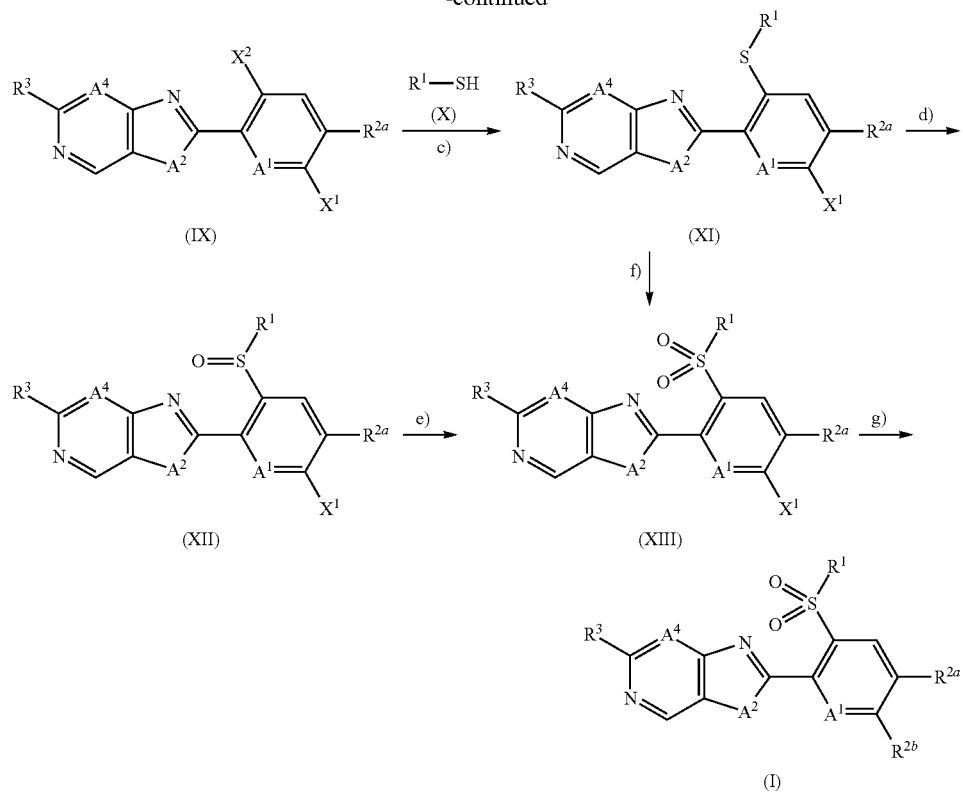

The radical $R^1$, $R^{2a}$, $R^{2b}$, $R^3$, $A^1$, $A^2$ and $A^4$ have the meanings described above and $X^1$ and $X^2$ represent halogen.

Step a)

The compounds of the formula (VIII) can be prepared in analogy to the process described in U.S. Pat. No. 5,576,335 by the reaction of compounds of the formula (II) with a carboxylic acid of the formula (VII) in the presence of a condensing agent or a base.

Compounds of the formula (II) are either commercially available or can be prepared by known methods, for example analogously to the processes described in US2003/69257 or WO2006/65703.

Carboxylic acids of the formula (VII) are either commercially available or can be prepared by known methods, for example analogously to the processes described in US2010/234604, WO2012/61926 or Bioorganic and Medicinal Chemistry Letters, 18 (2008), 5023-5026.

The reaction of the compounds of the formula (II) with carboxylic acids of the formula (VII) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate.

The reaction can be carried out under reduced pressure, at atmospheric pressure or under elevated pressure and at temperatures of 0 to 180° C.; with preference, the reaction is carried out at atmospheric pressure and temperatures of 20 to 140° C.

Step b)

The compounds of the formula (IX) can be prepared by condensing the intermediates of the formula (VIII), for example analogously to the processes described in WO2012/86848.

The conversion to compounds of the formula (IX) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be carried out under reduced pressure, at atmospheric pressure or under elevated pressure, and at temperatures of 0° C. to 200° C.

Step c)

The compounds of the formula (XI) can be prepared by reacting the compounds of the formula (IX) with the compounds of the formula (X) in the presence of a base.

Mercaptan derivatives of the formula (X), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formula (XI) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given to caesium carbonate, sodium carbonate and potassium carbonate. Further suitable bases are alkali metal hydrides, for example sodium hydride.

The reaction can be carried out under reduced pressure, at atmospheric pressure or under elevated pressure, and at temperatures of 0° C. to 200° C.

Step d)

The compounds of the formula (XII) can be prepared by oxidizing the compounds of the formula (XI). The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be carried out under reduced pressure, at atmospheric pressure or under elevated pressure, and at temperatures of −20° C. to 120° C.

Step e)

The compounds of the formula (XIII) can be prepared by oxidizing the compounds of the formula (XII). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of −20° C. to 120° C.

Step f)

The compounds of the formula (XIII) can also be prepared in a one-step process by oxidizing the compounds of the formula (XI). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of −20° C. to 120° C.

Step g)

The further conversion of the compounds of the formula (XIII) to compounds of the formula (I) is carried out analogously to process A.

The compounds of the formulae (XI) and (XII) can be converted analogously to process A to compounds of the formula (I).

Process D

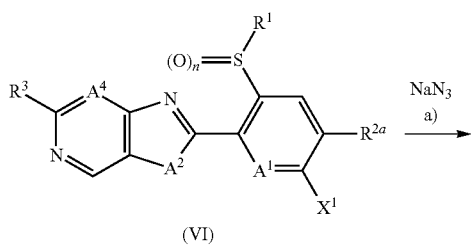

(VI)

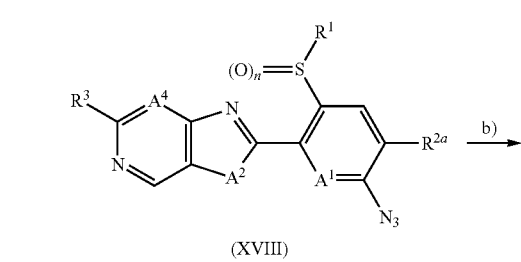

(XVIII)

-continued

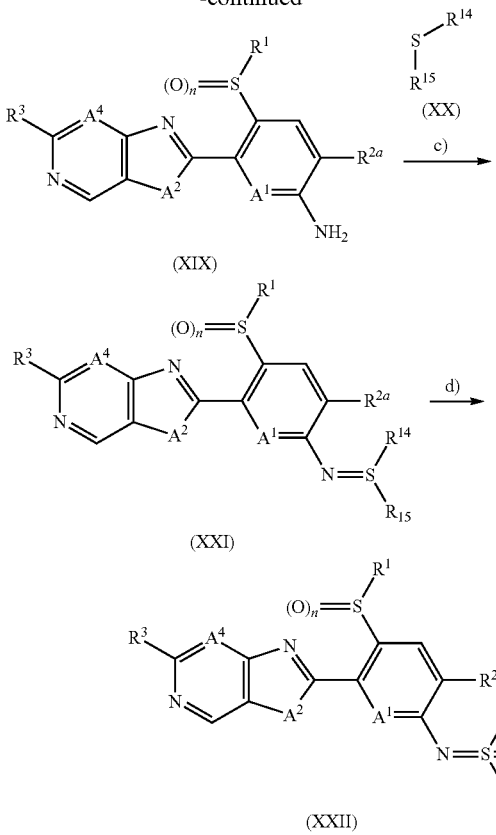

The radicals $R^1$, $R^{2a}$, $R^3$, $R^8$, $R^{14}$, $R^5$, $A^1$, $A^2$, $A^4$ and n have the meanings described above and $X^1$ represents halogen.

Step a)

The compounds of the formula (XVIII) can be prepared analogously to WO2015/002211 by reacting the compounds of the formula (VI) with sodium azide.

The conversion to compounds of the formula (XIII) is usually carried out in a solvent, preference being given to carrying out the reaction in a solvent selected from customary solvents that are inert under the prevailing reaction conditions. Preference is given to ethers such as, for example, tetrahydrofuran, ethylene glycol dimethyl ether, dioxane, aprotic polar solvents such as, for example, N,N-dimethylformamide, N-methylpyrrolidone, dimethyl sulphoxide, or alcohols such as methanol or ethanol.

Step b)

The compounds of the formula (XIX) can be prepared by reducing the intermediates of the formula (XVIII), for example analogously to the processes described in WO2015/002211.

Examples of suitable reducing agents are triphenylphosphine, tributylphosphine, tin(III) chloride and zinc.

The conversion to compounds of the formula (XIX) is generally carried out in a solvent. Preference is given to ethers such as, for example, tetrahydrofuran, ethylene glycol dimethyl ether, dioxane, aliphatic hydrocarbons such as hexane, heptane, aromatic hydrocarbons such as toluene, xylene, halogenated hydrocarbons such as, for example, dichloromethane, chloroform, carbon tetrachloride, 1,2-dichloroethane or chlorobenzene, aprotic polar solvents such as, for example, N,N-dimethylformamide, N-methylpyrrolidone, dimethyl sulphoxide, or alcohols such as methanol or ethanol.

If required, an acid such as, for example, hydrochloric acid or acetic acid may be added to the reaction.

Step c)

The compounds of the formula (XXI) can be prepared by reacting the compounds of the formula (XIX) with a compound of the formula (XX) in the presence of an oxidizing agent.

Compounds of the formula (XX) are either commercially available or can be prepared by known methods.

The conversion to compounds of the formula (XXI) (corresponds to formula I(Q16) where p=0) is generally carried out in a solvent. Preference is given to ethers such as, for example, tetrahydrofuran, methyl tert-butyl ether, dioxane, aliphatic hydrocarbons such as hexane, heptane, aromatic hydrocarbons such as toluene, xylene, halogenated hydrocarbons such as, for example, dichloromethane, chloroform, carbon tetrachloride, 1,2-dichloroethane or chlorobenzene, aprotic polar solvents such as, for example, N,N-dimethylformamide, N-methylpyrrolidone, dimethyl sulphoxide, or alcohols such as methanol or ethanol.

Examples of oxidizing agents are halogenating agents such as N-chlorosuccinimide or hypervalent iodine compounds such as bis(acetato-O)phenyl iodide.

Step d)

The compounds of the formula (XXII) (corresponds to formula I(Q16) where p=1) can be prepared anlogously to the process described in WO2015/002211 by reacting compounds of the formula (XXI) with an oxidizing agent.

Examples of a suitable oxidizing agent are sodium periodate and meta-chloroperbenzoic acid.

Suitable solvents for the oxidation are, for example, halogenated aliphatic hydrocarbons such as, for example, dichloromethane or chloroform, alcohols such as methanol or ethanol, and acetic acid.

Process E

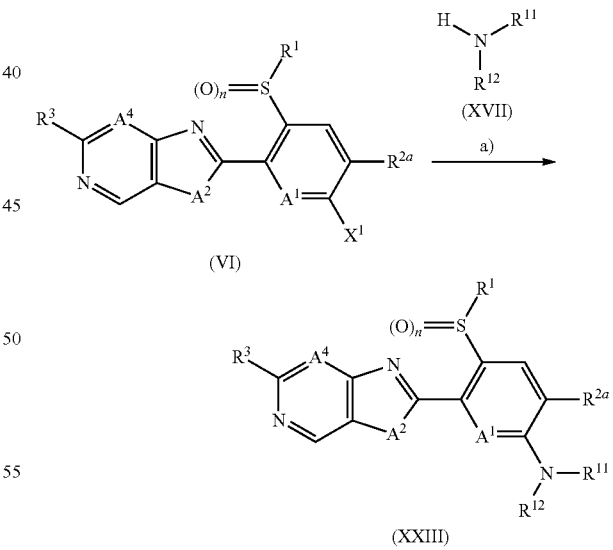

The radicals $R^1$, $R^{2a}$, $R^3$, $R^{11}$, $R^{12}$, $A^1$, $A^2$, $A^4$ and n have the meanings described above and $X^1$ represents halogen.

Step a)

The compounds of the formula (XXIII) can be prepared analogously to WO2015/002211 by reacting the compounds of the formula (VI) with compounds of the formula (XVII).

Compounds of the formula (XVII) are either commercially available or can be prepared by known methods.

The conversion to compounds of the formula (XXIII) (corresponds to formula I(Q10)) is generally carried out in a solvent. Preference is given to ethers such as, for example, tetrahydrofuran, methyl tert-butyl ether, dioxane, ethylene glycol dimethyl ether, aliphatic hydrocarbons such as hexane, heptane, aromatic hydrocarbons such as toluene, xylene, halogenated hydrocarbons such as, for example, dichloromethane, chloroform, carbon tetrachloride, 1,2-dichloroethane or chlorobenzene, aprotic polar solvents such as, for example, N,N-dimethylformamide, N-methylpyrrolidone, dimethyl sulphoxide, or esters such as, for example, ethyl acetate, or nitriles such as acetonitrile.

The reaction can be carried out in the presence of a base. Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; or inorganic bases such as potassium phosphate, potassium carbonate and sodium hydride.

Process F

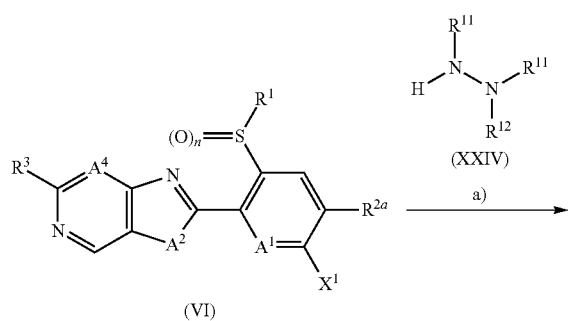

The radicals $R^1$, $R^{2a}$, $R^3$, $R^{11}$, $R^{12}$, $A^1$, $A^2$, $A^4$ and n have the meanings described above and $X^1$ represents halogen.

Step a)

The compounds of the formula (XXV) (corresponds to formula I(Q11)) can be prepared by reacting compounds of the formula (VI) with compounds of the formula (XXIV).

Compounds of the formula (XXIV) are either commercially available or can be prepared by known methods.

The reaction proceeds under reaction conditions analogous to those described in process E.

Process G

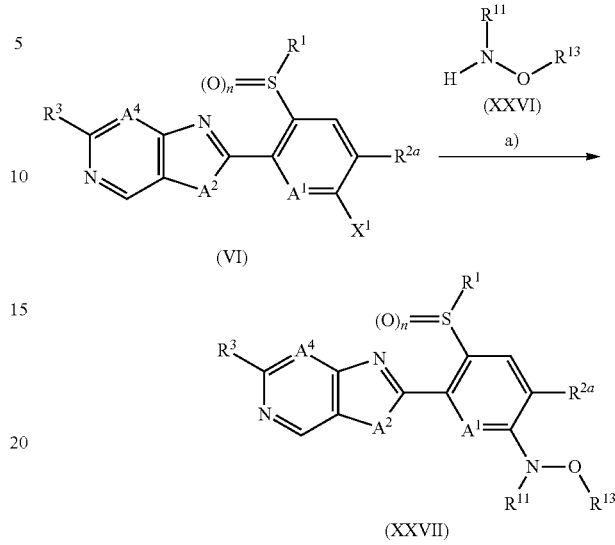

The radicals $R^1$, $R^{2a}$, $R^3$, $R^{11}$, $R^{13}$, $A^1$, $A^2$, $A^4$ and n have the meanings described above and $X^1$ represents halogen.

The compounds of the formula (XXVII) (corresponds to formula I(Q15)) can be prepared by reacting compounds of the formula (VI) with compounds of the formula (XXVI).

Compounds of the formula (XXVI) are either commercially available or can be prepared by known methods.

The reaction proceeds under reaction conditions analogous to those described in process E.

Process H

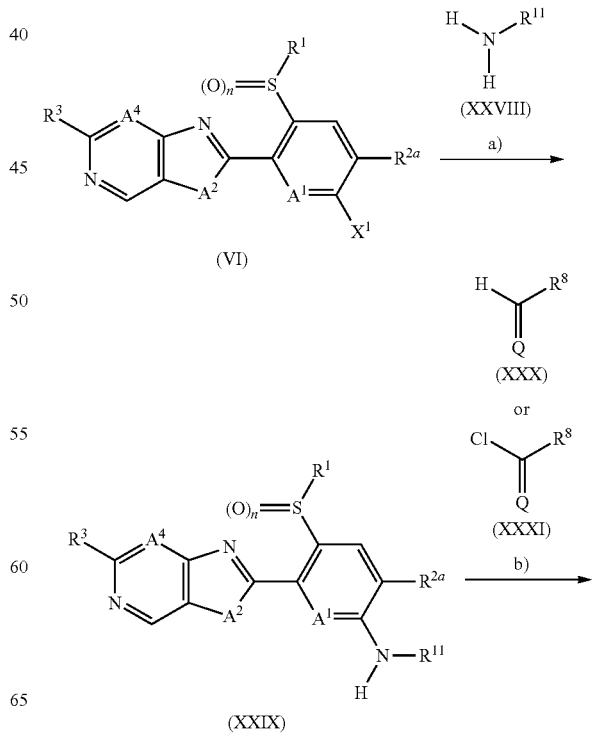

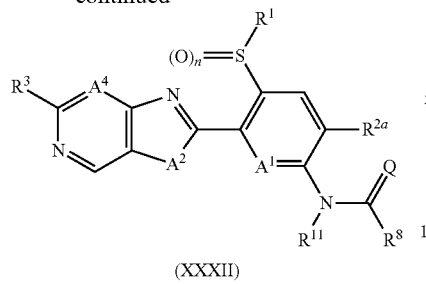

(XXXII)

The radicals $R^1$, $R^{2a}$, $R^3$, $R^{11}$, $A^1$, $A^2$, $A^4$ and n have the meanings described above and $X^1$ represents halogen and Q represents O or S.

Step a)

The compounds of the formula (XXIX) can be prepared by reacting compounds of the formula (VI) with compounds of the formula (XXVIII).

Compounds of the formula (XXVIII) are either commercially available or can be prepared by known methods.

The reaction proceeds under reaction conditions analogous to those described in process E.

Step b)

The compounds of the formula (XXXII) (corresponds to formula I(Q12) where Q=O and I(Q13) where Q=S) can be prepared by reacting compounds of the formula (XXIX) with compounds of the formula (XXX).

Compounds of the formula (XXX) are either commercially available or can be prepared by known methods.

The conversion to compounds of the formula (XXXII) is generally carried out in a solvent. Preference is given to ethers such as, for example, tetrahydrofuran, methyl tert-butyl ether, dioxane, ethylene glycol dimethyl ether, halogenated hydrocarbons such as, for example, dichloromethane, chloroform, carbon tetrachloride, 1,2-dichloroethane or chlorobenzene, aromatic hydrocarbons such as toluene, xylene, esters such as, for example, ethyl acetate, nitriles such as acetonitrile, aprotic polar solvents such as, for example, N,N-dimethylformamide, N-methylpyrrolidone, dimethyl sulphoxide or nitrogenous heterocycles such as pyridine or quinoline.

The reaction can be carried out in the presence of a condensing agent. Examples of suitable condensing agents are carbodiimides such as 1-(3-dimethylaminopropyl)-3-ethylcarbodiimide hydrochloride (EDCI) and 1,3-dicyclohexylcarbodiimide.

The reaction can be carried out in the presence of a suitable catalyst. An example of a suitable catalyst is 1-hydroxybenzotriazole.

The compounds of the formula (XXXII) can also be prepared by reacting compounds of the formula (XXIX) with compounds of the formula (XXXI).

Compounds of the formula (XXXI) are either commercially available or can be prepared by known methods.

The conversion to compounds of the formula (XXXII) is generally carried out in a solvent. Preference is given to ethers such as, for example, tetrahydrofuran, methyl tert-butyl ether, dioxane, ethylene glycol dimethyl ether, aliphatic hydrocarbons such as hexane, heptane, aromatic hydrocarbons such as toluene, xylene, halogenated hydrocarbons such as, for example, dichloromethane, chloroform, carbon tetrachloride, 1,2-dichloroethane or chlorobenzene, aprotic polar solvents such as, for example, N,N-dimethylformamide, N-methylpyrrolidone, dimethyl sulphoxide, or esters such as, for example, ethyl acetate, or nitriles such as acetonitrile.

The reaction can be carried out in the presence of a base. Examples of suitable bases are nitrogen heterocycles such as pyridine, dimethylaminopyridine, picoline, 2,6-lutidine, 1,8-diazabicyclo[5.4.0]-7-undecene (DBU); tertiary amines such as triethylamine and N,N-diisopropylethylamine; or inorganic bases such as potassium carbonate and sodium hydride.

Process I

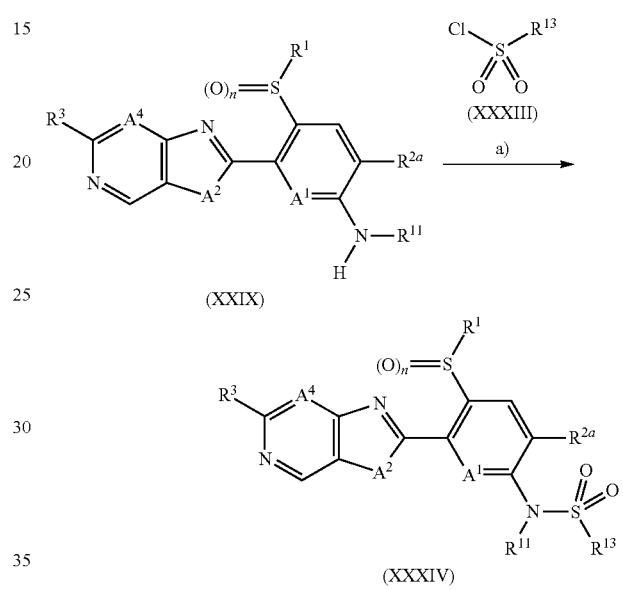

The radicals $R^1$, $R^2$, $R^3$, $R^{11}$, $R^{13}$, $A^1$, $A^2$, $A^4$ and n have the meanings described above.

Step a)

The compounds of the formula (XXXIV) (corresponds to formula I(Q14)) can be prepared by reacting compounds of the formula (XXIX) with compounds of the formula (XXXIII).

Compounds of the formula (XXXIII) are either commercially available or can be prepared by known methods.

The conversion to compounds of the formula (XXXIV) is generally carried out in a solvent. Preference is given to ethers such as, for example, tetrahydrofuran, methyl tert-butyl ether, dioxane, ethylene glycol dimethyl ether, aliphatic hydrocarbons such as hexane, heptane, aromatic hydrocarbons such as toluene, xylene, halogenated hydrocarbons such as, for example, dichloromethane, chloroform, carbon tetrachloride, 1,2-dichloroethane or chlorobenzene, esters such as, for example, ethyl acetate, nitriles such as acetonitrile or aprotic polar solvents such as, for example, N,N-dimethylformamide, N-methylpyrrolidone, dimethyl sulphoxide.

The reaction can be carried out in the presence of a base. Examples of suitable bases are nitrogen heterocycles such as pyridine, dimethylaminopyridine, picoline, 2,6-lutidine, 1,8-diazabicyclo[5.4.0]-7-undecene (DBU); tertiary amines such as triethylamine and N,N-diisopropylethylamine; or inorganic bases such as potassium carbonate and sodium hydride.

Process J

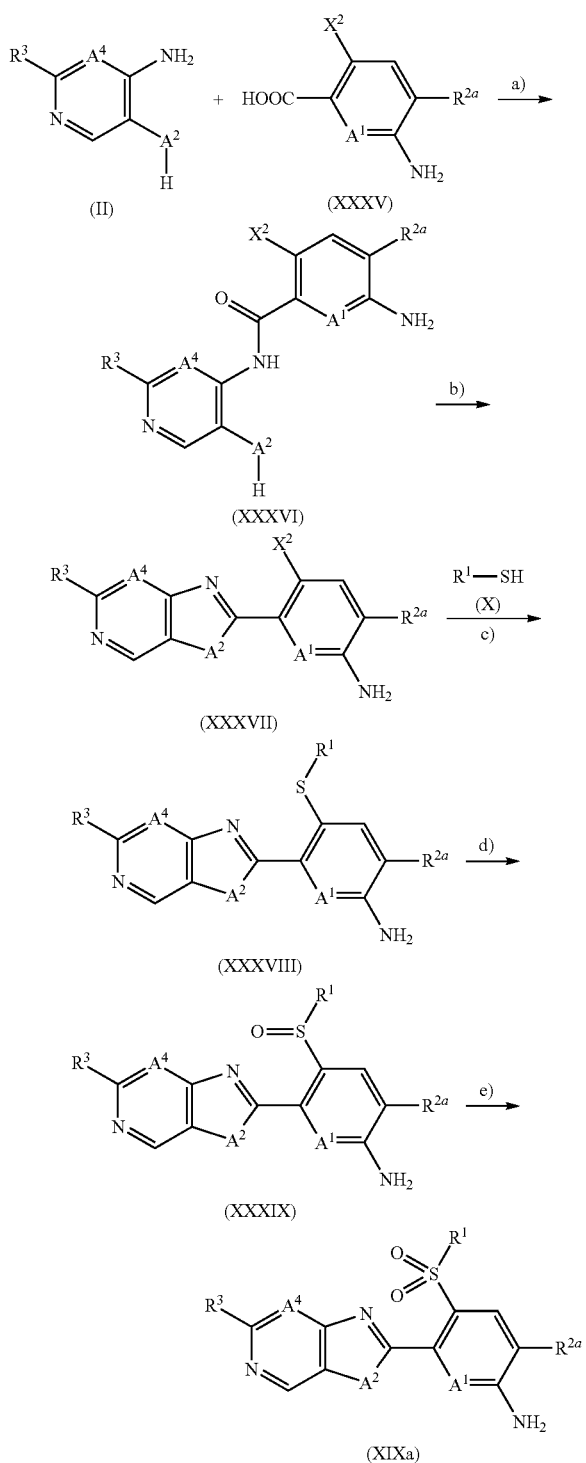

The radicals $R^1$, $R^{2a}$, $R^3$, $A^1$, $A^2$ and $A^4$ have the meanings described above and $X^2$ represents halogen.

Step a)

The compounds of the formula (XXXVI) can be prepared in analogy to the process described in U.S. Pat. No. 5,576,335 by the reaction of compounds of the formula (II) with a carboxylic acid of the formula (XXXV) in the presence of a condensing agent or a base.

Compounds of the formula (II) are either commercially available or can be prepared by known methods, for example analogously to the processes described in US2003/69257 or WO2006/65703.

Carboxylic acids of the formula (XXXV) are either commercially available or can be prepared by known methods, for example analogously to the processes described in US2010/234604, WO2012/61926 or Bioorganic and Medicinal Chemistry Letters, 18 (2008), 5023-5026.

The reaction of the compounds of the formula (II) with carboxylic acids of the formula (XXXV) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate.

The reaction can be carried out under reduced pressure, at atmospheric pressure or under elevated pressure and at temperatures of 0 to 180° C.; with preference, the reaction is carried out at atmospheric pressure and temperatures of 20 to 140° C.

Step b)

The compounds of the formula (XXXVII) can be prepared by condensing the compounds of the formula (XXXVI), for example analogously to the processes described in WO2012/86848.

The conversion to compounds of the formula (XXXVII) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be carried out under reduced pressure, at atmospheric pressure or under elevated pressure, and at temperatures of 0° C. to 200° C.

Step c)

The compounds of the formula (XXXVIII) can be prepared by reacting the compounds of the formula (XXXVII) with the compounds of the formula (X) in the presence of a base.

Mercaptan derivatives of the formula (X), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formula (XXXVIII) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given to caesium carbonate, sodium carbonate and potassium carbonate. Further suitable bases are alkali metal hydrides, for example sodium hydride.

The reaction can be carried out under reduced pressure, at atmospheric pressure or under elevated pressure, and at temperatures of 0° C. to 200° C.

Step d)

The compounds of the formula (XXXIX) can be prepared by oxidizing the compounds of the formula (XXXVIII). The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be carried out under reduced pressure, at atmospheric pressure or under elevated pressure, and at temperatures of −20° C. to 120° C.

Step e)

The compounds of the formula (XIXa) can be prepared by oxidizing the compounds of the formula (XXXIX). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of −20° C. to 120° C.

The further reaction of the compounds of the formulae (XIXa), (XXXVIII) and (XXXIX) is carried out analogously to processes D, H and I.

Process K

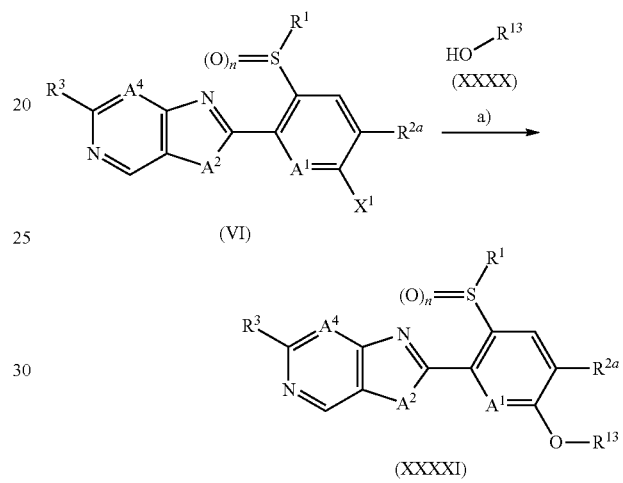

The radicals $R^1$, $R^{2a}$, $R^3$, $R^{13}$, $A^1$, $A^2$, $A^4$ and n have the meanings described above and $X^1$ represents halogen.

Step a)

The compounds of the formula (XXXXI) (corresponds to formula I(Q17)) can be prepared by reacting compounds of the formula (VI) with compounds of the formula (XXXX), for example analogously to the process described in U.S. Pat. No. 4,558,134 or US2014/275026.

Compounds of the formula (XXXX) are either commercially available or can be prepared by known methods.

The conversion to compounds of the formula (XXXXI) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given here to caesium carbonate, sodium carbonate, potassium carbonate and potassium tert-butoxide. Further suitable bases are alkali metal hydrides, for example sodium hydride.

The reaction can be carried out under reduced pressure, at atmospheric pressure or under elevated pressure, and at temperatures of 0° C. to 200° C.

Process L

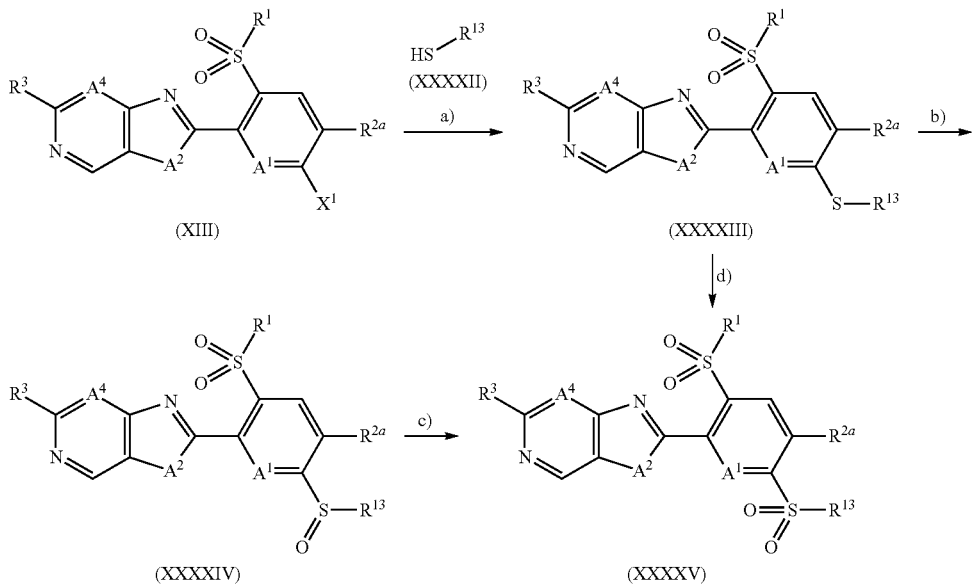

The radicals $R^1$, $R^{2a}$, $R^3$, $R^{13}$, $A^1$, $A^2$ and $A^4$ have the meanings described above and $X^1$ represents halogen.

Step a)

The compounds of the formula (XXXXIII) (corresponds to formula I(Q5) where m=0) can be prepared by reacting compounds of the formula (XIII) with compounds of the formula (XXXXII).

Compounds of the formula (XXXXII) are either commercially available or can be prepared by known methods.

The conversion to compounds of the formula (XXXXIII) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given here to caesium carbonate, sodium carbonate, potassium carbonate and potassium tert-butoxide. Further suitable bases are alkali metal hydrides, for example sodium hydride.

The reaction can be carried out under reduced pressure, at atmospheric pressure or under elevated pressure, and at temperatures of 0° C. to 200° C.

Step b)

The compounds of the formula (XXXXIV) (corresponds to formula I(Q5) where m=1) can be prepared by oxidizing the compounds of the formula (XXXXIII). The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be carried out under reduced pressure, at atmospheric pressure or under elevated pressure, and at temperatures of −20° C. to 120° C.

Step c)

The compounds of the formula (XXXXV) (corresponds to formula I(Q5) where m=2) can be prepared by oxidizing the compounds of the formula (XXXXIV). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of −20° C. to 120° C.

Step d)

The compounds of the formula (XXXXV) can also be prepared in a one-step process by oxidizing the compounds of the formula (XXXXIII). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of −20° C. to 120° C.

Process M

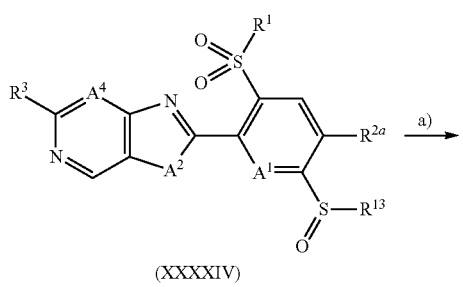

(XXXXIV)

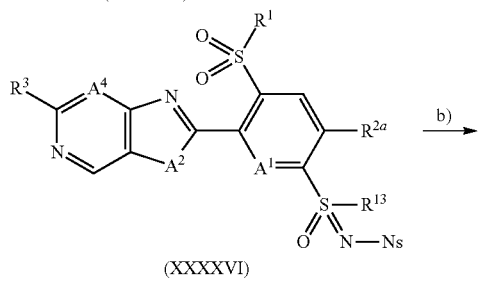

(XXXXVI)

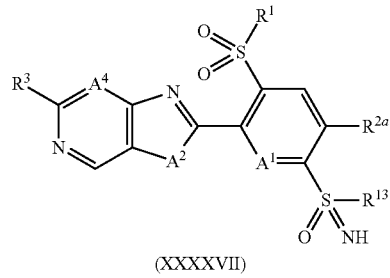

(XXXXVII)

The radicals $R^1$, $R^{2a}$, $R^3$, $R^{13}$, $A^1$, $A^2$ and $A^4$ have the meanings described above. Ns=nosyl/4-nitrobenzylsulphonyl Step a)

The compounds of the formula (XXXXVI) can be prepared by imination of the compounds of the formula (XXXXIV) with 4-nitrobenzylsulphonylamide ($NsNH_2$) and a hypervalent iodine compound with metal catalysis, for example analogously to the processes described in Organic Letters 2006, 8, 2349 und Chemistry—A European Journal 2007, 13, 6674.

The reaction of the compounds of the formula (XXXXVI) is preferably carried out in a solvent selected from customary solvents which are inert under the prevailing reaction conditions. Preference is given to nitriles such as, for example, acetonitrile, or to halogenated alkanes such as, for example, dichloromethane.

Examples of metal catalysts are iron, copper, silver or rhodium compounds, for example iron(II) acetylacetonate, iron(III) acetylacetonate and rhodium(II) acetate. Diacetoxyiodobenzene or iodosylbenzene are frequently used as hypervalent iodine compounds.

The reaction can be carried out under reduced pressure, at atmospheric pressure or under elevated pressure, and at room temperature.

Step b)

The compounds of the formula (XXXXVII) (corresponds to formula I(Q6)) can be prepared from compounds of the formula (XXXXVI) by reaction with a thiol under basic conditions, for example analogously to the processes described in Organic Letters 2006, 8, 2349; Chemistry—A European Journal 2007, 13, 6674 and WO2006/101860.

The conversion to compounds of the formula (XXXXVII) is generally carried out in a solvent.

Preference is given to ethers such as, for example, tetrahydrofuran, or nitriles such as acetonitrile.

The thiol used is, for example, thiophenol in combination with an inorganic base from the group consisting of carbonates of alkali or alkaline earth metals, for example caesium carbonate. The use of a solution of sodium thiomethoxide in methanol has also been described.

The reaction can be carried out under reduced pressure, at atmospheric pressure or under elevated pressure, and at temperatures of −78° C. to 30° C.

Process N

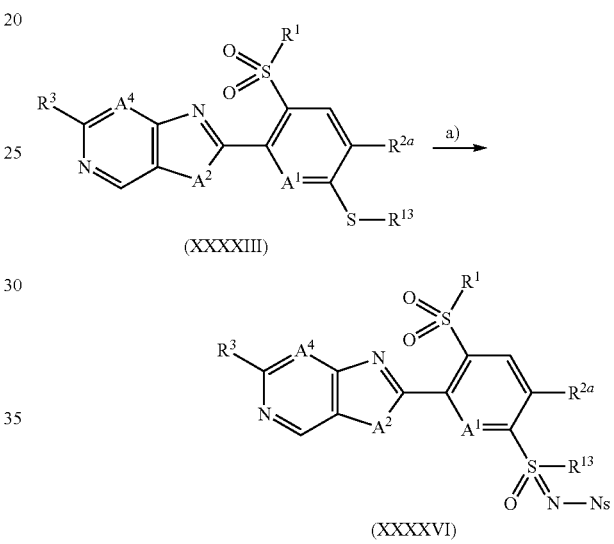

(XXXXIII)

(XXXXVI)

The radicals $R^1$, $R^{2a}$, $R^3$, $R^{13}$, $A^1$, $A^2$ and $A^4$ have the meanings described above. Ns=nosyl/4-nitrobenzylsulphonyl.

Step a)

The compounds of the formula (XXXXVI) can be prepared by reacting compounds of the formula (XXXXIII) analogously to the processes described in process M, step a).

The further conversion of compounds of the formula (XXXXVI) to compounds of the formula (XXXXVII) proceeds under reaction conditions analogous to those described in process M.

Process O

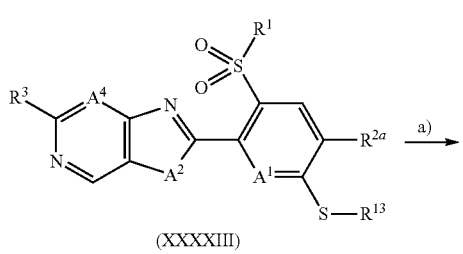

(XXXXIII)

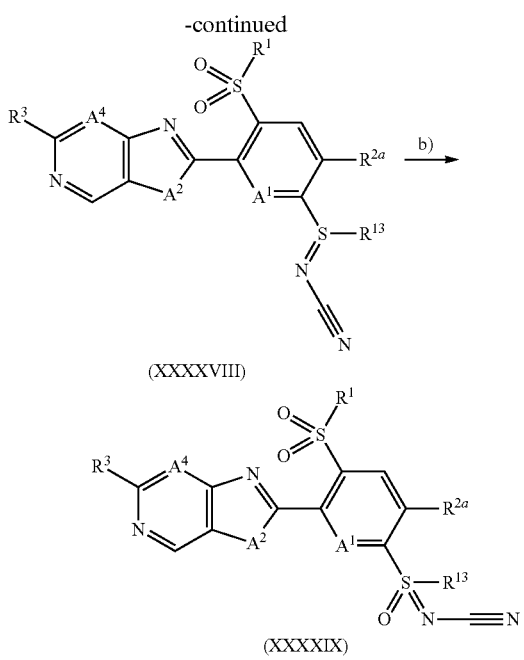

(XXXXVIII)

(XXXXIX)

The radicals $R^1$, $R^{2a}$, $R^3$, $R^{13}$, $A^1$, $A^2$ and $A^4$ have the meanings described above.

Step a)

The compounds of the formula (XXXXVIII) (corresponds to formula I(Q8)) can be prepared from compounds of the formula (XXXXIII) by imination with cyanamide in the presence of a hypervalent iodine compound, for example analogously to the processes described in Organic Letters 2007, 9, 2951. The conversion to compounds of the formula (XXXXVIII) is generally carried out in acetonitrile as solvent. Diacetoxyiodobenzene or iodosylbenzene are frequently used as hypervalent iodine compounds. The reaction can be carried out under reduced pressure, at atmospheric pressure or under elevated pressure, and at temperatures of 0° C. to 30° C.

The compounds of the formula (XXXXVIII) can furthermore be prepared from compounds of the formula (XXXXIII) by imination with cyanamide in the presence of N-bromosuccinimide (NBS) or iodine under basic conditions, for example analogously to the processes described in Organic Letters 2007, 9, 3809 or WO2014/29830. In this case, the conversion to compounds of the formula (XXXXVIII) is carried out in a solvent. Preference is given to using alcohols such as, for example, methanol, ethers such as, for example, tetrahydrofuran, or nitriles such as acetonitrile. Examples of suitable bases are alkoxides such as, for example, potassium tert-butoxide. Further suitable bases are alkali metal hydrides, for example sodium hydride. The reaction can be carried out under reduced pressure, at atmospheric pressure or under elevated pressure, and at room temperature.

Step b)

The compounds of the formula (XXXXIX) (corresponds to formula I(Q7)) can be prepared from compounds of the formula (XXXXVIII) by oxidation under basic conditions, for example analogously to the processes described in Organic Letters 2007, 9, 2951; Organic Letters 2007, 9, 3809 or WO2014/140075. The oxidation is generally carried out in a solvent. Preference is given to alcohols such as ethanol. The oxidizing agent used is, for example, meta-chloroperbenzoic acid. Examples of suitable bases are carbonates such as, for example, potassium carbonate. The reaction can be carried out under reduced pressure, at atmospheric pressure or under elevated pressure, and at temperatures of 0° C. to 30° C.

Process P

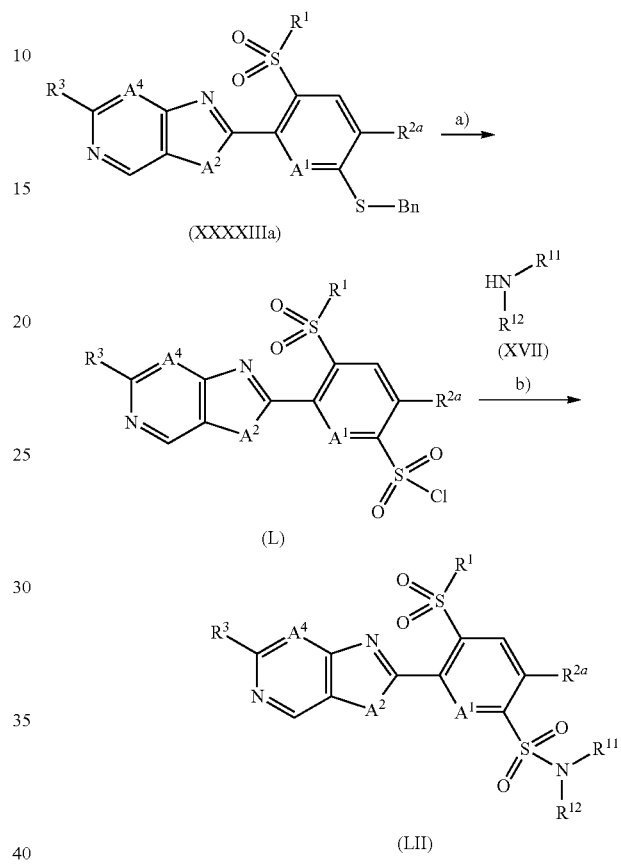

(XXXXIIIa)

(L)

(LII)

The radicals $R^1$, $R^{2a}$, $R^3$, $R^{11}$, $R^{12}$, $A^1$, $A^2$ and $A^4$ have the meanings described above. Bn=benzyl/CH$_2$Ph.

Step a)

The compounds of the formula (L) can be prepared from intermediates of the formula (XXXXIIIa) by oxidation in the presence of a chlorine source, for example analogously to the processes described in WO2008/2244 and WO2010/24451.

The conversion to compounds of the formula (L) is generally carried out in a solvent. Preference is given to halogenated alkanes such as, for example, dichloromethane or tetrachloromethane. Frequently, mixtures with water are employed.

The chlorine sources and oxidizing agents used are, for example, chlorine gas, N-chlorosuccinimide or 1,3-dichloro-5,5-dimethylhydantoin.

Frequently, the reactions are carried out in an acidic medium. Acids used are, for example, carboxylic acids such as formic acid or acetic acid.

The reaction can be carried out under reduced pressure, at atmospheric pressure or under elevated pressure, and at temperatures of 0° C. to 30° C.

Step b)

The compounds of the formula (LII) (corresponds to formula I(Q9)) can be prepared from compounds of the formula (L) with compounds of the formula (XVII) under standard conditions.

The conversion to compounds of the formula (LII) is generally carried out in a solvent. Preference is given to ethers such as, for example, tetrahydrofuran, methyl tert-butyl ether, dioxane, ethylene glycol dimethyl ether, aliphatic hydrocarbons such as hexane, heptane, aromatic hydrocarbons such as toluene, xylene, halogenated hydrocarbons such as, for example, dichloromethane, chloroform, carbon tetrachloride, 1,2-dichloroethane or chlorobenzene, esters such as, for example, ethyl acetate, nitriles such as acetonitrile or aprotic polar solvents such as, for example, N,N-dimethylformamide, N-methylpyrrolidone, dimethyl sulphoxide.

The reaction can be carried out in the presence of a base. Examples of suitable bases are nitrogen heterocycles such as pyridine, dimethylaminopyridine, picoline, 2,6-lutidine, 1,8-diazabicyclo[5.4.0]-7-undecene (DBU); tertiary amines such as triethylamine and N,N-diisopropylethylamine; or inorganic bases such as potassium carbonate and sodium hydride.

Process Q

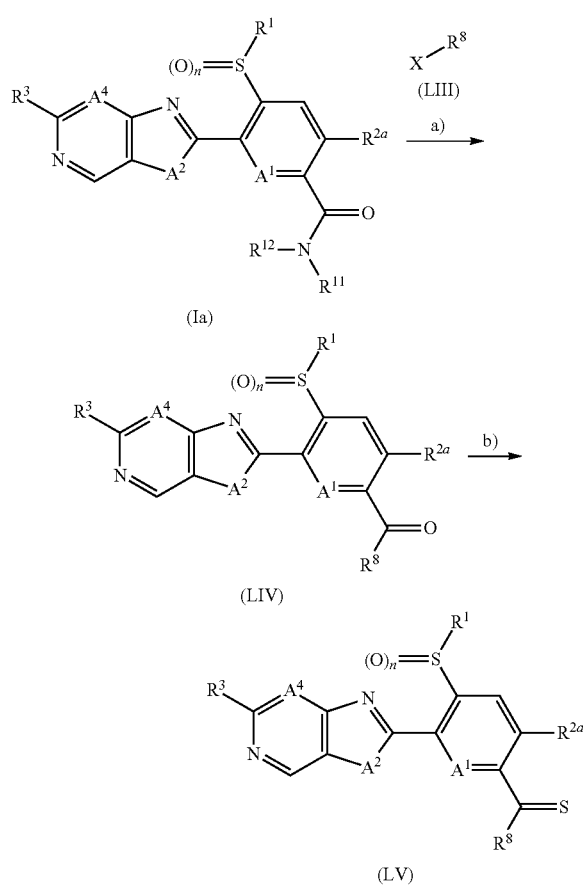

The radicals $R^1$, $R^{2a}$, $R^3$, $R^8$, $A^1$, $A^2$, $A^4$ and n have the meanings described above, $R^{11}$ represents methyl, $R^{12}$ represents methoxy and X represents halogen.

Step a)

The compounds of the formula (LIV) (corresponds to formula I(Q1)) can be prepared by conventing compounds of the formula (LIII) into an organometallic compound and subsequent reaction with compounds of the formula (Ia), for example analogously to the processes described in U.S. Pat. No. 5,821,246 and European Journal of Medicinal Chemistry 2012, 58, p. 396.

Compounds of the formula (LIII) are either commercially available or can be prepared by known methods.

The organometal compounds can be produced, for example, from compounds of the formula (LIII) by reaction with magnesium or alkyllithium compounds.

The conversion to compounds of the formula (LV) is generally carried out in a solvent. Preference is given to ethers such as tetrahydrofuran or diethyl ether.

The reaction can be carried out under reduced pressure, at atmospheric pressure or under elevated pressure, and at temperatures of −78° C. to 45° C.

Step b)

Thioketones of the formula (LV) (corresponds to formula I(Q2)) can be prepared from compounds of the formula (LIV) by reaction with a sulphurizing agent, for example Lawesson's reagent or $P_4S_{10}$.

Process R

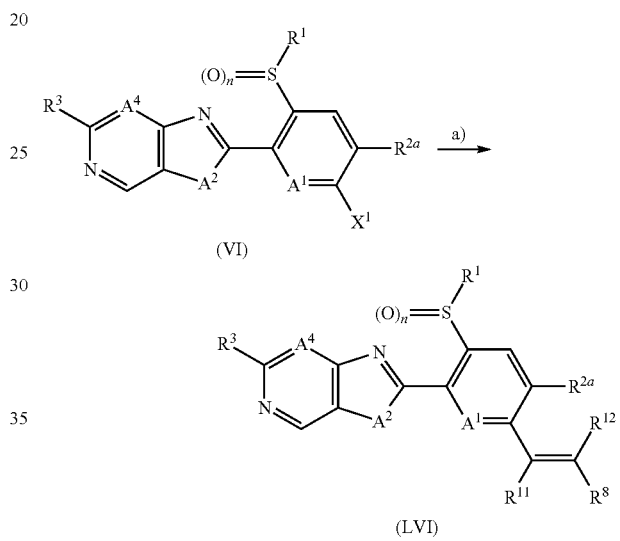

The radicals $R^1$, $R^{2a}$, $R^3$, $R^8$, $R^{11}$, $R^{12}$, $A^1$, $A^2$, $A^4$ and n have the meanings described above and $X^1$ represents halogen.

Compounds of the formula (LVI) can be prepared, for example, from compounds of the formula (VI) in which $X^1$ preferably represents halogen from the group consisting of chlorine or bromine, by generally known methods (cf. Chem. Rev. 1995, 95, 2457-2483; Tetrahedron 2002, 58, 9633-9695; Metal-Catalyzed Cross-Coupling Reactions (eds.: A. de Meijere, F. Diederich), $2^{nd}$ ed., Wiley-VCH, Weinheim, 2004).

For example, compounds of the formula (VI) can be reacted with suitable olefinic boronic acids or esters thereof by known methods (cf. WO2006/21805) in the presence of suitable catalysts from the group of the transition metal salts to give compounds of the formula (LVI). Examples of preferred coupling catalysts include palladium catalysts such as [1,1'-bis(diphenylphosphino)ferrocene]dichloropalladium(II) or tetrakis(triphenylphosphine)palladium. Suitable basic reaction auxiliaries used to conduct the processes are preferably carbonates of sodium or potassium.

Some of the olefinic boronic acids or olefinic boronic esters required are known and/or commercially available, or they can be prepared by generally known methods (cf. Boronic Acids (eds.: D. G. Hall), $2^{nd}$ ed., Wiley-VCH, Weinheim, 2011).

The invention also provides compounds of the formula (IX)

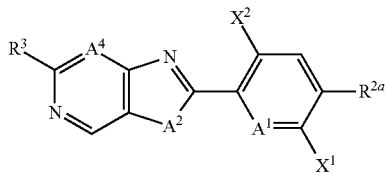

in which
$R^{2a}$, $R^3$, $A^1$, $A^2$ and $A^4$ have the meanings described above and $X^1$ and $X^2$ represent halogen (preferably fluorine, chlorine, bromine, iodine, particularly preferably chlorine or fluorine).

Preference is given to compounds of the formula (IX) in which $A^1$ represents nitrogen, $A^2$ represents N-methyl, $A^4$ represents CH, $X^1$ represents halogen, $X^2$ represents halogen and
$R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

Particular preference is given to compounds of the formula (IX) in which $A^1$ represents nitrogen, $A^2$ represents N-methyl, $A^4$ represents CH, $X^1$ represents chlorine or fluorine, $X^2$ represents chlorine or fluorine and
$R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

The invention also provides compounds of the formula (XI)

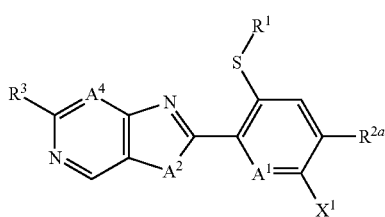

in which
$R^1$, $R^{2a}$, $R^3$, $A^1$, $A^2$ and $A^4$ have the meanings described above and $X^1$ represents halogen (preferably fluorine, chlorine, bromine, iodine, particularly preferably chlorine or fluorine).

Preference is given to compounds of the formula (XI) in which $A^1$ represents nitrogen, $A^2$ represents N-methyl, $A^4$ represents CH, $X^1$ represents halogen and
$R^1$, $R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

Particular preference is given to compounds of the formula (XI) in which $A^1$ represents nitrogen, $A^2$ represents N-methyl, $A^4$ represents CH, $X^1$ represents chlorine or fluorine and
$R^1$, $R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

The invention also provides compounds of the formula (XII)

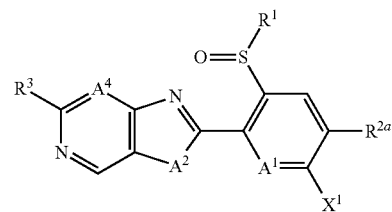

in which
$R^1$, $R^{2a}$, $R^3$, $A^1$, $A^2$ and $A^4$ have the meanings described above and $X^1$ represents halogen (preferably fluorine, chlorine, bromine, iodine, particularly preferably chlorine or fluorine).

Preference is given to compounds of the formula (XII) in which $A^1$ represents nitrogen, $A^2$ represents N-methyl, $A^4$ represents CH, $X^1$ represents halogen and
$R^1$, $R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

Particular preference is given to compounds of the formula (XII) in which $A^1$ represents nitrogen, $A^2$ represents N-methyl, $A^4$ represents CH, $X^1$ represents chlorine or fluorine and
$R^1$, $R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

The invention also provides compounds of the formula (XIII)

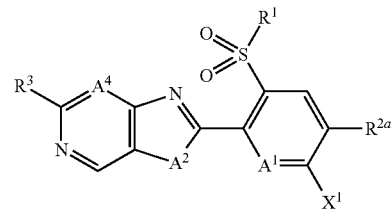

in which
$R^1$, $R^{2a}$, $R^3$, $A^1$, $A^2$ and $A^4$ have the meanings described above and $X^1$ represents halogen (preferably fluorine, chlorine, bromine, iodine, particularly preferably chlorine or fluorine).

Preference is given to compounds of the formula (XIII) in which $A^1$ represents nitrogen, $A^2$ represents N-methyl, $A^4$ represents CH, $X^1$ represents halogen and
$R^1$, $R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

Particular preference is given to compounds of the formula (XIII) in which $A^1$ represents nitrogen, $A^2$ represents N-methyl, $A^4$ represents CH, $X^1$ represents chlorine or fluorine and $R^1$, $R^{2a}$ and $R^3$ have the meanings described in configuration (1) or configuration (1-1) or configuration (1-2) or configuration (2) or configuration (2-1) or configuration (2-2) or configuration (3) or configuration (3-1) or configuration (3-2) or configuration (4) or configuration (4-1) or configuration (4-2) or configuration (5-2a) or configuration (5-2b).

Methods and Uses

The invention also relates to methods for controlling animal pests, in which compounds of the formula (I) are allowed to act on animal pests and/or their habitat. The control of the animal pests is preferably carried out in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and also against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes* pyri, *Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*; from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus* (=*Hyperodes*) spp., *Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus* hololeucus, Oryctes rhinoceros, Oryzaephilus surinamensis, Oryzaphagus oryzae, Otiorhynchus spp., for example Otiorhynchus cribricollis, Otiorhynchus ligustici, Otiorhynchus ovatus, Otiorhynchus rugosostriarus, Otiorhynchus sulcatus, Oulema spp., Oulema oryzae, Oxycetonia jucunda, Phaedon cochleariae, Phyllophaga spp., Phyllophaga helleri, Phyllotreta spp., for example Phyllotreta armoraciae, Phyllotreta pusilla, Phyllotreta ramosa, Phyllotreta striolata, Popillia japonica, Premnotrypes spp., Prostephanus truncatus, Psylliodes spp., for example Psylliodes affinis, Psylliodes chrysocephala, Psylliodes punctulata, Ptinus spp., Rhizobius ventralis, Rhizopertha dominica, Rhynchophorus spp., Rhynchophorus ferrugineus, Rhynchophorus palmarum, Sinoxylon perforans, Sitophilus spp., for example Sitophilus granarius, Sitophilus linearis, Sitophilus oryzae, Sitophilus zeamais, Sphenophorus spp., Stegobium paniceum, Stemechus spp., for example Stemechus paludatus, Symphyletes spp., Tanymecus spp., for example Tanymecus dilaticollis, Tanymecus indicus, Tanymecus palliatus, Tenebrio molitor, Tenebrioides mauretanicus, Tribolium spp., for example Tribolium audax, Tribolium castaneum, Tribolium confusum, Trogoderma spp., Tychius spp., Xylotrechus spp., Zabrus spp., for example Zabrus tenebrioides;

from the order of the Dermaptera, for example Anisolabis maritime, Forficula auricularia, Labidura riparia;

from the order of the Diptera, for example Aedes spp., for example Aedes aegypti, Aedes albopictus, Aedes sticticus, Aedes vexans, Agromyza spp., for example Agromyza frontella, Agromyza parvicornis, Anastrepha spp., Anopheles spp., for example Anopheles quadrimaculatus, Anopheles gambiae, Asphondylia spp., Bactrocera spp., for example Bactrocera cucurbitae, Bactrocera dorsalis, Bactrocera oleae, Bibio hortulanus, Calliphora erythrocephala, Calliphora vicina, Ceratitis capitata, Chironomus spp., Chrysomya spp., Chrysops spp., Chrysozona pluvialis, Cochliomya spp., Contarinia spp., for example Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex spp., for example Culex pipiens, Culex quinquefasciatus, Culicoides spp., Culiseta spp., Cuterebra spp., Dacus oleae, Dasineura spp., for example Dasineura brassicae, Delia spp., for example Delia antiqua, Delia coarctata, Delia florilega, Delia platura, Delia radicum, Dermatobia hominis, Drosophila spp., for example Drosphila melanogaster, Drosophila suzukii, Echinocnemus spp., Euleia heraclei, Fannia spp., Gasterophilus spp., Glossina spp., Haematopota spp., Hydrellia spp., Hydrellia griseola, Hylemya spp., Hippobosca spp., Hypoderma spp., Liriomyza spp., for example Liriomyza brassicae, Liriomyza huidobrensis, Liriomyza sativae, Lucilia spp., for example Lucilia cuprina, Lutzomyia spp., Mansonia spp., Musca spp., for example Musca domestica, Musca domestica vicina, Oestrus spp., Oscinella frit, Paratanytarsus spp., Paralauterbomiella subcincta, Pegomya spp., for example Pegomya betae, Pegomya hyoscyami, Pegomya rubivora, Phlebotomus spp., Phorbia spp., Phormia spp., Piophila casei, Platyparea poeciloptera, Prodiplosis spp., Psila rosae, Rhagoletis spp., for example Rhagoletis cingulata, Rhagoletis completa, Rhagoletis fausta, Rhagoletis indifferens, Rhagoletis mendax, Rhagoletis pomonella, Sarcophaga spp., Simulium spp., for example Simulium meridionale, Stomoxys spp., Tabanus spp., Tetanops spp., Tipula spp., for example Tipula paludosa, Tipula simplex, Toxotrypana curvicauda;

from the order of the Hemiptera, for example Acizzia acaciaebaileyaneae, Acizzia dodonaeae, Acizzia uncatoides, Acrida turrita, Acyrthosipon spp., for example Acyrthosiphon pisum, Acrogonia spp., Aeneolamia spp., Agonoscena spp., Aleurocanthus spp., Aleyrodes proletella, Aleurolobus barodensis, Aleurothrixus floccosus, Allocaridara malayensis, Amrasca spp., for example Amrasca bigutulla, Amrasca devastans, Anuraphis cardui, Aonidiella spp., for example Aonidiella aurantii, Aonidiella citrina, Aonidiella inomata, Aphanostigma piri, Aphis spp., for example Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis vibumiphila, Arboridia apicalis, Arytainilla spp., Aspidiella spp., Aspidiotus spp., for example Aspidiotus nerii, Atanus spp., Aulacorthum solani, Bemisia tabaci, Blastopsylla occidentalis, Boreioglycaspis melaleucae, Brachycaudus helichrysi, Brachycolus spp., Brevicoryne brassicae, Cacopsylla spp., for example Cacopsylla pyricola, Calligypona marginata, Capulinia spp., Carneocephala fulgida, Ceratovacuna lanigera, Cercopidae, Ceroplastes spp., Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus spp., for example Coccus hesperidum, Coccus longulus, Coccus pseudomagnoliarum, Coccus viridis, Cryptomyzus ribis, Cryptoneossa spp., Ctenarytaina spp., Dalbulus spp., Dialeurodes chittendeni, Dialeurodes citri, Diaphorina citri, Diaspis spp., Diuraphis spp., Drosicha spp., Dysaphis spp., for example Dysaphis apiifolia, Dysaphis plantaginea, Dysaphis tulipae, Dysmicoccus spp., Empoasca spp., for example Empoasca abrupta, Empoasca fabae, Empoasca maligna, Empoasca solana, Empoasca stevensi, Eriosoma spp., for example Eriosoma americanum, Eriosoma lanigerum, Eriosoma pyricola, Erythroneura spp., Eucalyptolyma spp., Euphyllura spp., Euscelis bilobatus, Ferrisia spp., Fiorinia spp., Furcaspis oceanica, Geococcus coffeae, Glycaspis spp., Heteropsylla cubana, Heteropsylla spinulosa, Homalodisca coagulata, Hyalopterus arundinis, Hyalopterus pruni, Icerya spp., for example Icerya purchasi, Idiocerus spp., Idioscopus spp., Laodelphax striatellus, Lecanium spp., for example Lecanium corni (=Parthenolecanium comi), Lepidosaphes spp., for example Lepidosaphes ulmi, Lipaphis erysimi, Lopholeucaspis japonica, Lycorma delicatula, Macrosiphum spp., for example Macrosiphum euphorbiae, Macrosiphum lilii, Macrosiphum rosae, Macrosteles facifrons, Mahanarva spp., Melanaphis sacchari, Metcalfiella spp., Metcalfa pruinosa, Metopolophium dirhodum, Monellia costalis, Monelliopsis pecanis, Myzus spp., for example Myzus ascalonicus, Myzus cerasi, Myzus ligustri, Myzus omatus, Myzus persicae, Myzus nicotianae, Nasonovia ribisnigri, Neomaskellia spp., Nephotettix spp., for example Nephotettix cincticeps, Nephotettix nigropictus, Nettigonicla spectra, Nilaparvata lugens, Oncometopia spp., Orthezia praelonga, Oxya chinensis, Pachypsylla spp., Parabemisia myricae, Paratrioza spp., for example Paratrioza cockerelli, Parlatoria spp., Pemphigus spp., for example Pemphigus bursarius, Pemphigus populivenae, Peregrinus maidis, Perkinsiella spp., Phenacoccus spp., for example Phenacoccus madeirensis, Phloeomyzus passerinii, Phorodon humuli, Phylloxera spp., for example Phylloxera devastatrix, Phylloxera notabilis, Pinnaspis aspidistrae, Planococcus spp., for example Planococcus citri, Prosopidopsylla flava, Protopulvinaria pyriformis, Pseudaulacaspis pentagona, Pseudococcus spp., for example Pseudococcus calceolariae, Pseudococcus comstocki, Pseudococcus longispinus, Pseudococcus maritimus, Pseudococcus vibumi, Psyllopsis spp., Psylla spp., for example *Psylla buxi*, *Psylla mali*, *Psylla pyri*, *Pteromalus* spp., *Pulvinaria* spp., *Pyrilla* spp., *Quadraspidiotus* spp., for example *Quadraspidiotus juglansregiae*, *Quadraspidiotus ostreaeformis*, *Quadraspidiotus pemiciosus*, *Quesada gigas*, *Rastrococcus* spp., *Rhopalosiphum* spp., for example *Rhopalosiphum maidis*, *Rhopalosiphum oxyacanthae*, *Rhopalosiphum padi*, *Rhopalosiphum rufiabdominale*, *Saissetia* spp., for example *Saissetia coffeae*, *Saissetia miranda*, *Saissetia neglecta*, *Saissetia oleae*, *Scaphoideus titanus*, *Schizaphis graminum*, *Selenaspidus articulatus*, *Sitobion avenae*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., for example *Toxoptera aurantii*, *Toxoptera citricidus*, *Trialeurodes vaporariorum*, *Trioza* spp., for example *Trioza diospyri*, *Typhlocyba* spp., *Unaspis* spp., *Viteus vitifolii*, *Zygina* spp.; from the suborder of the Heteroptera, for example *Aelia* spp., *Anasa tristis*, *Antestiopsis* spp., *Boisea* spp., *Blissus* spp., *Calocoris* spp., *Campylomma livida*, *Cavelerius* spp., *Cimex* spp., for example *Cimex adjunctus*, *Cimex hemipterus*, *Cimex lectularius*, *Cimex pilosellus*, *Collaria* spp., *Creontiades dilutus*, *Dasynus piperis*, *Dichelops furcatus*, *Diconocoris hewetti*, *Dysdercus* spp., *Euschistus* spp., for example *Euschistus heros*, *Euschistus servus*, *Euschistus tristigmus*, *Euschistus variolarius*, *Eurydema* spp., *Eurygaster* spp., *Halyomorpha halys*, *Heliopeltis* spp., *Horcias nobilellus*, *Leptocorisa* spp., *Leptocorisa varicornis*, *Leptoglossus occidentalis*, *Leptoglossus phyllopus*, *Lygocoris* spp., for example *Lygocoris pabulinus*, *Lygus* spp., for example *Lygus elisus*, *Lygus hesperus*, *Lygus lineolaris*, *Macropes excavatus*, *Megacopta cribraria*, *Miridae*, *Monalonion atratum*, *Nezara* spp., for example *Nezara viridula*, *Nysius* spp., *Oebalus* spp., *Pentomidae*, *Piesma quadrata*, *Piezodorus* spp., for example *Piezodorus guildinii*, *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Hymenoptera, for example *Acromyrmex* spp., *Athalia* spp., for example *Athalia rosae*, *Atta* spp., *Camponotus* spp., *Dolichovespula* spp., *Diprion* spp., for example *Diprion similis*, *Hoplocampa* spp., for example *Hoplocampa cookei*, *Hoplocampa testudinea*, *Lasius* spp., *Linepithema humile*, *Monomorium pharaonis*, *Paratrechina* spp., *Paravespula* spp., *Plagiolepis* spp., *Sirex* spp., *Solenopsis invicta*, *Tapinoma* spp., *Technomyrmex albipes*, *Urocerus* spp., *Vespa* spp., for example *Vespa crabro*, *Wasmannia auropunctata*, *Xeris* spp.;

from the order of the Isopoda, for example *Armadillidium vulgare*, *Oniscus asellus*, *Porcellio scaber*; from the order of the Isoptera, for example *Coptotermes* spp., for example *Coptotermes formosanus*, *Comitermes cumulans*, *Cryptotermes* spp., *Incisitermes* spp., *Kalotermes* spp., *Microtermes obesi*, *Nasutitermes* spp., *Odontotermes* spp., *Porotermes* spp., *Reticulitermes* spp., for example *Reticulitermes flavipes*, *Reticulitermes hesperus*;

from the order of the Lepidoptera, for example *Achroia grisella*, *Acronicta major*, *Adoxophyes* spp., for example *Adoxophyes orana*, *Aedia leucomelas*, *Agrotis* spp., for example *Agrotis segetum*, *Agrotis ipsilon*, *Alabama* spp., for example *Alabama argillacea*, *Amyelois transitella*, *Anarsia* spp., *Anticarsia* spp., for example *Anticarsia gemmatalis*, *Argyroploce* spp., *Autographa* spp., *Barathra brassicae*, *Blastodacna atra*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., for example *Chilo plejadellus*, *Chilo suppressalis*, *Choreutis pariana*, *Choristoneura* spp., *Chrysodeixis chalcites*, *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., for example *Cydia nigricana*, *Cydia pomonella*, *Dalaca noctuides*, *Diaphania* spp., *Diparopsis* spp., *Diatraea saccharalis*, *Earias* spp., *Ecdytolopha aurantium*, *Elasmopalpus lignosellus*, *Eldana saccharina*, *Ephestia* spp., for example *Ephestia elutella*, *Ephestia kuehniella*, *Epinotia* spp., *Epiphyas postvittana*, *Erannis* spp., *Erschoviella musculana*, *Etiella* spp., *Eudocima* spp., *Eulia* spp., *Eupoecilia ambiguella*, *Euproctis* spp., for example *Euproctis chrysorrhoea*, *Euxoa* spp., *Feltia* spp., *Galleria mellonella*, *Gracillaria* spp., *Grapholitha* spp., for example *Grapholita molesta*, *Grapholita prunivora*, *Hedylepta* spp., *Helicoverpa* spp., for example *Helicoverpa armigera*, *Helicoverpa zea*, *Heliothis* spp., for example *Heliothis virescens*, *Hofmannophila pseudospretella*, *Homoeosoma* spp., *Homona* spp., *Hyponomeuta padella*, *Kakivoria flavofasciata*, *Lampides* spp., *Laphygma* spp., *Laspeyresia molesta*, *Leucinodes orbonalis*, *Leucoptera* spp., for example *Leucoptera coffeella*, *Lithocolletis* spp., for example *Lithocolletis blancardella*, *Lithophane antennata*, *Lobesia* spp., for example *Lobesia botrana*, *Loxagrotis albicosta*, *Lymantria* spp., for example *Lymantria dispar*, *Lyonetia* spp., for example *Lyonetia clerkella*, *Malacosoma neustria*, *Maruca testulalis*, *Mamestra brassicae*, *Melanitis leda*, *Mocis* spp., *Monopis obviella*, *Mythimna separata*, *Nemapogon cloacellus*, *Nymphula* spp., *Oiketicus* spp., *Omphisa* spp., *Operophtera* spp., *Oria* spp., *Orthaga* spp., *Ostrinia* spp., for example *Ostrinia nubilalis*, *Oulema melanopus*, *Oulema oryzae*, *Panolis flammea*, *Parnara* spp., *Pectinophora* spp., for example *Pectinophora gossypiella*, *Perileucoptera* spp., *Phthorimaea* spp., for example *Phthorimaea operculella*, *Phyllocnistis citrella*, *Phyllonorycter* spp., for example *Phyllonorycter blancardella*, *Phyllonorycter crataegella*, *Pieris* spp., for example *Pieris rapae*, *Platynota stultana*, *Plodia interpunctella*, *Plusia* spp., *Plutella xylostella* (=*Plutella maculipennis*), *Prays* spp., *Prodenia* spp., *Protoparce* spp., *Pseudaletia* spp., for example *Pseudaletia unipuncta*, *Pseudoplusia includens*, *Pyrausta nubilalis*, *Rachiplusia nu*, *Schoenobius* spp., for example *Schoenobius bipunctifer*, *Scirpophaga* spp., for example *Scirpophaga innotata*, *Scotia segetum*, *Sesamia* spp., for example *Sesamia inferens*, *Sparganothis* spp., *Spodoptera* spp., for example *Spodoptera eradiana*, *Spodoptera exigua*, *Spodoptera frugiperda*, *Spodoptera praefica*, *Stathmopoda* spp., *Stenoma* spp., *Stomopteryx subsecivella*, *Synanthedon* spp., *Tecia solanivora*, *Thaumetopoea* spp., *Thermesia gemmatalis*, *Tinea cloacella*, *Tinea pellionella*, *Tineola bisselliella*, *Tortrix* spp., *Trichophaga tapetzella*, *Trichoplusia* spp., for example *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., for example *Gryllotalpa gryllotalpa*, *Hieroglyphus* spp., *Locusta* spp., for example *Locusta migratoria*, *Melanoplus* spp., for example *Melanoplus devastator*, *Paratlanticus ussuriensis*, *Schistocerca gregaria*;

from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Cteno-*

*cephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, in particular from the class of the Bivalvia, for example *Dreissena* spp.;

and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp., *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp., *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchulus* spp., *Tylenchorhynchus* spp., for example *Tylenchorhynchus annulatus, Tylenchulus* spp., for example *Tylenchulus semipenetrans, Xiphinema* spp., for example *Xiphinema index.*

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, corn cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cyclopothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, broflanilide, bromopropylate, chinomethionat, cryolite, cyclaniliprole, cycloxaprid, cyhalodiamide, dicloromezotiaz, dicofol, diflovidazin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, triflumezopyrim and iodomethane; and additionally preparations based on *Bacillus firmus* (I-1582, BioNeem, Votivo), and the following known active compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanon (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbony l}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-({2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969), butyl [2-(2,4-dichlorophenyl)-3-oxo-4-oxaspiro[4.5]dec-1-en-1-yl] carbonate (known from CN 102060818), (3E)-3-[1-[(6-chloro-3-pyridyl)methyl]-2-pyridinylidene]-1,1,1-trifluoropropan-2-one (known from WO2013/144213, N-(methylsulphonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926).

Fungicides

The active compounds specified herein by their common name are known and described, for example, in "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

(1) Ergosterol biosynthesis inhibitors, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37)

penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-({5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole 1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-yl thiocyanate, (1.68) 5-(allylsulphanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-yl thiocyanate, (1.73) 1-{[rel(2R,3R)-3-(2-chlorophenyl)-2-(2,4-difluorophenyl)oxiran-2-yl]methyl}-1H-1,2,4-triazol-5-yl thiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triaz-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain at complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxan, (2.23) thifluzamid, (2.24) 1-methyl-N-[2-(1,1,2,2-tetrafluorethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H- pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethinylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorphenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain at complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) fenaminstrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulphanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E, 3Z)-5-{[1-(4-chlorophenyl)-1H-pyrazol-3-yl]oxy}-2-(methoxyimino)-N,3-dimethylpent-3-enamide.

4) Inhibitors of mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of ATP production, for example (8.01) fentin acetate, (8.02) fentin chloride, (8.03) fentin hydroxide, (8.04) silthiofam.

9) Inhibitors of cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09)

metalaxyl, (12.10) metalaxyl-M (mefenoxam), (12.11) ofurace, (12.12) oxadixyl, (12.13) oxolinic acid, (12.14) octhilinone.

13) Inhibitors of signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulphate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and it salts, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanide, (15.048) triazoxide, (15.049) trichlamide, (15.050) zarilamid, (15.051) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1-(4-methoxyphenoxy)-3,3-dimethylbutan-2-yl 1H-imidazole-1-carboxylate, (15.056) 2,3,5,6-tetrachloro-4-(methylsulphonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarbonitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl)thiophene-2-sulphonohydrazide, (15.071) 5-fluoro-2-[(4-fluorobenzyl)oxy]pyrimidine-4-amine, (15.072) 5-fluoro-2-[(4-methylbenzyl)oxy]pyrimidine-4-amine, (15.073) 5-methyl-6-octyl[1,2,4]triazolo[1,5-a]pyrimidine-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acety}piperidin-4-yl)-N-(1,2,3,4-tetrahydronaphthalen-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulphate (2:1), (15.091) tert-butyl {6-[({[(1-methyl-1H-tetrazol-5-yl)(phenyl)methylene]amino}oxy)methyl]pyridin-2-yl}carbamate, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) but-3-yn-1-yl {6-[({[(Z)-(1-methyl-1H-tetrazol-5-yl)(phenyl)methylene]amino}oxy)methyl]pyridin-2-yl}carbamate, (15.096) 4-amino-5-fluoropyrimidin-2(1H)-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl) methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methy limidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazole-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazole-5-amine, (15.139) 4-(2-chloro-4-fluorophenyl)-N-(2,6-difluorophenyl)-1,3-dimethyl-1H-pyrazole-5-amine, (15.140) 4-(2-chloro-4-fluorophenyl)-N-(2-chloro-6-fluorophenyl)-1,3-dimethyl-1H-pyrazole-5-amine, (15.141) 4-(2-bromo-4-fluorophenyl)-N-(2-chloro-6-fluorophenyl)-1,3-dimethyl-1H-pyrazole-5-amine, (15.142) N-(2-bromo-6-fluorophenyl)-4-(2-chloro-4-fluorophenyl)-1,3-dimethyl-1H-pyrazole-5-amine, (15.143) 4-(2-bromo-4-fluorophenyl)-N-(2-bromophenyl)-1,3-dimethyl-1H-pyrazole-5-amine, (15.144) 4-(2-bromo-4-fluorophenyl)-N-(2-bromo-6-fluorophenyl)-1,3-dimethyl-1H-pyrazole-5-amine, (15.145) 4-(2-bromo-4-fluorophenyl)-N-(2-chlorophenyl)-1,3-dimethyl-1H-pyrazole-5-amine, (15.146) N-(2-bromophenyl)-4-(2-chloro-4-fluorophenyl)-1,3-dimethyl-1H-pyrazole-5-amine, (15.147) 4-(2-chloro-4-fluorophenyl)-N-(2-chlorophenyl)-1,3-dimethyl-1H-pyrazole-5-amine, (15.148) 4-(2-bromo-4-fluorophenyl)-N-(2,6-difluorophenyl)-1,3-dimethyl-1H-pyrazole-5-amine, (15.149) 4-(2-bromo-4-fluorophenyl)-N-(2-fluorophenyl)-1,3-dimethyl-1H-pyrazole-5-amine, (15.150) N'-(4-{3-[(difluoromethyl)sulphanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulphanyl]phenoxy}phenyl)-N-ethyl-N-methylimidoformamide, (15.152) N'-(2,5-dimethyl-4-{3-[(2,2,2-trifluoroethyl)sulphanyl]phenoxy}phenyl)-N-ethyl-N-methylimidoformamide, (15.153) N'-(2,5-dimethyl-4-{3-[(2,2,3,3-tetrafluoropropyl)sulphanyl]phenoxy}phenyl)-N-ethyl-N-methylimidoformamide, (15.154) N'-(2,5-dimethyl-4-{3-[(pentafluoroethyl)sulphanyl]phenoxy}phenyl)-N-ethyl-N-methylimidoformamide, (15.155) N'-(4-{[3-(difluoromethoxy)phenyl]sulphanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulphanyl}phenyl)-N-ethyl-N-methylimidoformamide, (15.157) N'-(2,5-dimethyl-4-{[3-(2,2,2-trifluoroethoxy)phenyl]sulphanyl}phenyl)-N-ethyl-N-methylimidoformamide, (15.158) N'-(2,5-dimethyl-4-{[3-(2,2,3,3-tetrafluoropropoxy)phenyl]sulphanyl}phenyl)-N-ethyl-N-methylimidoformamide, (15.159) N'-(2,5-dimethyl-4-{[3-(pentafluoroethoxy)phenyl]sulphanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-11-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2- chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), Pyrethrum/Pyrethrins, *Quassia amara*, *Quercus*, Quillaja, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, peas and other types of vegetable, cotton, tobacco, oilseed rape, and also fruit plants (with the fruits apples, pears, citrus fruits and grapevines). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants, from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in greenhouses, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been imbibed in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are produced in a known manner, by mixing compounds of the formula (I) with customary additives, for example customary extenders and solvents or diluents, dyes, wetters, dispersants, emulsifiers, antifoams, preservatives, secondary thickeners, stickers, gibberellins and also water.

Colorants which may be present in the seed-dressing formulations usable in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical compounds. Preference is given to using alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances conventionally used for the formulation of active agrochemical compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful adhesives which may be present in the seed-dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schadlingsbekaimpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods Include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; *from the order of the Siphonapterida*, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods Further Include:

from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa Include:

Mastigophora (Flagellata), for example *Trypanosomatidae*, for example *Trypanosoma b. brucei, T. b. gambiense, T. b. rhodesiense, T. congolense, T. cruzi, T. evansi, T. equinum, T. lewisi, T. percae, T. simiae, T. vivax, Leishmania brasiliensis, L. donovani, L. tropica*, for example *Trichomonadidae*, for example *Giardia lamblia, G. canis;*

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium spec., Isospora belli, I. canis, I. felis, I. ohioensis, I. rivolta, I. spec., I. suis, Cystisospora spec., Cryptosporidium spec.,* in particular *C. parvum*; such as Toxoplasmadidae, for example *Toxoplasma gondii, Hammondia heydornii, Neospora caninum, Besnoitia besnoitii*; such as Sarcocystidae, for example *Sarcocystis bovicanis, S. bovihominis, S. ovicanis, S. ovifelis, S. neurona, S.* spec., *S. suihominis*, such as Leucozoidae, for example *Leucozytozoon simondi*, such as Plasmodiidae, for example *Plasmodium berghei, P. falciparum, P. malariae, P. ovale, P. vivax, P.* spec., such as Piroplasmea, for example *Babesia argentina, B. bovis, B. canis, B.* spec., *Theileria parva, Theileria* spec., such as Adeleina, for example *Hepatozoon canis*, H. spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of the Pseudophyllidea for example: *Diphyllobothrium* spp., *Spirometra* spp., *Schistocephalus* spp., *Ligula* spp., *Bothridium* spp., *Diphlogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hyporaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp., from the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example *Acanthocephalus* spp., *Echinorhynchus* spp., *Leptorhynchoides* spp.;

Pentastoma: from the order of the Porocephalida, for example *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simulidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia* duttoni, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

Preparation Examples

N-[5-Ethylsulphonyl-6-[3-methyl-6-(trifluoromethyl)imidazo[4,5-c]pyridin-2-yl]-2-pyridyl]thioacetamide (Ex. 63)

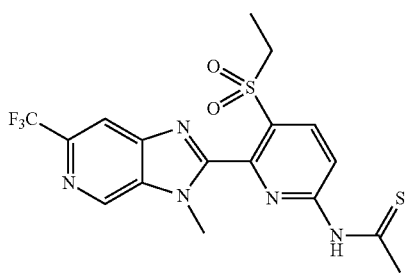 [SMILES: CCS(=O)(=O)c1ccc(NC(C)=O)nc1-c1nc2cc(C(F)(F)F)ncc2n1C]

71 mg (0.16 mmol) of N-[5-ethylsulphonyl-6-[3-methyl-6-(trifluoromethyl)imidazo[4,5-c]pyridin-2-yl]-2-pyridyl]acetamide were dissolved in 6 ml of toluene, 65.8 mg (0.16 mmol) of Lawesson's reagent (4-methoxyphenyldithiophosphonic anhydride) were added and the mixture was stirred at 90° C. for 3 h. Subsequently, a further 197.5 mg (0.48 mmol) of Lawesson's reagent were added and the mixture was stirred at 90° C. for 1 h. The solvent was distilled off under reduced pressure and the residue was purified by column chromatography using a cyclohexane/ethyl acetate gradient (30:70 to 0:100) as mobile phase.

(log P (neutral): 2.41; MH$^+$: 444; $^1$H-NMR (400 MHz, D$_6$-DMSO) δ ppm: 1.19 (t, 3H), 2.74 (s, 3H), 3.68 (q, 2H), 3.91 (s, 3H), 8.31 (s, 1H), 8.59 (d, 1H), 9.30 (s, 1H), 9.35 (br. s, 1H), 12.69 (s, 1H).

N-[5-Ethylsulphonyl-6-[3-methyl-6-(trifluoromethyl)imidazo[4,5-c]pyridin-2-yl]-2-pyridyl]acetamide

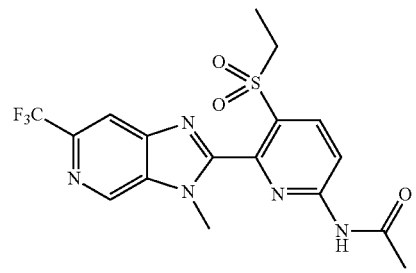

774 mg (1.80 mmol) of 5-(ethylsulphonyl)-6-[3-methyl-6-(trifluoromethyl)-3H-imidazo[4,5-c]pyridin-2-yl]pyridine-2-amine were initially charged with 220.8 mg of 4-dimethylaminopyridine (1.80 mmol) in a mixture of 20 ml each of pyridine and toluene, and 425.7 mg (5.42 mmol) of acetyl chloride were added. The reaction mixture was stirred at 100° C. for 45 min, the solvent was distilled off under reduced pressure and the residue was purified by column chromatography using cyclohexane/ethyl acetate as mobile phase.

(log P (neutral): 2.01; MH$^+$: 428; $^1$H-NMR (400 MHz, D$_6$-DMSO) δ ppm: 1.15 (t, 3H), 2.17 (s, 3H), 3.62 (q, 2H), 3.88 (s, 3H), 8.29 (s, 1H), 8.46-8.53 (m, 2H), 9.29 (s, 1H), 11.31 (s, 1H).

N-{5-(Ethylsulphonyl)-6-[3-methyl-6-(trifluoromethyl)-3H-imidazo[4,5-c]pyridin-2-yl]pyridin-2-yl}-2-methylpropanamide (Ex. 16)

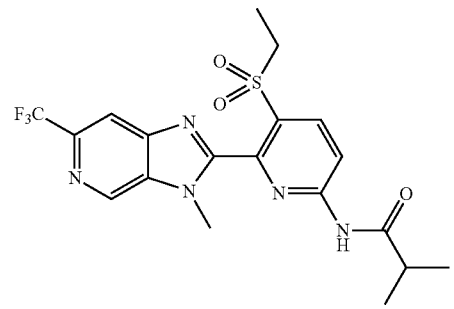 [SMILES: CCS(=O)(=O)c1ccc(NC(=O)C(C)C)nc1-c1nc2cc(C(F)(F)F)ncc2n1C]

54 mg (0.11 mmol) of 5-(ethylsulphonyl)-6-[3-methyl-6-(trifluoromethyl)-3H-imidazo[4,5-c]pyridin-2-yl]pyridine-2-amine were dissolved in 4 ml of acetonitrile, 360 mg of pyridine (4.54 mmol) and 13.87 mg of 4-dimethylaminopyridine (0.11 mmol) were added and the mixture was heated to 60° C. 123.4 mg (1.13 mmol) of 2-methylpropionyl chloride were then added, the heating bath was removed and the mixture was stirred at room temperature overnight. The reaction was diluted with 10 ml of dichloromethane, washed with 1 M hydrochloric acid solution and dried over sodium sulphate, and the solvent was then distilled off under reduced pressure. The residue was purified by column chromatography using cyclohexane/ethyl acetate (1:1) as mobile phase.

(log P (neutral): 2.61; MH$^+$: 456; $^1$H-NMR (400 MHz, D$_6$-DMSO) δ ppm: 1.11-1.19 (m, 9H), 2.75-2.81 (m, 1H), 3.61 (q, 2H), 3.87 (s, 3H), 8.30 (s, 1H), 8.47 (d, 1H), 8.55 (d, 1H), 9.29 (s, 1H), 11.27 (s, 1H).

5-(Ethylsulphonyl)-6-[3-methyl-6-(trifluoromethyl)-3H-imidazo[4,5-c]pyridin-2-yl]pyridine-2-amine (Ex. 14)

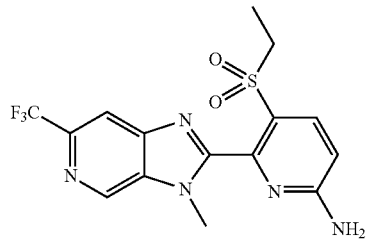 [SMILES: CCS(=O)(=O)c1ccc(N)nc1-c1nc2cc(C(F)(F)F)ncc2n1C]

118 mg (0.29 mmol) of 2-(6-chloro-3-ethylsulphonyl-2-pyridyl)-3-methyl-6-(trifluoromethyl)imidazo[4,5-c]pyridine, 3 ml of ethanol and 3 ml of 26% strength aqueous ammonia solution were stirred in a microwave oven at 120° C. and 15 bar for 6 h. The mixture was freed of the solvent under reduced pressure and the residue was used directly for the next step.

(log P (neutral): 1.62; MH$^+$: 386; $^1$H-NMR (400 MHz, D$_6$-DMSO) δ ppm: 1.13 (t, 3H), 3.46 (q, 2H), 3.82 (s, 3H), 6.76 (d, 1H), 7.42 (br. s., 2H), 7.93 (d, 1H), 8.24 (s, 1H), 9.23 (s, 1H).

2-(6-Chloro-3-ethylsulphonyl-2-pyridyl)-3-methyl-6-(trifluoromethyl)imidazo[4,5-c]pyridine (Ex. XIII-1)

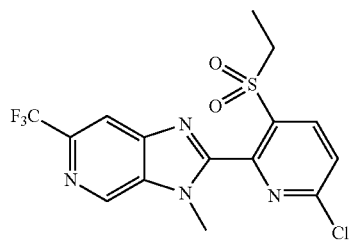 [SMILES: CCS(=O)(=O)c1ccc(Cl)nc1-c1nc2cc(C(F)(F)F)ncc2n1C]

900 mg (2.41 mmol) of 2-(6-chloro-3-ethylsulphanyl-2-pyridyl)-3-methyl-6-(trifluoromethyl)imidazo[4,5-c]pyridine were dissolved in 50 ml of dichloromethane, 555.6 mg (12.0 mmol) of formic acid and 1.64 g (16.8 mmol) of 35% strength hydrogen peroxide were added at room temperature and the mixture was then stirred at room temperature for 5 h. The mixture was diluted with water and sodium bisulfite solution was added, the mixture was stirred for 1 h and saturated sodium bicarbonate solution was then added. The organic phase was separated off, the aqueous phase was extracted twice with dichloromethane and the combined organic phases were then freed of the solvent under reduced pressure. The residue was purified by column chromatography by means of preparative HPLC using a water/acetonitrile gradient as eluent.

(log P (neutral): 2.54; MH$^+$: 405; $^1$H-NMR (400 MHz, D$_6$-DMSO) δ ppm: 1.20 (t, 3H), 3.77 (q, 2H), 3.91 (s, 3H), 8.13 (d, 1H), 8.32 (s, 1H), 8.56 (d, 1H), 9.30 (s, 1H).

2-(6-Chloro-3-ethylsulphanyl-2-pyridyl)-3-methyl-6-(trifluoromethyl)imidazo[4,5-c]pyridine (Ex. XI-1)

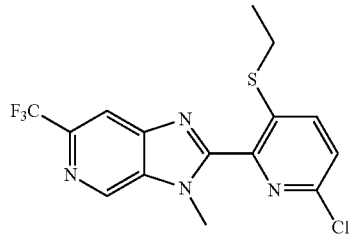 [SMILES: CCSc1ccc(Cl)nc1-c1nc2cc(C(F)(F)F)ncc2n1C]

4.00 g (10.7 mmol) of 2-(3,6-dichloro-2-pyridyl)-3-methyl-6-(trifluoromethyl)imidazo[4,5-c]pyridine were dissolved in 60 ml of tetrahydrofuran, 446 mg (11.1 mmol) of sodium hydride were added at −5° C. and the mixture was stirred at 0° C. for 30 minutes. 733 mg (11.8 mmol) of ethanethiol were then added dropwise over 30 minutes at −5° C., the cooling bath was removed and the mixture was stirred at room temperature for 2 h. The reaction mixture was hydrolysed with water, the organic phase was separated off and the aqueous phase was extracted twice with ethyl acetate. The organic phases were combined, washed with sodium chloride solution and dried over sodium sulphate, and the solvent was then distilled off under reduced pressure. The residue was purified by trituration with methyl tert-butyl ketone/dichloromethane 25:1.

(log P (neutral): 3.06; MH$^+$: 373

2-(3,6-Dichloro-2-pyridyl)-3-methyl-6-(trifluoromethyl)imidazo[4,5-c]pyridine (Ex. IX-1)

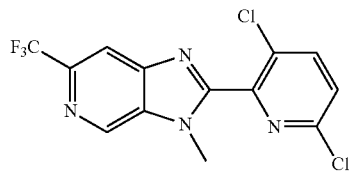 [SMILES: Cn1c(-c2nc(Cl)ccc2Cl)nc2cc(C(F)(F)F)ncc21]

20 g (104.6 mmol) of N$^3$-methyl-6-(trifluoromethyl)pyridine-3,4-diamine, 25.11 g (130.8 mmol) of 3,6-dichloropyridine-2-carboxylic acid and 20.06 g (104.6 mmol) of 1-(3-dimethylaminopropyl)-3-ethylcarbodiimide hydrochloride (EDCI) were stirred in 200 ml of pyridine at 120° C. for 8 h. The reaction mixture was freed of solvent under reduced pressure, water was added and the mixture was extracted three times with ethyl acetate. The organic phases were combined and dried over sodium sulphate, and the solvent was then distilled off under reduced pressure. The residue was purified by column chromatography using a cyclohexane/ethyl acetate gradient as mobile phase.

(log P (neutral): 2.81; MH$^+$: 347; $^1$H-NMR (400 MHz, D$_6$-DMSO) δ ppm: 3.99 (s, 3H), 7.89 (d, 1H), 8.32 (s, 1H), 8.35 (d, 1H), 9.28 (s, 1H).

N-{5-(Ethylsulphonyl)-6-[3-methyl-6-(trifluoromethyl)-3H-imidazo[4,5-c]pyridin-2-yl]pyridin-2-yl}methanesulphonamide (Ex. 26)

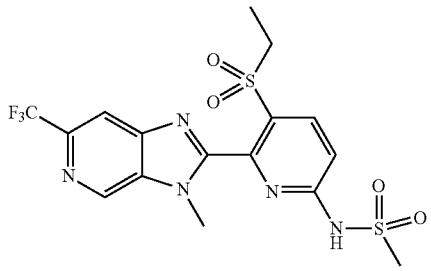 [SMILES: CCS(=O)(=O)c1ccc(NS(C)(=O)=O)nc1-c1nc2cc(C(F)(F)F)ncc2n1C]

66 mg (0.13 mmol) of 5-(ethylsulphonyl)-6-[3-methyl-6-(trifluoromethyl)-3H-imidazo[4,5-c]pyridin-2-yl]pyridine-2-amine were dissolved in 5 ml of acetonitrile, 439 mg (5.54 mmol) of pyridine and 17.0 mg (0.13 mmol) of 4-dimethylaminopyridine were added, and 124.6 mg (0.69 mmol) of methanesulphonic anhydride were added dropwise under argon. The mixture was stirred at room temperature for 2 h, another 124.6 mg (0.69 mmol) of methanesulphonic anhydride were added and the mixture was stirred at 60° C. for 2 h. The solvent was distilled off and the residue was dissolved in dichloromethane and washed with 2 N hydrochloric acid solution. The aqueous phase was extracted twice with dichloromethane, the combined organic phases were dried over sodium sulphate and the solvent was then distilled off under reduced pressure. The residue was purified by column chromatography using a water/acetonitrile gradient as mobile phase.

(log P (neutral): 0.85; MH$^+$: 464; $^1$H-NMR (400 MHz, D$_6$-DMSO) δ ppm: 1.20 (t, 3H), 3.34 (s, 3H), 3.74 (q, 2H), 3.92 (s, 3H), 7.34 (d, 1H), 8.29 (s, 1H), 8.40 (d, 1H), 9.29 (s, 1H), 11.72 (s, 1H).

1-[5-Ethylsulphonyl-6-[3-methyl-6-(trifluoromethyl)imidazo[4,5-c]pyridin-2-yl]-2-pyridyl]-1,2-dimethylhydrazine (Ex. 60)

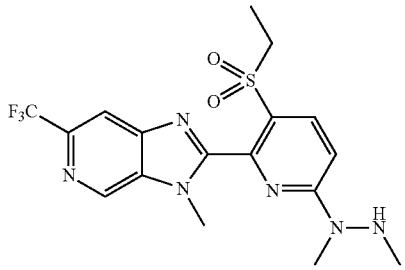 [SMILES: CCS(=O)(=O)c1ccc(N(C)NC)nc1-c1nc2cc(C(F)(F)F)ncc2n1C]

Under argon, 102 mg (0.25 mmol) of 2-(6-chloro-3-ethylsulphonyl-2-pyridyl)-3-methyl-6-(trifluoromethyl)imidazo[4,5-c]pyridine were dissolved in 7 ml of acetonitrile, 150.9 mg (1.09 mmol) of potassium carbonate and 103.8 mg (0.78 mmol) of 1,2-dimethylhydrazinium dichloride were added and the mixture was stirred at room temperature for 4 h. The mixture was filtered off and the mother liquor was freed of the solvent. The residue was taken up in dichloromethane and washed once with water. The organic phase was dried over sodium sulphate, and the solvent was then distilled off under reduced pressure.

(log P (neutral): 2.39; MH$^+$: 429; $^1$H-NMR (400 MHz, D$_6$-DMSO) δ ppm: 1.15 (t, 3H), 2.54 (d, 3H), 3.23 (s (3H), 3.54 (q, 2H), 3.87 (s, 3H), 5.24 (q, 1H), 7.37 (d, 1H), 8.02 (d, 1H), 8.25 (s, 1H), 9.25 (s, 1H).

2-(3,6-Difluoropyridin-2-yl)-3-methyl-6-(trifluoromethyl)-3H-imidazo[4,5-c]pyridine (Ex. IX-2)

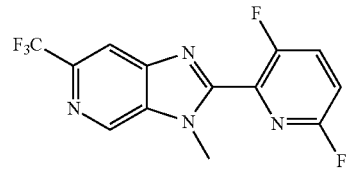 [SMILES: Cn1c(-c2nc(F)ccc2F)nc2cc(C(F)(F)F)ncc21]

5.39 g (23.6 mmol) of N$^3$-methyl-6-(trifluoromethyl)pyridine-3,4-diamine, 4.90 g (30.8 mmol) of 3,6-difluoropyridine-2-carboxylic acid and 4.54 g (23.6 mmol) of 1-(3-dimethylaminopropyl)-3-ethylcarbodiimide hydrochloride (EDCI) were stirred in 50 ml of pyridine at 120° C. for 8 h. The reaction mixture was freed of solvent under reduced pressure, water was added and the mixture was extracted three times with ethyl acetate. The organic phases were combined and dried over sodium sulphate, and the solvent was then distilled off under reduced pressure. The residue was purified by column chromatography using a cyclohexane/acetone gradient as mobile phase.

log P (neutral): 2.11; MH$^+$: 315; $^1$H-NMR (400 MHz, D$_6$-DMSO) δ ppm: 4.14 (s, 3H), 7.60-7.64 (m, 1H), 8.27-8.33 (m, 2H), 9.28 (s, 1H).

2-[3-(Ethylsulphanyl)-6-fluoropyridin-2-yl]-3-methyl-6-(trifluoromethyl)-3H-imidazo[4,5-c]pyridine (Ex. XI-2)

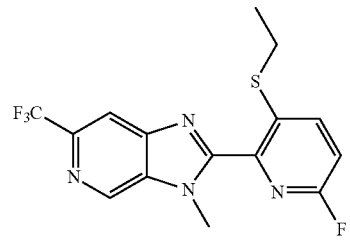 [SMILES: CCSc1ccc(F)nc1-c1nc2cc(C(F)(F)F)ncc2n1C]

6.12 g (19.4 mmol) of 2-(3,6-difluoropyridin-2-yl)-3-methyl-6-(trifluoromethyl)-3H-imidazo[4,5-c]pyridine were dissolved in 200 ml of tetrahydrofuran, and 857 mg (21.4 mmol) of sodium hydride were added at 0° C. 1.67 mg (19.8 mmol) of sodium thioethoxide were then added, and the mixture was stirred at room temperature overnight. Water was added and the reaction mixture was extracted three times with ethyl acetate. The organic phases were combined and dried over sodium sulphate, and the solvent was then distilled off under reduced pressure. The residue was purified by column chromatography using a cyclohexane/acetone gradient as mobile phase.

log P (neutral): 2.73; MH$^+$: 357; 1H-NMR (400 MHz, D6-DMSO) δ ppm: 1.18 (t, 3H), 3.01 (q, 2H), 4.00 (s, 3H), 7.49-7.52 (m, 1H), 8.28-8.32 (m, 2H), 9.25 (s, 1H).

2-[3-(Ethylsulphonyl)-6-fluoropyridin-2-yl]-3-methyl-6-(trifluoromethyl)-3H-imidazo[4,5-c]pyridine (Ex. XIII-2)

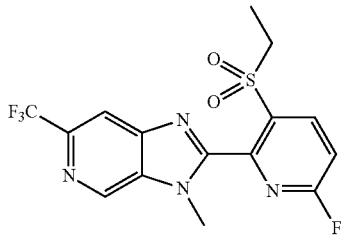 [SMILES: CCS(=O)(=O)c1ccc(F)nc1-c1nc2cc(C(F)(F)F)ncc2n1C]

3.68 g (10.2 mmol) of 2-[3-(ethylsulphanyl)-6-fluoropyridin-2-yl]-3-methyl-6-(trifluoromethyl)-3H-imidazo[4,5-c]pyridine were dissolved in 100 ml of dichloromethane. At room temperature, 3.79 g (75% strength, 16.4 mmol) of meta-chloroperbenzic acid were added and the mixture was stirred overnight. Saturated sodium thiosulphate solution and then saturated sodium bicarbonate solution were added to the mixture. The organic phase was separated off, the aqueous phase was extracted twice with dichloromethane and the combined organic phases were then freed of the solvent under reduced pressure. The residue was purified by column chromatography by means of preparative HPLC using a water/acetonitrile gradient as eluent.

log P (neutral): 2.30; MH$^+$: 389; $^1$H-NMR (400 MHz, D$_6$-DMSO) δ ppm: 1.20 (t, 3H), 3.77 (q, 2H), 3.91 (s, 3H), 7.79-7.82 (m, 1H), 8.31 (s, 1H), 8.70-8.74 (m, 1H), 9.29 (s, 1H).

2-[6-Ethoxy-3-(ethylsulphonyl)pyridin-2-yl]-3-methyl-6-(trifluoromethyl)-3H-imidazo[4,5-c]pyridine (Ex. 10)

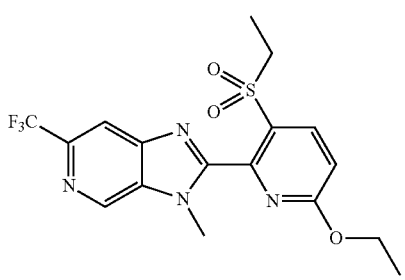 [SMILES: CCOc1ccc(S(=O)(=O)CC)c(-c2nc3cc(C(F)(F)F)ncc3n2C)n1]

23 µl (0.38 mmol) of ethanol were initially charged in 5 ml of tetrahydrofuran, and 15 mg (60% strength, 0.38 mmol) of sodium hydride were added. 100 mg (0.25 mmol) of 2-[3-(ethylsulphonyl)-6-fluoropyridin-2-yl]-3-methyl-6-(trifluoromethyl)-3H-imidazo[4,5-c]pyridine were added and the mixture was stirred at room temperature overnight. Water was added to the mixture. The organic phase was separated off, the aqueous phase was extracted twice with ethyl acetate and the combined organic phases were then freed of the solvent under reduced pressure. The residue was purified by column chromatography by means of preparative HPLC using a water/acetonitrile gradient as eluent.

log P (neutral): 2.86; MH$^+$: 415; $^1$H-NMR (400 MHz, D$_6$-DMSO) δ ppm: 1.18 (t, 3H), 1.35 (t, 3H), 3.69 (q, 2H), 3.91 (s, 3H), 4.42 (q, 2H), 7.30 (d, 1H), 8.28 (s, 1H), 8.34 (d, 1H), 9.29 (s, 1H).

2-[6-(Ethylsulphanyl)-3-(ethylsulphonyl)pyridin-2-yl]-3-methyl-6-(trifluoromethyl)-3H-imidazo[4,5-c]pyridine (Ex. 5)

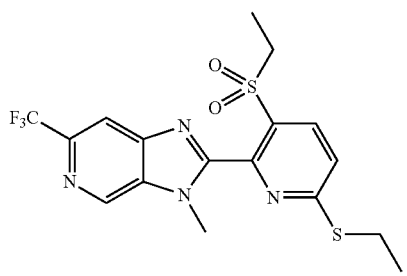 [SMILES: CCSc1ccc(S(=O)(=O)CC)c(-c2nc3cc(C(F)(F)F)ncc3n2C)n1]

32 mg (0.38 mmol) of sodium thioethoxide were initially charged in 5 ml of tetrahydrofuran, and 15 mg (60% strength, 0.38 mmol) of sodium hydride were added. 100 mg (0.25 mmol) of 2-[3-(ethylsulphonyl)-6-fluoropyridin-2-yl]-3-methyl-6-(trifluoromethyl)-3H-imidazo[4,5-c]pyridine were added and the mixture was stirred at room temperature overnight. Methanol was added and the mixture was then concentrated to dryness. The residue was taken up in water and ethyl acetate. The organic phase was separated off, the aqueous phase was extracted twice with ethyl acetate and the combined organic phases were then freed of the solvent under reduced pressure. The residue was purified by column chromatography by means of preparative HPLC using a water/acetonitrile gradient as eluent.

log P (neutral): 3.14; MH$^+$: 431; $^1$H-NMR (400 MHz, D$_6$-DMSO) δ ppm: 1.19 (t, 3H), 1.30 (t, 3H), 3.20 (q, 2H), 3.71 (q, 2H), 3.90 (s, 3H), 7.82 (d, 1H), 8.25 (d, 1H), 8.29 (s, 1H), 9.29 (s, 1H).

2-[3,6-Bis(ethylsulphonyl)pyridin-2-yl]-3-methyl-6-(trifluoromethyl)-3H-imidazo[4,5-c]pyridine (Ex. 15)

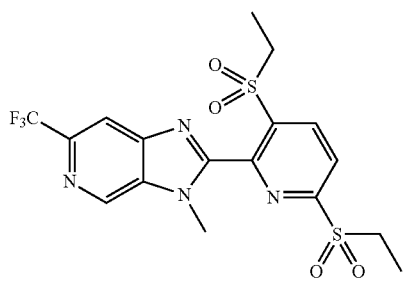 [SMILES: CCS(=O)(=O)c1ccc(S(=O)(=O)CC)c(-c2nc3cc(C(F)(F)F)ncc3n2C)n1]

171 mg (0.39 mmol) of 2-[6-(ethylsulphanyl)-3-(ethylsulphonyl)pyridin-2-yl]-3-methyl-6-(trifluoromethyl)-3H-imidazo[4,5-c]pyridine were dissolved in 7 ml of dichloromethane, 101 mg (0.43 mmol) of meta-chloroperbenzoic acid were then added and the mixture was stirred at room temperature for 1 h. The mixture was washed once with saturated sodium thiosulphate solution and then with saturated sodium bicarbonate solution. The organic phase was dried over sodium sulphate, and the solvent was then distilled off under reduced pressure. The residue was purified by column chromatography using a water/acetonitrile gradient as mobile phase.

log P (neutral): 2.27; MH⁺: 463; ¹H-NMR (400 MHz, D₆-DMSO) δ ppm: 1.18-1.26 (m, 6H), 3.59 (q, 2H), 3.90 (q, 2H), 3.95 (s, 3H), 8.33 (d, 1H), 8.56 (d, 1H), 8.89 (d, 1H), 9.31 (s, 1H).

2-[6-(Ethylsulphinyl)-3-(ethylsulphonyl)pyridin-2-yl]-3-methyl-6-(trifluoromethyl)-3H-imidazo[4,5-c]pyridine (Ex. 37)

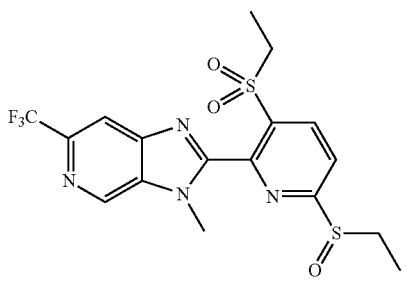 [SMILES: CCS(=O)c1ccc(S(=O)(=O)CC)c(-c2nc3cc(C(F)(F)F)ncc3n2C)n1]

171 mg (0.39 mmol) of 2-[6-(ethylsulphanyl)-3-(ethylsulphonyl)pyridin-2-yl]-3-methyl-6-(trifluoromethyl)-3H-imidazo[4,5-c]pyridine were dissolved in 7 ml of dichloromethane, 101 mg (0.43 mmol) of meta-chloroperbenzoic acid were then added and the mixture was stirred at room temperature for 1 h. The mixture was washed once with saturated sodium thiosulphate solution and then with saturated sodium bicarbonate solution. The organic phase was dried over sodium sulphate, and the solvent was then distilled off under reduced pressure. The residue was purified by column chromatography using a water/acetonitrile gradient as mobile phase.

log P (neutral): 2.02; MH⁺: 447; ¹H-NMR (400 MHz, D₆-DMSO) δ ppm: 1.12 (t, 3H), 1.22 (t, 3H), 2.98-3.05 (m, 2H), 3.78-3.87 (m, 2H), 3.90 (s, 3H), 8.32 (s, 1H), 8.38 (d, 1H), 8.82 (d, 1H), 9.30 (s, 1H).

2-[6-(S-Ethylsulphonimidoyl)-3-(ethylsulphonyl)pyridin-2-yl]-3-methyl-6-(trifluoromethyl)-3H-imidazo[4,5-c]pyridine (Ex. 41)

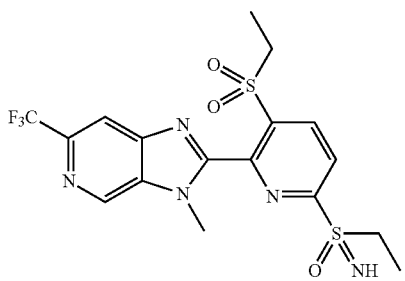 [SMILES: CCS(=N)(=O)c1ccc(S(=O)(=O)CC)c(-c2nc3cc(C(F)(F)F)ncc3n2C)n1]

76 mg (0.17 mmol) of 2-[6-(ethylsulphinyl)-3-(ethylsulphonyl)pyridin-2-yl]-3-methyl-6-(trifluoromethyl)-3H-imidazo[4,5-c]pyridine were dissolved in 2 ml of acetonitrile, 41 mg (0.20 mmol) of 4-nitrobenzenesulphonamide and 88 mg (0.27 mmol) of diacetoxyiodobenzene were then added and the mixture was stirred at 77° C. for 72 h. Another 88 mg (0.27 mmol) of diacetoxyiodobenzene were then added, and the mixture was stirred at 77° C. for a further 72 h. This gave the product which was purified by distillative removal of the solvent under reduced pressure and by column chromatography of the residue using a water/acetonitrile gradient as mobile phase.

log P (neutral): 1.79; MH⁺: 462; ¹H-NMR (400 MHz, D₆-DMSO) δ ppm: 1.19 (t, 3H), 1.25 (t, 3H), 3.39-3.51 (m, 2H), 3.90 (q, 2H), 3.94 (s, 3H), 8.34 (s, 1H), 8.54 (d, 1H), 8.85 (d, 1H), 9.32 (s, 1H).

2-[3-(Ethylsulphonyl)-6-(methylsulphanyl)pyridin-2-yl]-3-methyl-6-(trifluoromethyl)-3H-imidazo[4,5-c]pyridine (Ex. 28)

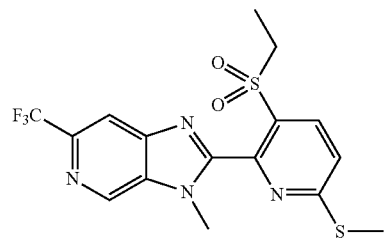 [SMILES: CCS(=O)(=O)c1ccc(SC)nc1-c1nc2cc(C(F)(F)F)ncc2n1C]

27 mg (0.38 mmol) of sodium thiomethoxide were initially charged in 5 ml of tetrahydrofuran, and 15 mg (60% strength, 0.38 mmol) of sodium hydride were added. 100 mg (0.25 mmol) of 2-[3-(ethylsulphonyl)-6-fluoropyridin-2-yl]-3-methyl-6-(trifluoromethyl)-3H-imidazo[4,5-c]pyridine were added and the mixture was stirred at room temperature overnight. Methanol was added and the mixture was then concentrated to dryness. The residue was taken up in water and ethyl acetate. The organic phase was separated off, the aqueous phase was extracted twice with ethyl acetate and the combined organic phases were then freed of the solvent under reduced pressure. The residue was purified by column chromatography using a water/acetonitrile gradient as mobile phase.

log P (neutral): 2.75; MH⁺: 417; ¹H-NMR (400 MHz, D₆-DMSO) δ ppm: 1.19 (t, 3H), 2.60 (s, 3H), 3.72 (q, 2H), 3.90 (s, 3H), 7.85 (d, 1H), 8.27 (d, 1H), 8.29 (s, 1H), 9.29 (s, 1H).

[{5-(Ethylsulphonyl)-6-[3-methyl-6-(trifluoromethyl)-3H-imidazo[4,5-c]pyridin-2-yl]pyridin-2-yl}(methyl)-lambda4-sulphanylidene]cyanamide (Ex. 43)

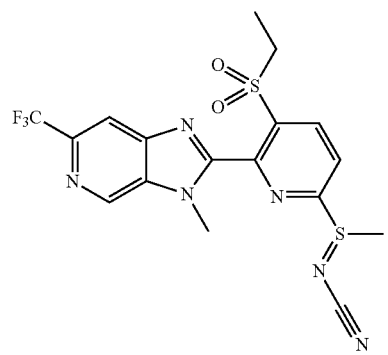 [SMILES: CCS(=O)(=O)c1ccc(/S(C)=N/C#N)nc1-c1nc2cc(C(F)(F)F)ncc2n1C]

410 mg (0.98 mmol) of 2-[3-(ethylsulphonyl)-6-(methylsulphanyl)pyridin-2-yl]-3-methyl-6-(trifluoromethyl)-3H-imidazo[4,5-c]pyridine were initially charged in 40 ml of methanol, and 54 mg (1.28 mmol) of cyanamide and 133 mg (1.18 mmol) of potassium tert-butoxide were added. 263 mg (1.47 mmol) of N-bromosuccinimide were then added a little at a time, and the mixture was stirred at room temperature overnight. The mixture was concentrated, and saturated sodium thiosulphate solution and dichloromethane were then added. The organic phase was separated off, the aqueous phase was extracted twice with dichloromethane and the combined organic phases were then freed of the solvent under reduced pressure. The residue was purified by column chromatography using a water/acetonitrile gradient as mobile phase.

log P (neutral): 1.75; MH$^+$: 457; $^1$H-NMR (400 MHz, D$_6$-DMSO) δ ppm: 1.24 (t, 3H), 3.29 (s, 3H), 3.87-3.94 (m, 2H), 3.98 (s, 3H), 8.34 (s, 1H), 8.57 (d, 1H), 8.89 (d, 1H), 9.33 (s, 1H).

2-[6-(Benzylsulphanyl)-3-(ethylsulphonyl)pyridin-2-yl]-3-methyl-6-(trifluoromethyl)-3H-imidazo[4,5-c]pyridine (Ex. 30)

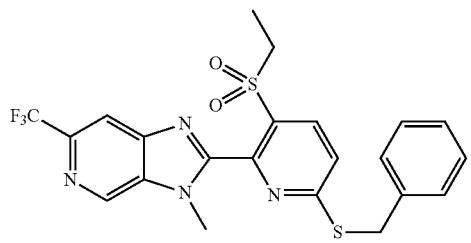 [SMILES: CCS(=O)(=O)c1ccc(SCc2ccccc2)nc1-c1nc2cc(C(F)(F)F)ncc2n1C]

64 mg (0.51 mmol) of benzylmercaptan were initially charged in 10 ml of tetrahydrofuran, and 31 mg (60% strength, 0.77 mmol) of sodium hydride were added. 200 mg (0.51 mmol) of 2-[3-(ethylsulphonyl)-6-fluoropyridin-2-yl]-3-methyl-6-(trifluoromethyl)-3H-imidazo[4,5-c]pyridine were added and the mixture was stirred at room temperature overnight. Methanol was added and the mixture was then concentrated to dryness. The residue was taken up in water and ethyl acetate. The organic phase was separated off, the aqueous phase was extracted twice with ethyl acetate and the combined organic phases were then freed of the solvent under reduced pressure. The residue was purified by column chromatography using a water/acetonitrile gradient as mobile phase.

log P (neutral): 3.72; MH$^+$: 493; $^1$H-NMR (400 MHz, D$_6$-DMSO) δ ppm: 1.18 (t, 3H), 3.69 (q, 2H), 3.80 (s, 3H), 4.49 (s, 2H), 7.23-7.39 (m, 5H), 7.87 (d, 1H), 8.27 (d, 1H), 8.30 (s, 1H), 9.29 (s, 1H).

5-(Ethylsulphonyl)-N-isopropyl-6-[3-methyl-6-(trifluoromethyl)-3H-imidazo[4,5-c]pyridin-2-yl]pyridine-2-sulphonamide (Ex. 49)

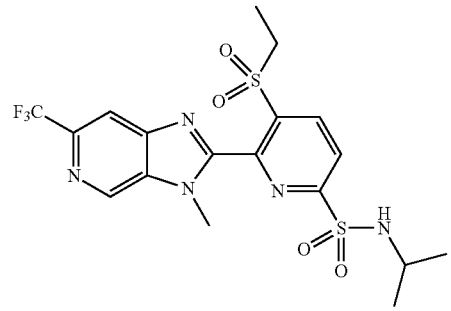 [SMILES: CCS(=O)(=O)c1ccc(S(=O)(=O)NC(C)C)nc1-c1nc2cc(C(F)(F)F)ncc2n1C]

520 mg (1.05 mmol) of 2-[6-(benzylsulphanyl)-3-(ethylsulphonyl)pyridin-2-yl]-3-methyl-6-(trifluoromethyl)-3H-imidazo[4,5-c]pyridine were initially charged in a mixture of 10 ml of dichloromethane, 2 ml of water and 1 ml of acetic acid at 0° C., and 624 mg (3.16 mmol) of 1,3-dichloro-5,5-dimethylhydantoin, dissolved in dichloromethane, were added dropwise. The mixture was stirred at room temperature overnight. The organic phase was separated off and the aqueous phase was extracted twice with dichloromethane. At 0° C., a quarter of the combined organic dichloromethane solution was added dropwise to a solution of isopropylamine (0.028 ml, 0.33 mmol) in 2 ml of tetrahydrofuran. The mixture was stirred at room temperature for 3 h and then concentrated to dryness on a rotary evaporator. The residue was purified by column chromatography using a water/acetonitrile gradient as mobile phase.

log P (neutral): 2.49; MH$^+$: 492; $^1$H-NMR (400 MHz, D$_6$-DMSO) δ ppm: 1.01 (d, 6H), 1.22 (t, 3H), 3.45-3.53 (m, 1H), 3.84 (q, 2H), 3.93 (s, 3H), 8.29 (bs, 1H), 8.35 (s, 1H), 8.45 (d, 1H), 8.82 (d, 1H), 9.35 (s, 1H).

2-{6-[(E)-2-Cyclopropylvinyl]-3-(ethylsulphonyl)pyridin-2-yl}-3-methyl-6-(trifluoromethyl)-3H-imidazo[4,5-c]pyridine (Ex. 40)

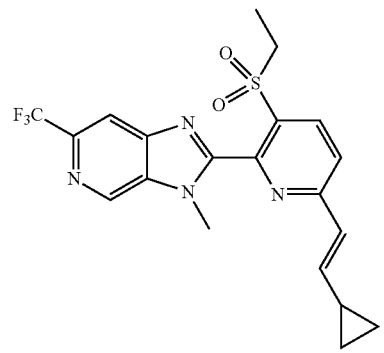 [SMILES: CCS(=O)(=O)c1ccc(/C=C/C2CC2)nc1-c1nc2cc(C(F)(F)F)ncc2n1C]

100 mg (0.25 mmol) of 2-(6-chloro-3-ethylsulphonyl-2-pyridyl)-3-methyl-6-(trifluoromethyl)imidazo[4,5-c]pyridine, 48 mg (0.25 mmol) of (E)-2-cyclopropylvinylboronic acid pinacol ester and 9 mg (0.007 mmol) of tetrakis(triphenylphosphine)palladium(0) were initially charged in a mixture of degassed dioxane (2 ml) and degassed sodium carbonate solution (1M, 1 ml), and the mixture was stirred at 96° C. for 16 h. The reaction mixture was then cooled to room temperature and concentrated under reduced pressure, and the residue was taken up in water and dichloromethane. The phases were separated and the aqueous phase was extracted three times with dichloromethane. The combined organic phases were then freed of the solvent and the residue was purified by column chromatography using a water/acetonitrile gradient as mobile phase.

log P (neutral): 3.24; MH$^+$: 437; $^1$H-NMR (400 MHz, D$_6$-DMSO) δ ppm: 0.67-0.69 (m, 2H), 0.91-0.96 (m, 2H), 1.18 (t, 3H), 1.72-1.76 (m, 1H), 3.69 (q, 2H), 3.86 (s, 3H), 6.60 (dd, 1H), 6.81 (d, 1H), 7.82 (d, 1H), 8.28 (s, 1H), 8.39 (d, 1H), 9.28 (s, 1H).

Methyl 5-(ethylsulphonyl)-6-[3-methyl-6-(trifluoromethyl)-3H-imidazo[4,5-c]pyridin-2-yl]pyridine-2-carboxylate (Ex. 12)

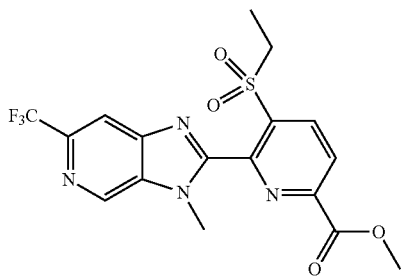 [SMILES: CCS(=O)(=O)c1ccc(C(=O)OC)nc1-c1nc2cc(C(F)(F)F)ncc2n1C]

In an autoclave, 1.98 g (4.88 mmol) of 2-(6-chloro-3-ethylsulphonyl-2-pyridyl)-3-methyl-6-(trifluoromethyl)imidazo[4,5-c]pyridine, 749 mg (9.12 mmol) of sodium acetate and 386 mg (0.48 mmol) of [1,1'-bis(diphenylphosphino)ferrocene]dichloropalladium(II)-acetone complex were initially charged in 100 ml of methanol, and the mixture was carbonylated at 80° C. under a carbon monoxide atmosphere at a pressure of 10 bar for 15 h. The mixture was then cooled to room temperature and the carbon monoxide atmosphere was removed. The reaction mixture was concentrated under reduced pressure and the residue was taken up in water and dichloromethane. The phases were separated and the aqueous phase was extracted three times with dichloromethane. The combined organic phases were then freed of the solvent and the residue was purified by column chromatography using a water/acetonitrile gradient as mobile phase.

log P (neutral): 2.17; MH$^+$: 429; $^1$H-NMR (400 MHz, D$_6$-DMSO) δ ppm: 1.20 (t, 3H), 3.81 (q, 2H), 3.89 (s, 3H), 3.96 (s, 3H), 8.32 (s, 1H), 8.54 (d, 1H), 8.75 (d, 1H), 9.30 (s, 1H).

5-(Ethylsulphonyl)-6-[3-methyl-6-(trifluoromethyl)-3H-imidazo[4,5-c]pyridin-2-yl]pyridine-2-carboxylic acid

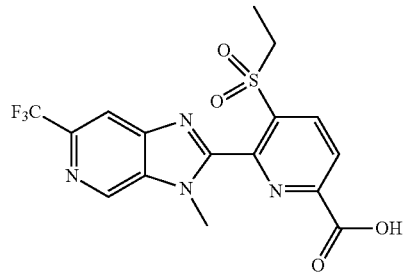 [SMILES: CCS(=O)(=O)c1ccc(C(=O)O)nc1-c1nc2cc(C(F)(F)F)ncc2n1C]

944 mg (2.20 mmol) of methyl 5-(ethylsulphonyl)-6-[3-methyl-6-(trifluoromethyl)-3H-imidazo[4,5-c]pyridin-2-yl]pyridine-2-carboxylate were initially charged in 10 ml of ethanol, 2.42 ml of aqueous sodium hydroxide solution (1M, 2.42 mmol) were added and the mixture was stirred at room temperature for 30 min. The reaction mixture was concentrated under reduced pressure and the residue was taken up in water. The mixture was then acidified with dilute hydrochloric acid and the precipitated solid was filtered off with suction, washed with water and dried.

log P (neutral): 0.76; MH$^+$: 415; $^1$H-NMR (400 MHz, D$_6$-DMSO) δ ppm: 1.20 (t, 3H), 3.81 (q, 2H), 3.90 (s, 3H), 8.32 (s, 1H), 8.49 (d, 1H), 8.71 (d, 1H), 9.30 (s, 1H).

5-(Ethylsulphonyl)-N-methyl-6-[3-methyl-6-(trifluoromethyl)-3H-imidazo[4,5-c]pyridin-2-yl]pyridine-2-carboxamide (Ex. 31)

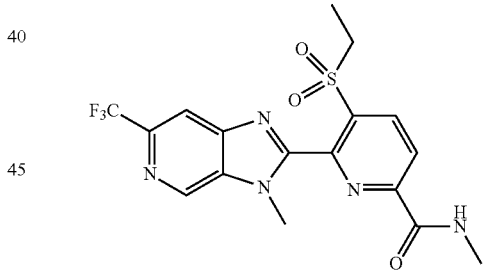

200 mg (0.48 mmol) of 5-(ethylsulphonyl)-6-[3-methyl-6-(trifluoromethyl)-3H-imidazo[4,5-c]pyridin-2-yl]pyridine-2-carboxylic acid were initially charged in 10 ml of dioxane, 111 mg of 1-ethyl-3-(3-dimethylaminopropyl)carbodiimide hydrochloride (EDCI, 0.57 mmol) were added and the mixture was stirred at room temperature for 1 h. 0.24 ml of methanamine solution (2M in THF, 0.48 mmol) were then added and the reaction mixture was stirred at room temperature for 16 h. The mixture was concentrated under reduced pressure and the residue was taken up in water and dichloromethane. The phases were separated and the aqueous phase was extracted three times with dichloromethane. The combined organic phases were then freed of the solvent and the residue was purified by column chromatography using a water/acetonitrile gradient as mobile phase.

log P (neutral): 1.96; MH$^+$: 428; $^1$H-NMR (400 MHz, D$_6$-DMSO) δ ppm: 1.19 (t, 3H), 2.84 (d, 3H), 3.82 (q, 2H), 3.93 (s, 3H), 8.33 (s, 1H), 8.49 (d, 1H), 8.72 (d, 1H), 8.95-8.98 (m, 1H), 9.36 (s, 1H).

5-(Ethylsulphonyl)-N-methyl-6-[3-methyl-6-(trifluoromethyl)-3H-imidazo[4,5-c]pyridin-2-yl]pyridine-2-carbothioamide (Ex. 34)

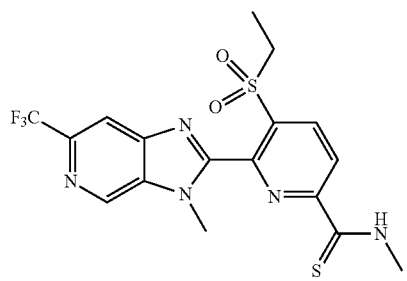 [SMILES: CCS(=O)(=O)c1ccc(C(=S)NC)nc1-c1nc2cc(C(F)(F)F)ncc2n1C]

20 mg (0.05 mmol) of 5-(ethylsulphonyl)-N-methyl-6-[3-methyl-6-(trifluoromethyl)-3H-imidazo[4,5-c]pyridin-2-yl]pyridine-2-carboxamide were initially charged in 2 ml of toluene, 8 mg (0.02 mmol) of Lawesson's reagent (4-methoxyphenyldithiophosphonic anhydride) were added and the mixture was stirred under reflux for 10 h. A further 8 mg (0.02 mmol) of Lawesson's reagent were then added and the reaction mixture was stirred at 106° C. for 16 h. A further 16 mg (0.04 mmol) of Lawesson's reagent were subsequently added and the reaction mixture was stirred at 106° C. for a further 16 h. The mixture was cooled to room temperature and concentrated under reduced pressure. The residue was purified by column chromatography using a water/acetonitrile gradient as mobile phase.

log P (neutral): 2.76; MH$^+$: 444; $^1$H-NMR (400 MHz, D$_6$-DMSO) δ ppm: 1.20 (t, 3H), 3.22 (d, 3H), 3.80 (q, 2H), 3.92 (s, 3H), 8.33 (s, 1H), 8.70 (d, 1H), 8.88 (d, 1H), 9.36 (s, 1H).

In analogy to the examples and according to the above-described preparation processes, the following compounds of the formula (I) can be obtained:

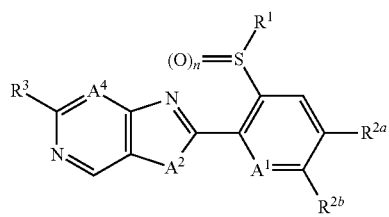

(I)

where the substituents $R^1$, $R^{2a}$, $R^{2b}$, $R^3$, $A^1$, $A^2$, $A^4$ and n have the meanings given in the table below:

| Ex. | $R^1$ | n | $A^4$ | $A^2$ | $A^1$ | $R^{2a}$ | $R^3$ | $R^{2b}$ |
|---|---|---|---|---|---|---|---|---|
| 1 | ethyl | 0 | CH | N-methyl | N | H | CF$_3$ |  cyclopropanecarbonylamino |
| 2 | ethyl | 1 | CH | N-methyl | N | H | CF$_3$ | 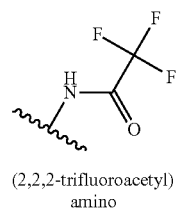 propanoylamino |
| 3 | ethyl | 2 | CH | N-methyl | N | H | CF$_3$ | (2,2,2-trifluoroacetyl)amino |
| 4 | ethyl | 2 | CH | N-methyl | N | H | CF$_3$ | 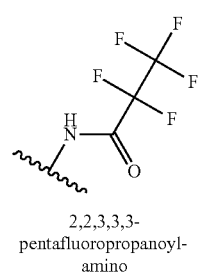 2,2,3,3,3-pentafluoropropanoylamino |
| 5 | ethyl | 2 | CH | N-methyl | N | H | CF$_3$ | 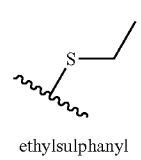 ethylsulphanyl |
| 6 | ethyl | 0 | CH | N-methyl | N | H | CF$_3$ | 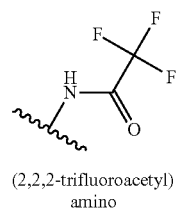 (2,2,2-trifluoroacetyl)amino |
| 7 | ethyl | 2 | CH | N-methyl | N | H | CF$_3$ | 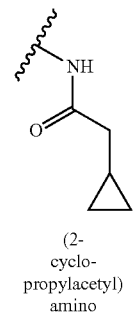 (2-cyclopropylacetyl)amino |

| Ex. | R¹ | n | A⁴ | A² | A¹ | R²ᵃ | R³ | R²ᵇ |
|---|---|---|---|---|---|---|---|---|
| 8 | ethyl | 2 | CH | N-methyl | N | H | CF₃ | 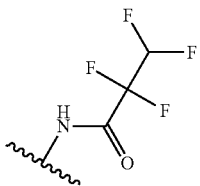<br>2,2,3,3-tetrafluoropropanoyl-amino |
| 9 | ethyl | 1 | CH | N-methyl | N | H | CF₃ | 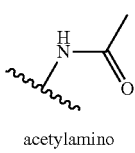<br>acetylamino |
| 10 | ethyl | 2 | CH | N-methyl | N | H | CF₃ | 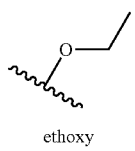 [SMILES: *OCC]<br>ethoxy |
| 12 | ethyl | 2 | CH | N-methyl | N | H | CF₃ | 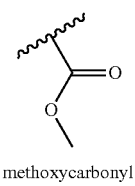 [SMILES: *C(=O)OC]<br>methoxycarbonyl |
| 13 | ethyl | 2 | CH | N-methyl | N | H | CF₃ | 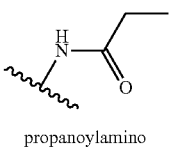<br>propanoylamino |
| 14 | ethyl | 2 | CH | N-methyl | N | H | CF₃ | 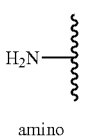<br>amino |
| 15 | ethyl | 2 | CH | N-methyl | N | H | CF₃ | 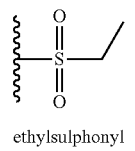<br>ethylsulphonyl |
| 16 | ethyl | 2 | CH | N-methyl | N | H | CF₃ | 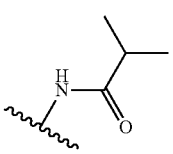<br>2-methylpropanoyl-amino |
| 17 | ethyl | 2 | CH | N-methyl | N | H | CF₃ | 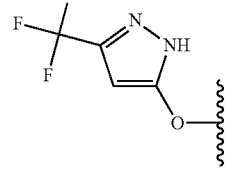<br>3-bis(trifluoromethyl)-1H-pyrazol-5-yl) |
| 18 | ethyl | 2 | CH | N-methyl | N | H | CF₃ | 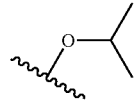<br>isopropoxy |
| 19 | ethyl | 0 | CH | N-methyl | N | H | CF₃ | 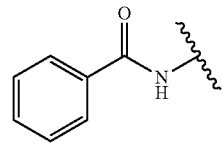<br>benzamido |
| 20 | ethyl | 2 | CH | N-methyl | N | H | CF₃ | 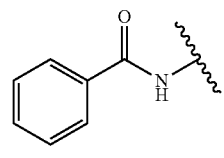<br>benzamido |
| 21 | ethyl | 2 | CH | N-methyl | N | H | CF₃ | 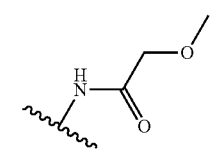<br>(2-methoxyacetyl)amino |
| 22 | ethyl | 2 | CH | N-methyl | N | H | CF₃ | 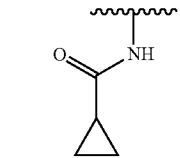<br>cyclopropane-carbonylamino |
| 24 | ethyl | 2 | CH | N-methyl | N | H | CF₃ | 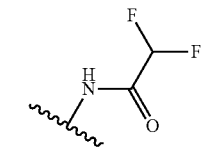<br>(2,2-difluoroacetyl)amino |

-continued

| Ex. | R¹ | n | A⁴ | A² | A¹ | R²ᵃ | R³ | R²ᵇ |
|---|---|---|---|---|---|---|---|---|
| 25 | ethyl | 2 | CH | N-methyl | N | H | CF₃ | 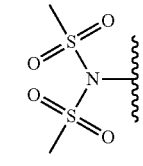 bis(methyl-sulphonyl)amino |
| 26 | ethyl | 2 | CH | N-methyl | N | H | CF₃ | methanesulphonamido |
| 27 | ethyl | 0 | CH | N-methyl | N | H | CF₃ | propanolyamino |
| 28 | ethyl | 2 | CH | N-methyl | N | H | CF₃ | methylsulphanyl |
| 29 | ethyl | 2 | CH | N-methyl | N | H | CF₃ | isopropylsulphanyl |
| 30 | ethyl | 2 | CH | N-methyl | N | H | CF₃ | benzylsulphanyl |
| 31 | ethyl | 2 | CH | N-methyl | N | H | CF₃ | 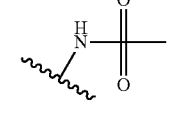 |
| 32 | ethyl | 2 | CH | N-methyl | N | H | CF₃ | 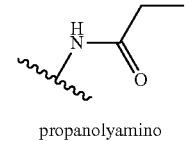 [SMILES: *NC(=O)CC] |
| 33 | ethyl | 2 | CH | N-methyl | N | H | CF₃ | 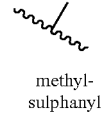 |
| 34 | ethyl | 2 | CH | N-methyl | N | H | CF₃ | 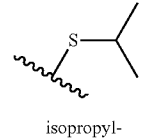 |
| 35 | ethyl | 2 | CH | N-methyl | N | H | CF₃ | 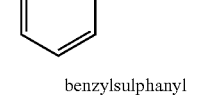 |
| 36 | ethyl | 2 | CH | N-methyl | N | H | CF₃ | 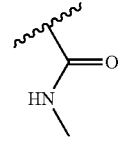 |
| 37 | ethyl | 2 | CH | N-methyl | N | H | CF₃ | 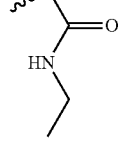 |
| 38 | ethyl | 2 | CH | N-methyl | N | H | CF₃ | |
| 39 | ethyl | 2 | CH | N-methyl | N | H | CF₃ | |
| 40 | ethyl | 2 | CH | N-methyl | N | H | CF₃ | |
| 41 | ethyl | 2 | CH | N-methyl | N | H | CF₃ | |
| 42 | ethyl | 2 | CH | N-methyl | N | H | CF₃ | |

| Ex. | R¹ | n | A⁴ | A² | A¹ | R²ᵃ | R³ | R²ᵇ |
|---|---|---|---|---|---|---|---|---|
| 43 | ethyl | 2 | CH | N-methyl | N | H | CF₃ | 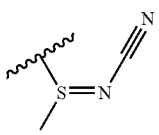 [SMILES: */S(C)=N\C#N] |
| 44 | ethyl | 2 | CH | N-methyl | N | H | CF₃ | 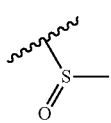 [SMILES: *S(C)=O] |
| 45 | ethyl | 2 | CH | N-methyl | N | H | CF₃ | 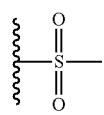 |
| 46 | ethyl | 2 | CH | N-methyl | N | H | CF₃ | 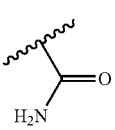 [SMILES: *C(N)=O] |
| 47 | ethyl | 2 | CH | N-methyl | N | H | CF₃ | 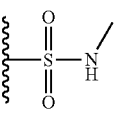 |
| 48 | ethyl | 2 | CH | N-methyl | N | H | CF₃ | 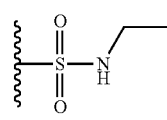 |
| 49 | ethyl | 2 | CH | N-methyl | N | H | CF₃ | 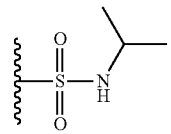 [SMILES: *S(=O)(=O)NC(C)C] |
| 50 | ethyl | 2 | CH | N-methyl | N | H | CF₃ | 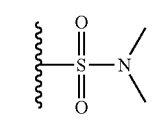 |
| 51 | ethyl | 2 | CH | N-methyl | N | H | CF₃ | 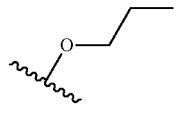 [SMILES: *OCCC] |
| 52 | ethyl | 2 | CH | N-methyl | N | H | CF₃ | 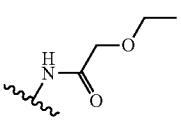 |
| 53 | ethyl | 2 | CH | N-methyl | N | H | CF₃ | 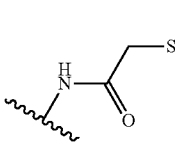 |
| 54 | ethyl | 2 | CH | N-methyl | N | H | CF₃ | 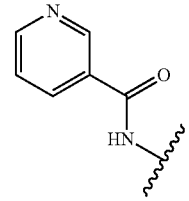 [SMILES: *NC(=O)c1cccnc1] |
| 55 | ethyl | 2 | CH | N-methyl | N | H | CF₃ | 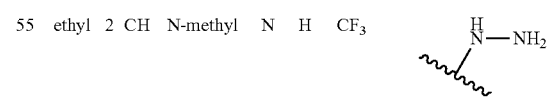 |
| 56 | ethyl | 2 | CH | N-methyl | N | H | CF₃ | 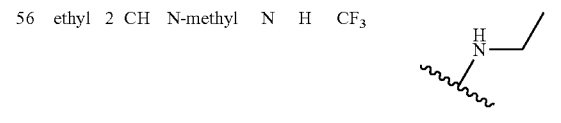 |
| 57 | ethyl | 2 | CH | N-methyl | N | H | CF₃ | 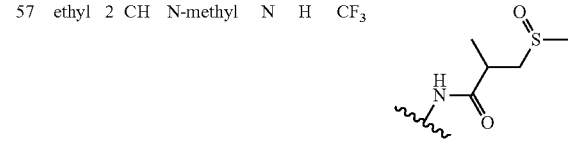 |
| 58 | ethyl | 2 | CH | N-methyl | N | H | CF₃ | 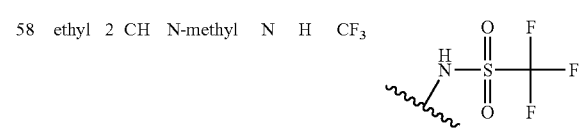 |
| 59 | ethyl | 2 | CH | N-methyl | N | H | CF₃ | 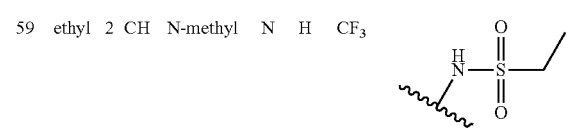 |
| 60 | ethyl | 2 | CH | N-methyl | N | H | CF₃ | 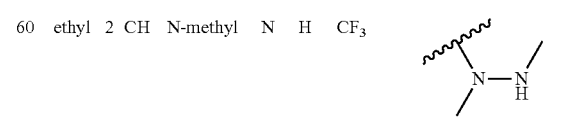 |
| 61 | ethyl | 2 | CH | N-methyl | N | H | CF₃ | 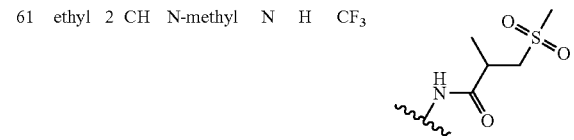 |
| 62 | ethyl | 2 | CH | N-methyl | N | H | C₂F₅ | 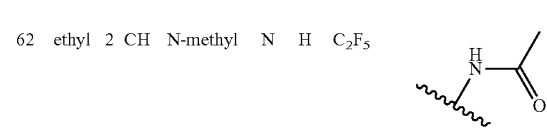 |
| 63 | ethyl | 2 | CH | N-methyl | N | H | CF₃ | 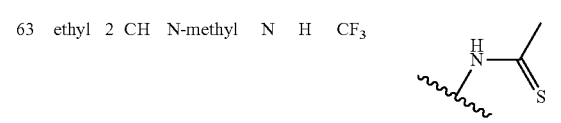 |
| 64 | ethyl | 2 | CH | N-methyl | N | H | CF₃ | 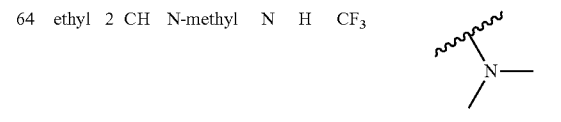 |

-continued

| Ex. | R¹ | n | A⁴ | A² | A¹ | R²ᵃ | R³ | R²ᵇ |
|---|---|---|---|---|---|---|---|---|
| 65 | ethyl | 2 | CH | N-methyl | N | H | CF₃ | 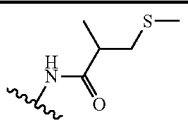 |
| 66 | ethyl | 2 | CH | N-methyl | N | H | CF₃ | 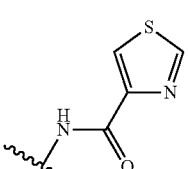 |
| 67 | ethyl | 2 | CH | N-methyl | N | H | C₂F₅ | 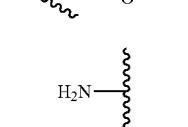 |
| 68 | ethyl | 2 | CH | N-methyl | N | H | CF₃ | 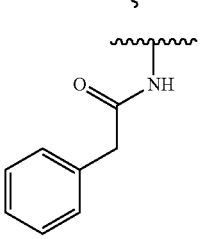 |
| 69 | ethyl | 2 | CH | N-methyl | N | H | CF₃ | 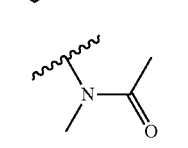 |
| 70 | ethyl | 2 | CH | N-methyl | N | H | CF₃ | 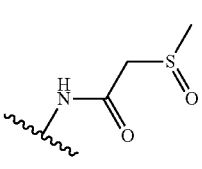 [SMILES: *NC(=O)CS(C)=O] |
| 71 | ethyl | 2 | CH | N-methyl | N | H | CF₃ | 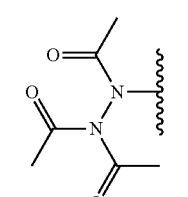 |
| 72 | ethyl | 2 | CH | N-methyl | N | H | CF₃ | 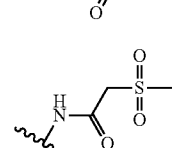 |
| 73 | ethyl | 2 | CH | N-methyl | N | H | CF₃ | 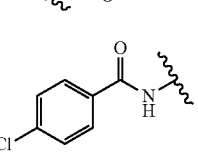 |
| 74 | ethyl | 2 | CH | N-methyl | N | H | CF₃ | 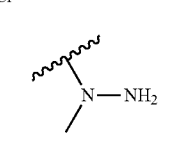 | where the bond to the remainder of the molecule is identified by a wavy line.

The log P values are measured according to EEC Directive 79/831 Annex V.A8 by HPLC (high-performance liquid chromatography) on a reversed-phase column (C18). Temperature: 55° C.

The LC-MS determination in the acidic range is effected at pH 2.7 using 0.1% aqueous formic acid and acetonitrile (contains 0.1% formic acid) as eluents, linear gradient from 10% acetonitrile to 95% acetonitrile. Called log P (HCOOH) in the table.

LC-MS determination in the neutral range is effected at pH 7.8 with 0.001 molar aqueous ammonium hydrogencarbonate solution and acetonitrile as eluents; linear gradient from 10% acetonitrile to 95% acetonitrile. Called log P (neutral) in the table.

Calibration is carried out using unbranched alkan-2-ones (having 3 to 16 carbon atoms) with known log P values (log P values determined on the basis of the retention times by linear interpolation between two successive alkanones).

The NMR data of selected examples are listed either in conventional form (δ values, multiplet splitting, number of hydrogen atoms) or as NMR peak lists.

In each case, the solvent in which the NMR spectrum is recorded is stated.

NMR Peak List Method

The ¹H NMR data of selected examples are stated in the form of ¹H NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore has the form of:
δ₁ (intensity₁); δ₂ (intensity₂); . . . ; δᵢ (intensityᵢ); . . . ; δₙ (intensityₙ)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of ¹H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the ¹H NMR peaks are similar to the conventional ¹H-NMR printouts and thus usually contain all peaks listed in a conventional NMR interpretation.

In addition, like conventional ¹H NMR printouts, they may show solvent signals, signals of stereoisomers of the target compounds which likewise form part of the subject-matter of the invention, and/or peaks of impurities.

In the reporting of compound signals within the delta range of solvents and/or water, our lists of ¹H NMR peaks show the standard solvent peaks, for example peaks of DMSO in DMSO-D₆ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional ¹H NMR interpretation.

Further details of ¹H NMR peak lists can be found in the Research Disclosure Database Number 564025.

| logP-neutral | logP-acidic | |
|---|---|---|
| 2.79 | 2.80 | Example 1: $^1$H-NMR(400.0 MHz, d$_6$-DMSO): = 11.055(2.7); 9.258(4.0); 8.289(2.9); 8.278(4.5); 8.267(3.5); 8.105(3.0); 8.083(2.4); 5.754(1.4); 3.982(16.0); 3.318(23.2); 2.964(1.2); 2.946(3.9); 2.928(4.0); 2.909(1.3); 2.671(0.5); 2.524(1.2); 2.507(53.8); 2.502(70.0); 2.498(52.2); 2.334(0.4); 2.329(0.5); 2.325(0.4); 2.004(0.6); 1.999(0.7); 1.988(1.7); 1.974(0.7); 1.968(0.7); 1.398(0.5); 1.175(0.9); 1.170(4.4); 1.151(9.1); 1.133(4.2); 0.864(3.8); 0.854(5.4); 0.836(2.7); 0.146(0.4); 0.008(3.3); 0.000(79.0); −0.149(0.4) |
| 2.25 | 2.33 | Example 2: $^1$H-NMR(400.0 MHz, d$_6$-DMSO): = 10.857(3.1); 9.323(4.4); 8.506(1.3); 8.484(5.1); 8.470(4.7); 8.448(1.2); 8.314(0.8); 8.304(4.8); 5.754(0.9); 4.370(16.0); 3.480(1.0); 3.461(1.1); 3.447(1.2); 3.428(1.1); 3.410(0.3); 3.318(56.2); 3.027(1.1); 3.009(1.3); 2.994(1.1); 2.976(1.0); 2.670(0.7); 2.540(1.8); 2.521(8.7); 2.502(111.6); 2.440(0.4); 2.329(0.7); 1.288(4.0); 1.269(8.3); 1.251(3.8); 1.148(4.2); 1.130(8.6); 1.111(4.0); 0.146(0.4); 0.000(73.5); −0.150(0.4) |
| 1.73 | 2.74 | Example 3: $^1$H-NMR(400.0 MHz, d$_6$-DMSO): = 12.789(2.8); 9.309(5.1); 9.278(0.4); 8.647(2.5); 8.625(3.2); 8.469(3.3); 8.447(2.6); 8.337(0.4); 8.317(6.2); 4.020(0.5); 3.988(1.4); 3.914(16.0); 3.838(0.9); 3.823(0.9); 3.735(1.3); 3.716(3.8); 3.698(3.9); 3.680(1.3); 3.319(67.3); 2.671(0.7); 2.501(105.6); 2.328(0.7); 1.988(0.5); 1.398(0.5); 1.236(0.4); 1.208(4.1); 1.190(8.3); 1.171(3.9); 0.000(0.8) |
| 1.94 | 3.17 | Example 4: $^1$H-NMR(400.0 MHz, d$_6$-DMSO): = 12.826(1.4); 9.304(5.0); 8.636(1.2); 8.614(1.7); 8.455(1.8); 8.432(1.5); 8.313(5.8); 5.753(0.3); 4.017(1.1); 3.911(16.0); 3.729(1.1); 3.710(3.1); 3.692(3.2); 3.673(1.1); 3.321(93.6); 3.318(98.7); 2.671(1.0); 2.506(132.9); 2.501(174.0); 2.497(132.9); 2.328(1.1); 1.206(4.2); 1.188(9.1); 1.169(4.2); 0.008(2.5); 0.000(59.6); −0.008(3.0) |
| 3.14 | 3.19 | Example 5: $^1$H-NMR(400.0 MHz, d$_6$-DMSO): = 9.289(4.5); 8.294(4.8); 8.264(3.0); 8.242(3.3); 7.832(3.3); 7.811(3.0); 5.754(3.6); 3.898(16.0); 3.736(1.1); 3.718(3.7); 3.700(3.6); 3.681(1.1); 3.321(59.9); 3.230(1.2); 3.211(3.9); 3.193(4.0); 3.175(1.3); 2.672(0.4); 2.502(66.8); 2.329(0.4); 1.322(4.3); 1.303(9.0); 1.285(4.2); 1.206(3.8); 1.187(8.2); 1.169(3.7); 0.000(19.2) |
|  | 3.18 | Example 6: $^1$H-NMR(400.0 MHz, d$_6$-DMSO): = 12.184(1.1); 9.269(4.4); 8.314(0.5); 8.291(4.8); 8.220(2.0); 8.198(3.3); 8.131(3.5); 8.109(2.2); 4.473(0.4); 4.037(16.0); 3.825(0.3); 3.318(99.5); 3.038(1.2); 3.019(3.9); 3.001(3.9); 2.983(1.3); 2.670(1.5); 2.506(175.4); 2.502(227.7); 2.498(180.7); 2.328(1.5); 1.215(4.3); 1.196(8.8); 1.178(4.1); 0.146(0.6); 0.008(8.0); 0.000(124.6); −0.150(0.6) |
| 2.66 | 2.71 | Example 7: $^1$H-NMR(400.0 MHz, d$_6$-DMSO): = 11.227(2.9); 9.288(4.2); 8.568(2.5); 8.546(4.5); 8.492(3.9); 8.469(2.3); 8.313(0.5); 8.297(4.6); 3.977(0.3); 3.871(16.0); 3.644(1.0); 3.626(3.4); 3.607(3.4); 3.589(1.0); 3.315(48.8); 2.675(0.6); 2.670(0.8); 2.666(0.6); 2.510(49.3); 2.506(95.9); 2.501(126.1); 2.497(94.3); 2.493(48.1); 2.364(4.6); 2.347(4.7); 2.332(0.7); 2.328(0.9); 2.324(0.7); 1.184(3.6); 1.166(8.0); 1.147(3.5); 1.086(0.6); 1.080(0.5); 1.076(0.5); 1.068(0.9); 1.056(0.6); 1.049(0.6); 1.037(0.3); 0.507(0.8); 0.497(2.4); 0.493(2.6); 0.488(1.3); 0.482(1.2); 0.476(2.4); 0.472(2.4); 0.462(0.9); 0.211(0.9); 0.198(3.0); 0.186(3.0); 0.174(0.7); 0.008(1.3); 0.000(29.8); −0.008(1.3) |
| 2.12 | 2.80 | Example 8: $^1$H-NMR(400.0 MHz, d$_6$-DMSO): = 12.509(2.2); 9.306(4.4); 9.276(0.5); 8.631(2.0); 8.609(2.6); 8.470(3.1); 8.448(2.5); 8.358(0.4); 8.336(0.5); 8.313(5.3); 7.899(0.4); 7.877(0.4); 7.026(0.5); 6.910(0.5); 6.898(1.0); 6.884(0.5); 6.769(0.5); 3.988(2.1); 3.913(16.0); 3.725(1.0); 3.707(3.3); 3.688(3.4); 3.670(1.0); 3.319(77.3); 3.317(79.9); 2.675(0.6); 2.670(0.8); 2.666(0.6); 2.506(98.6); 2.501(130.7); 2.497(99.3); 2.324(0.6); 1.205(3.7); 1.187(8.2); 1.168(3.6); 0.008(2.4); 0.000(59.0); −0.008(2.6) |
| 1.97 | 2.02 | Example 9: $^1$H-NMR(400.0 MHz, d$_6$-DMSO): = 10.912(4.0); 9.324(5.3); 9.155(0.4); 8.535(0.4); 8.523(0.5); 8.469(11.0); 8.302(5.5); 8.111(0.6); 7.145(0.9); 6.895(0.5); 4.371(16.0); 4.279(0.9); 3.483(1.3); 3.468(1.6); 3.451(1.8); 3.433(1.5); 3.418(0.9); 3.392(0.6); 3.370(2.1); 3.320(285.8); 3.317(258.5); 3.315(241.7); 3.247(1.1); 3.227(0.7); 3.045(0.6); 3.028(1.3); 3.010(1.5); 2.993(1.4); 2.976(1.1); 2.958(0.5); 2.720(0.4); 2.671(2.6); 2.635(0.7); 2.504(353.4); 2.500(340.8); 2.330(2.5); 2.257(0.7); 2.211(15.5); 1.372(7.6); 1.328(0.4); 1.290(4.6); 1.272(8.4); 1.254(4.3); 1.224(0.4); 0.000(6.6); −0.002(6.1) |
| 2.86 | 2.94 | Example 10: $^1$H-NMR(400.0 MHz, d$_6$-DMSO): = 9.285(4.3); 8.349(3.4); 8.326(3.6); 8.282(4.5); 7.312(3.6); 7.290(3.5); 5.754(7.8); 4.451(1.3); 4.434(4.2); 4.416(4.3); 4.399(1.3); 3.909(16.0); 3.719(1.1); 3.701(3.6); 3.682(3.6); 3.664(1.1); 3.319(1.9); 2.508(20.7); 2.503(27.3); 2.499(20.9); 1.370(4.3); 1.353(8.9); 1.335(4.2); 1.202(3.8); 1.184(8.1); 1.165(3.7); 0.008(1.8); 0.000(32.6); −0.008(1.7) |
| 2.17 | 2.17 | Example 12: $^1$H-NMR(400.0 MHz, d$_6$-DMSO): = 9.301(3.8); 9.282(0.4); 8.762(2.2); 8.741(2.7); 8.549(2.8); 8.528(2.3); 8.320(4.1); 8.263(0.4); 4.106(1.4); 3.959(14.0); 3.893(12.6); 3.837(1.0); 3.819(3.0); 3.801(3.0); 3.782(1.0); 3.721(1.4); 3.324(16.6); 2.504(32.9); 2.087(16.0); 1.220(3.2); 1.202(6.6); 1.183(3.1); 0.000(9.4) |
| 2.28 | 2.33 | Example 13: $^1$H-NMR(400.0 MHz, d$_6$-DMSO): = 11.265(3.2); 9.290(4.4); 9.279(0.4); 8.548(2.2); 8.525(4.5); 8.483(4.4); 8.470(0.4); 8.461(2.1); 8.312(0.6); 8.297(5.0); 4.454(0.8); 4.370(1.1); 3.978(1.3); 3.872(3.5); 3.648(1.0); 3.629(3.5); 3.611(3.6); 3.593(1.1); 3.314(110.7); 2.675(1.1); 2.670(1.4); 2.505(154.7); 2.501(204.1); 2.497(159.5); 2.481(7.8); 2.462(4.7); 2.443(1.6); 2.420(0.4); 2.328(1.3); 2.324(1.0); 1.269(0.5); 1.184(3.7); 1.165(8.1); 1.147(3.9); 1.129(0.7); 1.124(0.6); 1.107(4.4); 1.088(8.8); 1.069(4.0); 0.000(51.4) |
| 1.62 | 1.63 | Example 14: $^1$H-NMR(400.0 MHz, d$_6$-DMSO): = 9.231(4.1); 8.312(0.7); 8.241(4.3); 7.945(3.0); 7.922(3.2); 7.418(2.7); 6.769(3.3); 6.746(3.3); 3.824(16.0); 3.493(1.0); 3.475(3.3); 3.456(3.4); 3.438(1.0); 3.315(179.7); 2.675(1.0); 2.670(1.3); 2.666(1.0); 2.523(3.2); 2.510(71.6); 2.506(145.1); 2.501(198.3); 2.497(152.7); 2.492(78.5); 2.332(0.9); 2.328(1.3); 2.324(0.9); 1.150(3.4); 1.132(7.7); 1.114(3.4); 0.000(1.2) |
| 2.28 | 2.31 | Example 15: $^1$H-NMR(400.0 MHz, d$_6$-DMSO): = 9.325(4.3); 8.901(3.1); 8.880(3.5); 8.574(3.6); 8.554(3.2); 8.345(4.6); 8.314(0.9); 5.754(0.4); 4.036(0.8); 3.951(16.0); 3.933(1.2); 3.914(3.8); 3.908(1.7); 3.896(3.8); 3.877(1.1); 3.807(0.4); 3.770(0.4); 3.622(1.3); 3.604(4.0); 3.585(4.1); 3.567(1.4); 3.318(156.6); 2.670(1.6); 2.666(1.3); 2.541(0.9); 2.506(190.7); 2.501(253.5); 2.497(195.6); 2.332(1.2); 2.328(1.6); 2.324(1.3); 2.300(0.4); |

| logP-neutral | logP-acidic | |
|---|---|---|
| | | 1.261(4.0); 1.250(5.1); 1.242(9.2); 1.232(10.3); 1.224(4.7); 1.213(4.7); 1.198(1.0); 1.179(0.4); 1.066 (0.6); 0.008(1.0); 0.000(31.4) |
| 2.61 | 2.63 | Example 16: $^1$H-NMR(400.0 MHz, d$_6$-DMSO): = 11.270(3.0); 9.290(4.4); 8.562(2.4); 8.539(4.3); 8.482(3.9); 8.460(2.2); 8.313(0.6); 8.298(4.8); 3.873 (16.0); 3.638(1.0); 3.620(3.5); 3.601(3.5); 3.583(1.1); 3.316(60.6); 2.822(0.4); 2.805(1.1); 2.788 (1.5); 2.770(1.2); 2.754(0.5); 2.675(0.8); 2.671(1.0); 2.506(115.0); 2.501(150.5); 2.497(116.9); 2.333(0.7); 2.328(1.0); 1.988(1.0); 1.398(0.4); 1.193(0.5); 1.182(3.7); 1.163(8.1); 1.145(3.8); 1.127(15.7); 1.110(15.5); 1.066(0.7); 1.049(0.7); 0.146(1.0); 0.008(11.2); 0.000(191.8); −0.150 (1.0) |
| 2.69 | 2.77 | Example 17: $^1$H-NMR(400.0 MHz, d$_6$-DMSO): = 14.175(0.7); 14.137(0.6); 9.267(4.1); 8.614(0.5); 8.582(0.6); 8.564(0.5); 8.314(0.4); 8.276(4.9); 7.764(0.4); 7.747(0.4); 7.664(0.5); 7.647(0.4); 6.902(0.6); 6.680(0.5); 3.823(16.0); 3.800(2.1); 3.317 (74.3); 3.279(0.7); 2.671(1.3); 2.502(208.4); 2.328(1.4); 1.240(3.5); 1.222(7.3); 1.203(3.4); 0.000 (8.1) |
| 3.22 | 3.31 | Example 18: $^1$H-NMR(400.0 MHz, d$_6$-DMSO): = 9.281(4.1); 8.326(3.3); 8.304(3.5); 8.281(4.3); 7.256(3.7); 7.233(3.6); 5.754(8.8); 5.344(0.4); 5.329 (1.2); 5.314(1.6); 5.298(1.2); 5.283(0.5); 3.907(15.7); 3.703(1.0); 3.685(3.4); 3.666(3.5); 3.648 (1.0); 3.318(7.3); 2.511(13.3); 2.507(25.8); 2.503(34.4); 2.498(26.3); 2.494(13.6); 1.340(16.0); 1.325(15.9); 1.200(3.5); 1.182(7.8); 1.163(3.5); 0.008(2.1); 0.000(40.7); −0.008(2.0) |
| | 3.36 | Example 19: $^1$H-NMR(400.0 MHz, d$_6$-DMSO): = 11.039(3.2); 9.269(4.1); 8.396(2.8); 8.374(3.5); 8.287(4.4); 8.186(3.0); 8.164(2.5); 8.076(0.3); 8.037 (3.4); 8.019(3.8); 8.015(3.0); 7.634(0.8); 7.616(2.0); 7.597(1.6); 7.575(0.3); 7.570(0.4); 7.548 (2.8); 7.528(3.8); 7.510(1.6); 4.495(0.6); 4.248(0.4); 4.039(16.0); 4.021(0.4); 3.359(0.4); 3.318 (28.9); 3.273(0.5); 3.018(1.3); 2.999(3.9); 2.981(4.0); 2.963(1.3); 2.672(0.3); 2.535(0.8); 2.507(37.9); 2.502(48.8); 2.498(37.1); 1.989(0.9); 1.398(0.6); 1.312(0.4); 1.208(4.3); 1.190(8.9); 1.171 (4.2); 0.000(5.4) |
| | 2.98 | Example 20: $^1$H-NMR(400.0 MHz, d$_6$-DMSO): = 11.585(1.2); 11.233(3.8); 9.334(4.7); 9.311(1.5); 9.255(0.4); 8.685(0.8); 8.663(1.2); 8.580(1.0); 8.566(1.5); 8.558(5.8); 8.550(5.5); 8.528(1.0); 8.520(0.5); 8.513(0.4); 8.316(5.8); 8.247(0.4); 8.110 (0.5); 8.090(0.5); 8.074(0.5); 8.061(1.5); 8.042(1.5); 8.029(3.9); 8.010(4.0); 7.685(0.7); 7.666 (2.2); 7.648(1.9); 7.621(0.7); 7.604(3.1); 7.585(4.4); 7.566(1.3); 7.539(1.5); 7.520(0.6); 5.753(0.6); 4.494(1.2); 4.418(16.0); 3.928(4.9); 3.716(0.3); 3.698(1.1); 3.679(1.1); 3.661(0.4); 3.569(3.3); 3.523(1.0); 3.504(1.3); 3.490(1.2); 3.471(1.2); 3.453(0.4); 3.317(61.8); 3.082(0.3); 3.063 (1.1); 3.045(1.3); 3.030(1.1); 3.012(1.0); 2.945(0.4); 2.786(0.3); 2.672(0.8); 2.502(123.5); 2.329 (0.8); 1.958(0.4); 1.318(3.9); 1.299(8.3); 1.281(3.9); 1.254(0.8); 1.235(1.7); 1.220(1.5); 1.201 (2.7); 1.183(1.4); 0.000(0.6) |
| 2.17 | 2.22 | Example 21: $^1$H-NMR(400.0 MHz, d$_6$-DMSO): = 11.051(3.0); 9.292(4.2); 8.515(12.5); 8.313(0.6); 8.300(4.6); 5.753(2.1); 4.147(11.0); 4.108(0.6); 4.095(0.6); 3.987(1.7); 3.882(16.0); 3.678(1.1); 3.659(3.5); 3.641(3.5); 3.622(1.1); 3.368(22.6); 3.317(71.3); 3.289(0.6); 2.675(0.6); 2.671(0.8); 2.666(0.6); 2.506(88.1); 2.502(114.1); 2.497(86.6); 2.333(0.6); 2.328(0.7); 2.324(0.5); 1.236(0.6); 1.192(3.8); 1.174(8.3); 1.163(1.3); 1.155(3.7); 0.000(2.2) |
| 2.44 | 2.43 | Example 22: $^1$H-NMR(400.0 MHz, d$_6$-DMSO): = 11.621(2.7); 9.296(4.1); 8.527(2.1); 8.505(4.7); 8.469(4.1); 8.446(1.9); 8.314(0.6); 8.302(4.3); 5.754 (11.5); 3.906(0.3); 3.884(16.0); 3.649(1.0); 3.631(3.3); 3.612(3.4); 3.594(1.0); 3.317(132.9); 2.675(1.1); 2.670(1.5); 2.666(1.1); 2.523(4.1); 2.510(83.5); 2.506(168.8); 2.501(224.3); 2.497(167.2); 2.493(85.3); 2.332(1.0); 2.328(1.4); 2.324(1.1); 2.053(0.9); 2.037(1.2); 2.022(1.0); 1.235 (0.5); 1.183(3.7); 1.165(8.3); 1.146(3.6); 0.911(8.1); 0.896(5.7); 0.146(0.4); 0.008(3.0); 0.000(90.5); −0.008(4.1); −0.150(0.4) |
| 2.22 | 2.34 | Example 24: $^1$H-NMR(400.0 MHz, d$_6$-DMSO): = 12.166(1.9); 9.302(4.2); 8.603(2.1); 8.581(3.3); 8.507(3.0); 8.485(2.0); 8.311(4.7); 6.571(0.9); 6.437 (2.1); 6.304(1.0); 4.038(0.3); 4.020(0.4); 3.901(16.0); 3.709(1.0); 3.691(3.3); 3.672(3.4); 3.654 (1.0); 3.317(111.8); 2.675(0.7); 2.670(1.0); 2.666(0.8); 2.523(2.4); 2.506(126.6); 2.501(165.7); 2.497(120.3); 2.333(0.7); 2.328(1.0); 2.323(0.7); 1.988(1.5); 1.398(0.8); 1.202(3.6); 1.193(0.9); 1.183(8.2); 1.175(1.3); 1.165(3.6); 1.158(0.6); 0.937(0.5); 0.000(55.9); −0.008(2.2) |
| 2.44 | 2.47 | Example 25: $^1$H-NMR(400.0 MHz, d$_6$-DMSO): = 9.309(2.3); 8.805(1.7); 8.784(1.8); 8.365(1.9); 8.344(1.8); 8.329(2.5); 4.038(0.5); 4.020(0.5); 3.933 (0.6); 3.914(2.1); 3.896(10.3); 3.878(0.7); 3.739(16.0); 3.689(0.3); 3.317(76.1); 2.675(0.5); 2.670 (0.6); 2.506(84.8); 2.501(106.0); 2.497(77.1); 2.328(0.7); 2.323(0.5); 1.988(2.0); 1.398(0.7); 1.261(2.1); 1.243(4.5); 1.224(2.0); 1.193(0.5); 1.175(1.0); 1.157(0.5); 0.000(23.4) |
| 0.85 | 1.92 | Example 26: $^1$H-NMR(400.0 MHz, d$_6$-DMSO): = 11.715(1.1); 9.288(5.0); 9.264(0.3); 8.418(3.1); 8.396(3.3); 8.313(0.5); 8.304(0.4); 8.290(5.3); 7.858 (0.5); 7.795(0.5); 7.790(0.3); 7.354(3.1); 7.332(3.1); 5.753(8.5); 4.030(1.2); 3.924(16.0); 3.903 (1.2); 3.824(0.5); 3.815(1.5); 3.771(1.1); 3.753(3.5); 3.734(3.6); 3.716(1.2); 3.338(19.8); 3.323 (127.2); 3.296(2.4); 3.186(0.5); 2.670(1.3); 2.505(164.3); 2.501(213.6); 2.497(163.7); 2.328(1.3); 2.291(0.8); 1.234(1.1); 1.216(3.8); 1.198(8.3); 1.179(3.9); 1.166(0.5); 0.000(0.9) |
| 2.62 | 2.73 | Example 27: $^1$H-NMR(601.6 MHz, CD3CN): = 9.045(2.5); 8.786(0.6); 8.328(2.0); 8.313(2.2); 8.130(2.7); 8.129(2.7); 7.978(2.1); 7.963(2.0); 3.961 (16.0); 2.935(1.2); 2.922(3.7); 2.910(3.7); 2.898(1.2); 2.454(1.2); 2.441(3.7); 2.429(3.8); 2.416 (1.2); 2.129(4.4); 1.963(2.9); 1.955(1.1); 1.951(1.3); 1.947(7.1); 1.943 (12.0); 1.939(17.0); 1.935 (11.9); 1.931(6.1); 1.212(4.0); 1.200(8.3); 1.188(3.9); 1.168(4.0); 1.155(8.2); 1.143(3.9); 0.005 (0.6); 0.000(16.0); −0.006(0.5) |
| 2.75 | 2.81 | Example 28: $^1$H-NMR(400.0 MHz, d$_6$-DMSO): = 9.292(3.9); 8.293(4.1); 8.280(3.1); 8.258(3.4); 7.859(3.4); 7.838(3.1); 5.754(6.7); 3.903(15.8); 3.751 (1.0); 3.732(3.4); 3.714(3.4); 3.695(1.0); 3.328(12.7); 2.601(16.0); 2.525(0.6); 2.511(14.8); 2.507 |

| logP-neutral | logP-acidic | |
|---|---|---|
| | | (29.4); 2.503(38.5); 2.498(28.3); 1.208(3.6); 1.190(7.9); 1.171(3.5); 0.008(0.5); 0.000(14.0); −0.008(0.6) |
| 3.53 | 3.62 | Example 29: $^1$H-NMR(400.0 MHz, d$_6$-DMSO): δ = 9.287(3.9); 8.313(2.4); 8.294(4.2); 8.257(3.1); 8.235(3.4); 7.832(0.3); 7.811(0.3); 7.800(3.3); 7.779 (3.1); 5.753(0.6); 4.027(0.5); 4.010(1.1); 3.993(1.5); 3.976(1.1); 3.959(0.4); 3.898(16.0); 3.726 (1.0); 3.708(3.1); 3.689(3.3); 3.671(1.1); 3.361(1.1); 3.319(609.0); 3.317(609.5); 3.210(0.4); 3.192 (0.4); 2.989(0.3); 2.674(4.6); 2.670(6.4); 2.666(4.7); 2.523(18.1); 2.510(391.4); 2.506(789.6); 2.501(1038.8); 2.497(748.5); 2.492(361.9); 2.458(1.0); 2.454(0.7); 2.449(0.6); 2.395(0.4); 2.332 (4.4); 2.328(6.3); 2.323(4.7); 1.371(15.1); 1.354(15.0); 1.321(0.4); 1.302(0.8); 1.285(0.4); 1.235 (0.4); 1.203(3.7); 1.184(7.9); 1.166(3.5); 0.974(0.7); 0.957(0.4); 0.146(0.9); 0.008(7.7); 0.000(215.6); −0.008(7.9); −0.150(1.0) |
| 3.72 | 3.81 | Example 30: $^1$H-NMR(400.0 MHz, d$_6$-DMSO): δ = 9.292(4.1); 8.303(4.4); 8.283(3.3); 8.261(3.7); 7.878(3.6); 7.857(3.4); 7.385(1.8); 7.381(2.3); 7.364 (3.2); 7.362(3.2); 7.309(0.9); 7.303(1.2); 7.299(0.6); 7.287(3.7); 7.268(3.2); 7.262(2.4); 7.259 (1.3); 7.253(0.6); 7.245(1.3); 7.228(0.4); 5.754(1.9); 4.491(8.1); 3.809(16.0); 3.722(1.0); 3.704(3.4); 3.685(3.4); 3.667(1.0); 3.318(57.9); 2.675(0.4); 2.671(0.6); 2.666(0.4); 2.524(1.5); 2.510(32.7); 2.506(65.0); 2.502(86.3); 2.497(64.0); 2.493(32.2); 2.333(0.4); 2.328(0.5); 2.324(0.4); 1.197 (3.6); 1.179(8.1); 1.170(1.0); 1.160(3.6); 0.000(4.0) |
| 1.96 | 2.01 | Example 31: $^1$H-NMR(400.0 MHz, d$_6$-DMSO): δ = 9.362(3.9); 8.978(1.0); 8.966(1.0); 8.954(0.4); 8.727(3.2); 8.706(3.9); 8.503(3.8); 8.483(3.3); 8.328 (4.2); 5.754(2.3); 3.931(16.0); 3.872(1.0); 3.844(1.0); 3.826(3.4); 3.807(3.5); 3.789(1.0); 3.319 (32.9); 3.117(0.9); 2.891(0.8); 2.844(7.2); 2.832(7.2); 2.732(0.6); 2.671(0.4); 2.541(3.4); 2.524 (0.9); 2.511(21.8); 2.506(44.8); 2.502(59.4); 2.497(43.0); 2.493(20.7); 2.328(0.4); 2.102(0.4); 1.224 (3.7); 1.206(8.2); 1.187(3.6); 1.176(0.3); 1.158(0.5); 0.146(0.4); 0.008(3.1); 0.000(87.0); −0.009 (3.0); −0.150(0.4) |
| 2.22 | 2.29 | Example 32: $^1$H-NMR(400.0 MHz, d$_6$-DMSO): δ = 9.360(4.4); 9.051(0.7); 9.037(1.4); 9.022(0.7); 8.725(3.0); 8.704(3.6); 8.506(3.6); 8.486(3.1); 8.327 (4.7); 5.753(1.9); 3.928(16.0); 3.837(1.1); 3.818(3.5); 3.800(3.6); 3.781(1.1); 3.373(0.6); 3.356 (2.1); 3.339(3.2); 3.320(72.2); 2.671(0.4); 2.541(2.9); 2.506(45.8); 2.502(59.8); 2.497(45.5); 2.329 (0.4); 1.221(3.7); 1.202(8.2); 1.184(3.7); 1.134(4.0); 1.116(8.5); 1.098(3.9); 0.000(65.2) |
| 2.27 | 2.34 | Example 33: $^1$H-NMR(400.0 MHz, d$_6$-DMSO): δ = 9.343(4.4); 8.931(1.6); 8.919(1.6); 8.719(4.6); 8.706(0.4); 8.698(5.7); 8.496(5.2); 8.487(0.3); 8.475 (4.5); 8.326(0.3); 8.317(5.2); 8.308(8.0); 5.750(2.3); 3.926(0.8); 3.899(16.0); 3.828(1.0); 3.810 (3.1); 3.791(3.2); 3.773(1.0); 3.375(106.8); 3.370(117.3); 3.365(96.6); 3.357(111.1); 3.352(103.8); 2.957(0.5); 2.948(0.6); 2.938(1.0); 2.928(0.9); 2.922(0.7); 2.918(0.5); 2.910(0.5); 2.673(0.4); 2.543(4.0); 2.527(1.0); 2.522(1.5); 2.513(24.4); 2.509(52.2); 2.504(70.6); 2.500(50.9); 2.495(24.0); 2.331(0.4); 1.215(4.3); 1.197(9.8); 1.178(4.2); 1.116(0.5); 0.742(0.7); 0.722(2.2); 0.712(2.2); 0.709(1.7); 0.705(1.8); 0.703(2.2); 0.695(1.8); 0.682(1.7); 0.670(3.4); 0.663(2.1); 0.642(0.4); 0.008 (1.8); 0.000(56.8); −0.009(1.8) |
| 2.76 | 2.80 | Example 34: $^1$H-NMR(400.0 MHz, d$_6$-DMSO): δ = 10.989(0.7); 10.977(0.7); 9.359(3.7); 8.895(3.3); 8.874(4.2); 8.713(4.1); 8.691(3.4); 8.330(3.9); 8.329(4.0); 8.313(0.4); 3.923(16.0); 3.823(1.0); 3.804(3.4); 3.786(3.6); 3.773(1.4); 3.767(1.2); 3.751 (0.4); 3.329(41.3); 3.221(7.1); 3.209(7.1); 2.679(0.3); 2.675(0.7); 2.670(1.0); 2.666(0.7); 2.661 (0.3); 2.524(2.2); 2.519(3.3); 2.510(57.4); 2.506(123.4); 2.501(167.3); 2.497(119.6); 2.492(56.2); 2.333(0.7); 2.328(1.0); 2.323(0.7); 2.319(0.3); 2.086(15.2); 1.223(3.6); 1.204(8.2); 1.186(3.5); 0.850(0.4); 0.832(0.5); 0.008(0.5); 0.000(18.5); −0.009(0.6) |
| 3.14 | 3.17 | Example 35: $^1$H-NMR(400.0 MHz, d$_6$-DMSO): δ = 10.967(1.0); 9.355(3.8); 8.870(3.2); 8.849(4.1); 8.706(4.0); 8.685(3.3); 8.329(4.2); 8.312(4.0); 3.988 (0.4); 3.923(16.0); 3.831(0.8); 3.824(1.3); 3.813(2.0); 3.806(3.9); 3.797(2.5); 3.787(4.0); 3.781 (2.1); 3.769(1.4); 3.568(0.4); 3.486(0.4); 3.446(0.7); 3.421(0.8); 3.320(1076.7); 3.237(0.5); 3.220 (0.5); 2.942(0.5); 2.675(7.6); 2.670(10.6); 2.666(8.0); 2.620(0.5); 2.593(0.6); 2.570(0.9); 2.523 (25.4); 2.519(39.7); 2.510(621.7); 2.506(1328.0); 2.501(1803.9); 2.497(1319.3); 2.492(643.5); 2.376(0.4); 2.332(7.7); 2.328(10.7); 2.323(8.1); 2.153(0.5); 1.231(4.0); 1.221(4.0); 1.213(8.7); 1.202(8.3); 1.195(4.3); 1.184(3.5); 1.044(1.7); 1.029(1.6); 0.146(0.4); 0.008(2.9); 0.000(98.7); −0.008 (4.2); −0.150(0.6); −3.075(0.4) |
| 3.14 | 3.17 | Example 36: $^1$H-NMR(400.0 MHz, d$_6$-DMSO): δ = 15.381(0.4); 12.894(0.4); 10.721(0.9); 10.710(0.7); 9.355(0.5); 9.334(3.9); 8.799(1.1); 8.778(1.4); 8.706(0.4); 8.684(2.8); 8.663(1.8); 8.316(4.5); 8.313(4.8); 7.092(0.4); 6.585(0.4); 5.854(0.4); 3.949 (0.4); 3.932(0.4); 3.924(1.3); 3.899(16.0); 3.872(0.8); 3.825(1.2); 3.807(3.6); 3.788(3.6); 3.770 (1.2); 3.750(0.4); 3.734(0.5); 3.717(0.5); 3.714(0.4); 3.671(0.4); 3.655(0.8); 3.639(0.4); 3.628 (0.4); 3.599(0.5); 3.594(0.5); 3.575(0.7); 3.563(0.7); 3.539(1.0); 3.520(1.1); 3.488(0.6); 3.465(0.9); 3.450(0.9); 3.440(1.0); 3.374(3.1); 3.323(1222.9); 3.320(1042.7); 3.256(0.5); 3.233(0.4); 2.942 (1.2); 2.675(8.0); 2.670(11.5); 2.666(8.5); 2.661(4.3); 2.627(0.4); 2.604(0.4); 2.581(0.7); 2.578(0.7); 2.524(26.8); 2.519(42.0); 2.510(664.6); 2.506(1423.0); 2.501(1930.0); 2.497(1406.8); 2.492 (681.2); 2.419(0.8); 2.401(0.8); 2.391(0.6); 2.370(0.4); 2.366(0.5); 2.337(3.7); 2.332(8.0); 2.328 (11.5); 2.324(8.4); 2.281(0.4); 2.266(0.5); 2.155(1.4); 2.142(0.4); 2.085(0.4); 2.073(1.0); 1.642(0.4); 1.216(3.8); 1.197(8.4); 1.179(3.7); 1.116(0.5); 1.099(0.4); 1.045(0.4); 1.030(0.5); 0.909(2.5); 0.890(4.6); 0.146(0.6); 0.008(3.0); 0.000(102.0); −0.008(4.2); −0.149(0.6); −2.987(0.4); −3.401 (0.4) |
| 2.02 | 2.03 | Example 37: $^1$H-NMR(400.0 MHz, d$_6$-DMSO): δ = 9.304(3.6); 8.830(3.6); 8.809(4.0); 8.392(3.9); 8.371(3.7); 8.317(3.8); 8.315(4.0); 8.146(2.2); 3.897 (16.0); 3.871(0.8); 3.854(1.7); 3.835(1.9); 3.833(2.0); 3.814(1.8); 3.797(0.7); 3.779(0.4); 3.331 (5.1); 3.313(4.0); 3.297(2.9); 3.278(2.1); 3.260(0.9); 3.054(0.3); 3.036(1.1); 3.017(1.3); 3.001(1.1); 2.983(0.9); 2.525(0.5); 2.520(0.8); 2.512(13.9); 2.507(30.0); 2.503(40.8); 2.498(29.8); 2.494 (14.6); 2.086(6.3); 1.239(3.5); 1.221(8.0); 1.202(3.5); 1.134(3.7); 1.116(8.3); 1.097(3.6); 0.000(2.8 |

-continued

| logP-neutral | logP-acidic | |
|---|---|---|
| 2.03 | 2.05 | Example 38: $^1$H-NMR(400.0 MHz, d$_6$-DMSO): δ = 9.241(7.9); 8.313(0.5); 8.242(8.2); 7.955(1.4); 7.915(0.8); 6.808(3.5); 6.785(3.4); 5.754(3.0); 3.859 (16.0); 3.544(1.3); 3.526(3.9); 3.507(3.9); 3.489(1.3); 3.318(133.2); 2.851(11.1); 2.839(11.5); 2.675(0.8); 2.671(1.1); 2.666(0.9); 2.524(3.6); 2.510(58.4); 2.506(123.6); 2.501(174.1); 2.497(134.5); 2.493(68.8); 2.337(0.3); 2.333(0.7); 2.328(1.0); 2.324(0.8); 1.162(6.4); 1.144(14.5); 1.125 (6.2); 0.008(1.1); 0.000(36.8); −0.008(1.7) |
| 2.66 | 2.66 | Example 39: $^1$H-NMR(600.1 MHz, d$_6$-DMSO): δ = 9.328(3.1); 8.693(3.6); 8.679(3.9); 8.357(3.4); 8.355(3.3); 8.063(3.7); 8.049(3.8); 7.305(0.5); 7.303 (0.7); 7.294(3.8); 7.292(1.9); 7.290(1.7); 7.283(2.4); 7.277(0.5); 7.274(0.7); 7.268(0.5); 7.078 (1.9); 7.075(2.2); 7.065(1.7); 7.062(1.9); 5.756(14.8); 4.575(1.7); 4.552(1.9); 4.278(2.1); 4.256(1.8); 3.909(16.0); 3.846(0.5); 3.833(0.8); 3.822(1.4); 3.810(1.5); 3.798(1.5); 3.786(1.5); 3.775(0.8); 3.762(0.5); 3.320(133.6); 2.617(0.3); 2.613(0.5); 2.610(0.3); 2.541(2.9); 2.523(0.8); 2.519(1.0); 2.516(1.0); 2.508(22.7); 2.505(50.4); 2.501(70.3); 2.498(50.6); 2.495(23.6); 2.385(0.4); 1.352(0.5); 1.235(0.6); 1.210(0.4); 1.202(3.3); 1.197(1.0); 1.189(7.5); 1.177(3.3); 0.000(1.5) |
| 3.24 | 3.33 | Example 40: $^1$H-NMR(400.0 MHz, d$_6$-DMSO): δ = 9.280(3.8); 8.398(3.1); 8.377(3.4); 8.279(4.1); 7.833(3.2); 7.812(2.9); 6.820(2.1); 6.781(3.1); 6.632 (1.5); 6.608(1.5); 6.594(1.0); 6.569(1.0); 5.754(4.6); 3.888(0.5); 3.859(16.0); 3.722(1.0); 3.704 (3.3); 3.686(3.3); 3.667(1.0); 3.318(43.7); 2.671(0.4); 2.524(0.9); 2.511(23.5); 2.506(50.0); 2.502 (67.8); 2.497(48.8); 2.493(23.1); 2.329(0.4); 1.761(0.4); 1.750(0.6); 1.738(0.6); 1.726(0.6); 1.716 (0.4); 1.195(3.5); 1.176(7.9); 1.158(3.4); 0.956(0.5); 0.946(1.7); 0.940(1.9); 0.926(1.7); 0.920 (1.8); 0.910(0.6); 0.689(0.7); 0.679(2.1); 0.673(2.0); 0.668(2.0); 0.662(2.1); 0.652(0.5); 0.146(0.4); 0.008(3.4); 0.000(97.3); −0.009(3.3); −0.150(0.4) |
| 1.79 | 1.78 | Example 41: $^1$H-NMR(600.1 MHz, d$_6$-DMSO): δ = 9.321(3.9); 8.855(3.1); 8.841(3.4); 8.547(3.4); 8.533(3.2); 8.335(4.2); 8.244(0.9); 8.241(0.4); 8.232 (0.3); 8.229(0.9); 7.901(1.0); 7.890(0.4); 7.887(0.9); 5.756(8.0); 3.940(16.0); 3.911(1.2); 3.899 (3.7); 3.886(3.7); 3.874(1.2); 3.510(0.4); 3.496(0.5); 3.484(0.9); 3.472(1.3); 3.460(2.0); 3.448(2.3); 3.436(2.3); 3.423(2.0); 3.412(1.2); 3.399(0.8); 3.387(0.5); 2.541(O.7); 2.523(0.5); 2.520(0.6); 2.517(0.7); 2.505(34.7); 2.502(47.3); 2.499(36.2); 2.386(0.3); 1.352(0.6); 1.259(0.5); 1.248(4.0); 1.235(9.1); 1.223(4.0); 1.202(4.2); 1.190(8.8); 1.178(4.2); 0.000(6.4) |
| 3.64 | 3.68 | Example 42: $^1$H-NMR(600.1 MHz, d$_6$-DMSO): δ = 9.262(1.7); 9.255(3.2); 8.455(0.7); 8.440(0.8); 8.319(3.6); 8.305(3.9); 8.291(1.7); 8.290(1.7); 8.280 (3.5); 8.279(3.4); 8.265(0.9); 8.251(0.8); 7.735(1.8); 7.732(3.7); 7.729(1.0); 7.727(1.3); 7.724 (1.7); 7.719(2.8); 7.585(0.5); 7.582(0.9); 7.581(0.8); 7.577(4.4); 7.574(4.2); 7.569(1.7); 7.568(1.6); 7.565(2.3); 7.559(0.5); 7.557(0.7); 7.434(3.5); 7.419(3.7); 5.756(5.3); 3.815(0.8); 3.785(16.0); 3.775(7.9); 3.742(1.1); 3.729(3.3); 3.722(1.2); 3.717(3.4); 3.709(1.1); 3.705(1.1); 3.697(0.4); 3.338 (0.5); 3.322(754.8); 2.619(0.5); 2.617(1.1); 2.613(1.5); 2.610(1.1); 2.607(0.5); 2.541(0.5); 2.522 (2.7); 2.519(3.3); 2.516(3.1); 2.508(76.3); 2.504(169.4); 2.501 (236.4); 2.498(170.4); 2.495(79.6); 2.391(0.5); 2.388(1.1); 2.385(1.5); 2.382(1.1); 2.379(0.5); 1.235(0.4); 1.185(3.4); 1.173(7.7); 1.161(3.6); 1.158(2.3); 1.145(4.0); 1.133(1.7); 0.000(3.3) |
| 1.75 | 1.75 | Example 43: $^1$H-NMR(400.0 MHz, d$_6$-DMSO): δ = 9.333(4.4); 9.227(0.8); 8.901(3.3); 8.880(3.7); 8.576(3.8); 8.555(3.5); 8.338(4.7); 8.314(0.9); 8.238 (0.9); 7.954(1.3); 5.754(6.0); 4.325(0.6); 3.977(16.0); 3.944(0.9); 3.926(1.9); 3.915(2.0); 3.908 (2.0); 3.897(2.4); 3.873(3.4); 3.862(0.5); 3.749(0.5); 3.550(0.7); 3.536(1.5); 3.513(0.4); 3.343(131.0); 3.291(17.6); 3.210(0.5); 2.946(0.5); 2.675(1.9); 2.671(2.5); 2.666(1.9); 2.592(0.4); 2.506 (292.8); 2.501(404.5); 2.497(314.3); 2.332(1.7); 2.328(2.4); 2.324(1.8); 1.261(3.7); 1.243(8.0); 1.225 (3.7); 1.169(0.8); 1.150(1.6); 1.141(0.4); 1.132(0.7); 0.008(2.7); 0.000(70.8); −0.149(0.3) |
| 1.81 | 1.81 | Example 44: $^1$H-NMR(400.0 MHz, d$_6$-DMSO): δ = 9.304(3.6); 8.840(3.5); 8.819(3.9); 8.441(3.9); 8.420(3.6); 8.317(3.8); 8.316(3.8); 5.754(6.1); 3.913 (15.6); 3.904(0.8); 3.886(0.7); 3.869(1.6); 3.850(1.6); 3.845(1.6); 3.827(1.6); 3.809(0.7); 3.791 (0.4); 3.317(37.6); 2.947(16.0); 2.671(0.4); 2.524(1.0); 2.520(1.4); 2.511(21.6); 2.506(46.0); 2.502 (64.6); 2.497(47.9); 2.493(22.6); 2.329(0.4); 1.246(3.3); 1.228(7.5); 1.209(3.2); 0.008(0.4); 0.000 (13.9); −0.009(0.4) |
| 2.08 | 2.08 | Example 45: $^1$H-NMR(400.0 MHz, d$_6$-DMSO): δ = 9.330(4.6); 8.902(3.2); 8.882(3.6); 8.566(3.7); 8.545(3.3); 8.347(4.9); 8.313(0.4); 5.753(6.3); 3.966 (16.0); 3.947(1.1); 3.928(3.6); 3.910(3.7); 3.891(1.1); 3.441(17.8); 3.316(79.8); 2.670(1.1); 2.505 (129.2); 2.501(178.4); 2.497(144.2); 2.328(1.0); 1.264(3.8); 1.245(8.1); 1.227(3.8); 0.000(26.6) |
| 1.68 | 1.78 | Example 46: $^1$H-NMR(400.0 MHz, d$_6$-DMSO): δ = 9.349(2.8); 9.240(0.4); 8.723(2.2); 8.702(2.7); 8.505(2.6); 8.484(2.3); 8.372(1.1); 8.326(3.0); 8.004 (1.0); 4.254(0.3); 4.074(1.8); 3.941(10.7); 3.901(0.5); 3.866(0.7); 3.848(2.2); 3.829(2.3); 3.811 (0.7); 3.338(82.0); 2.675(0.5); 2.670(0.6); 2.666(0.5); 2.599(0.4); 2.523(1.5); 2.510(36.5); 2.506 (76.7); 2.501(107.5); 2.497(81.7); 2.493(40.2); 2.333(0.4); 2.328(0.6); 2.323(0.5); 2.086(16.0); 1.230(2.6); 1.212(5.5); 1.193(2.4); 0.008(1.3); 0.000(36.3); −0.008(1.4) |
| 2.08 | 2.15 | Example 47: $^1$H-NMR(400.0 MHz, d$_6$-DMSO): δ = 9.341(4.3); 8.835(3.3); 8.814(3.8); 8.438(3.8); 8.418(3.5); 8.340(4.5); 8.156(1.8); 5.754(4.2); 3.946 (16.0); 3.906(1.1); 3.888(3.6); 3.870(3.6); 3.851(1.1); 3.320(73.5); 2.671(0.4); 2.613(13.0); 2.510 (23.0); 2.506(46.6); 2.502(64.2); 2.497(49.8); 2.328(0.4); 1.254(3.6); 1.235(8.1); 1.217(3.6) |
| 2.30 | 2.36 | Example 48: $^1$H-NMR(400.0 MHz, d$_6$-DMSO): δ = 9.350(4.3); 8.836(3.4); 8.815(3.8); 8.448(3.8); 8.428(3.5); 8.349(4.6); 8.321(0.3); 8.281(1.4); 5.762 (5.4); 3.945(16.0); 3.901(1.0); 3.882(3.5); 3.864(3.6); 3.845(1.1); 3.327(142.0); 3.028(1.3); 3.016 (1.3); 2.684(0.5); 2.679(0.7); 2.675(0.5); 2.514(81.0); 2.510(111.1); 2.505(83.9); 2.341(0.5); 2.337(0.7); 2.332(0.5); 1.255(3.7); 1.237(8.1); 1.218(3.6); 1.034(4.4); 1.016(9.2); 0.998(4.3) |
| 2.49 | 2.56 | Example 49: $^1$H-NMR(400.0 MHz, d$_6$-DMSO): δ = 9.350(4.5); 8.833(3.3); 8.812(3.8); 8.456(3.8); 8.436(3.5); 8.351(4.8); 8.321(0.4); 8.288(1.2); 5.761 (2.2); 3.944(0.6); 3.932(16.0); 3.863(1.1); 3.845(3.5); 3.826(3.6); 3.808(1.1); 3.534(0.6); 3.519 |

| logP-neutral | logP-acidic | |
|---|---|---|
| | | (0.6); 3.445(0.3); 3.327(111.7); 2.683(0.5); 2.678(0.7); 2.674(0.5); 2.532(1.6); 2.514(78.6); 2.509 (108.3); 2.505(82.7); 2.340(0.5); 2.336(0.6); 2.332(0.5); 1.241(3.8); 1.222(8.1); 1.204(3.6); 1.024 (14.8); 1.008(14.7) |
| 2.47 | 2.54 | Example 50: $^1$H-NMR(400 MHz, d$_6$-DMSO): □ = 9.312(2.0); 8.848(1.5); 8.827(1.6); 8.439(1.6); 8.418(1.5); 8.342(2.1); 5.761(1.7); 3.969(7.2); 3.907 (0.5); 3.889(1.6); 3.870(1.6); 3.852(0.5); 3.327(29.3); 2.885(16.0); 2.514(20.6); 2.510(28.2); 2.505 (21.7); 1.262(1.7); 1.244(3.6); 1.225(1.6) |
| 3.36 | 3.37 | Example 51: $^1$H-NMR(601.6 MHz, d$_6$-DMSO): □ = 9.284(3.3); 8.345(3.5); 8.330(3.7); 8.288(3.6); 8.286(3.5); 7.322(3.6); 7.307(3.7); 5.756(5.7); 4.423 (1.5); 4.336(2.3); 4.325(5.1); 4.314(2.4); 3.905(16.0); 3.707(0.9); 3.695(3.2); 3.682(3.3); 3.670 (1.0); 3.326(167.7); 2.614(0.3); 2.523(0.6); 2.520(0.7); 2.517(0.7); 2.508(18.0); 2.505(37.8); 2.502 (50.9); 2.499(37.5); 2.496(17.7); 2.386(0.3); 1.777(1.2); 1.766(2.5); 1.753(2.5); 1.742(1.2); 1.194 (3.4); 1.181(7.8); 1.169(3.4); 0.977(4.2); 0.964(8.8); 0.952(4.0); 0.000(4.1) |
| 2.51 | 2.64 | Example 52: $^1$H-NMR(400.0 MHz, d$_6$-DMSO): □ = 10.974(2.9); 9.290(4.2); 8.515(12.7); 8.298(4.5); 4.179(10.4); 4.038(0.6); 4.021(0.6); 3.880(16.0); 3.674(1.0); 3.656(3.4); 3.637(3.5); 3.619(1.1); 3.590(1.6); 3.572(5.1); 3.555(5.1); 3.537(1.6); 3.325 (92.3); 3.319(72.8); 2.676(0.4); 2.671(0.6); 2.667(0.4); 2.524(1.3); 2.511(33.9); 2.506(68.6); 2.502(90.7); 2.497(66.9); 2.493(33.4); 2.333(0.4); 2.329(0.6); 2.324(0.4); 1.988(2.6); 1.398(0.9); 1.192(4.1); 1.178(6.6); 1.173(9.2); 1.161(11.1); 1.155(4.4); 1.143(5.1); 0.008(0.8); 0.000(23.1); −0.008(0.9) |
| 2.38 | 2.51 | Example 53: $^1$H-NMR(400.0 MHz, d$_6$-DMSO): □ = 11.408(3.0); 9.292(4.2); 8.538(0.6); 8.516(4.9); 8.510(5.0); 8.488(0.6); 8.302(4.4); 4.038(0.7); 4.020 (0.7); 3.879(13.8); 3.656(1.0); 3.638(3.1); 3.619(3.2); 3.601(1.0); 3.395(8.6); 3.325(79.3); 2.671 (0.4); 2.501(60.1); 2.327(0.4); 2.177(16.0); 1.988(2.7); 1.398(3.2); 1.189(3.5); 1.171(7.3); 1.152 (3.3); 0.000(11.0); −0.001(10.3) |
| 2.12 | 2.08 | Example 54: $^1$H-NMR(400.0 MHz, d$_6$-DMSO): □ = 11.839(2.8); 9.310(3.8); 9.160(2.4); 9.156(2.4); 8.795(1.8); 8.791(1.9); 8.783(1.9); 8.779(1.9); 8.684 (2.7); 8.662(4.4); 8.591(3.6); 8.568(2.4); 8.387(1.0); 8.382(1.3); 8.377(1.0); 8.367(1.1); 8.362 (1.4); 8.357(1.0); 8.313(4.2); 7.589(1.2); 7.576(1.2); 7.569(1.2); 7.557(1.1); 4.038(0.4); 4.021(0.3); 3.922(16.0); 3.711(0.9); 3.692(3.2); 3.674(3.2); 3.656(1.0); 3.386(0.4); 3.326(457.7); 3.302 (1.3); 3.285(0.6); 3.185(0.5); 2.676(0.9); 2.671(2.4); 2.666(0.9); 2.524(3.5); 2.511(73.1); 2.506(148.3); 2.502(194.7); 2.497(140.9); 2.493(67.9); 2.465(0.4); 2.455(0.3); 2.333(0.8); 2.329(1.2); 2.324 (0.8); 1.988(1.4); 1.216(3.6); 1.198(8.1); 1.180(3.4); 1.175(1.4); 1.157(0.4); 0.008(0.4); 0.000 (11.7) |
| | 1.39 | Example 55: $^1$H-NMR(400.0 MHz, d$_6$-DMSO): □ = 9.243(8.0); 8.974(2.9); 8.310(0.3); 8.244(7.4); 7.993(1.3); 7.973(1.4); 7.058(0.4); 7.042(0.4); 5.751 (1.8); 4.566(2.1); 4.363(0.8); 4.039(0.4); 4.021(0.4); 3.844(13.7); 3.522(1.5); 3.503(4.2); 3.485 (4.3); 3.467(1.6); 3.337(243.9); 3.333(189.2); 3.331(188.2); 2.672(0.7); 2.507(92.9); 2.503(117.9); 2.498(88.3); 2.329(0.7); 1.988(1.5); 1.235(0.4); 1.193(0.5); 1.175(1.0); 1.159(7.6); 1.141(16.0); 1.122(7.2); 0.008(0.8); 0.000(20.0) |
| 2.35 | 2.37 | Example 56: $^1$H-NMR(400.0 MHz, d$_6$-DMSO): □ = 9.236(4.9); 8.239(4.2); 8.002(0.7); 7.991(1.2); 7.978(0.7); 7.914(0.6); 7.892(0.6); 6.799(3.8); 6.777 (3.7); 4.057(0.8); 4.039(2.5); 4.021(2.5); 4.003(0.8); 3.854(16.0); 3.540(0.9); 3.522(2.8); 3.503 (2.9); 3.485(1.0); 3.358(182.8); 3.348(127.9); 3.319(2.6); 3.302(0.7); 3.284(0.7); 2.673(0.6); 2.527 (1.0); 2.522(1.5); 2.513(26.4); 2.509(56.2); 2.504(75.4); 2.500(53.6); 2.495(25.1); 2.335(0.3); 2.331(0.4); 1.989(11.2); 1.194(2.8); 1.176(5.7); 1.164(5.2); 1.158(5.5); 1.146(11.4); 1.127(5.4); 0.000(0.9) |
| | 1.81 | Example 57: $^1$H-NMR(400.0 MHz, d$_6$-DMSO): □ = 11.520(1.4); 11.473(1.5); 9.297(4.1); 8.545(0.8); 8.541(0.7); 8.523(3.0); 8.519(3.1); 8.507(4.0); 8.485(1.0); 8.308(4.3); 3.887(11.5); 3.665(0.6); 3.646(1.8); 3.633(2.0); 3.628(2.1); 3.615(1.8); 3.596 (0.5); 3.319(177.5); 3.258(0.5); 3.238(1.1); 3.213(0.9); 3.189(0.5); 3.177(0.6); 3.160(0.6); 3.143 (0.4); 3.092(0.6); 3.076(0.4); 3.060(0.8); 3.044(0.6); 2.929(0.7); 2.910(0.7); 2.897(0.6); 2.878 (0.4); 2.749(0.8); 2.727(0.7); 2.674(0.8); 2.670(1.0); 2.588(16.0); 2.505(135.9); 2.501(170.3); 2.497 (126.6); 2.332(0.8); 2.328(1.0); 1.301(4.4); 1.284(4.9); 1.187(2.8); 1.169(5.7); 1.150(2.7); 0.008 (2.6); 0.000(47.3) |
| 1.20 | 2.37 | Example 58: $^1$H-NMR(400.0 MHz, d$_6$-DMSO): □ = 9.247(3.8); 8.249(3.9); 8.247(4.0); 8.031(3.5); 8.009(3.8); 7.159(3.7); 7.137(3.6); 4.038(0.9); 4.020 (0.9); 3.869(16.0); 3.658(0.9); 3.640(3.2); 3.621(3.3); 3.603(0.9); 3.319(276.0); 2.675(0.8); 2.670 (1.1); 2.666(0.8); 2.661(0.4); 2.523(2.9); 2.510(65.8); 2.506(138.8); 2.501(186.8); 2.496(134.0); 2.492(63.4); 2.337(0.4); 2.332(0.8); 2.328(1.1); 2.323(0.8); 2.319(0.4); 1.988(4.0); 1.192(1.2); 1.185(3.4); 1.174(2.5); 1.167(7.7); 1.157(1.4); 1.148(3.3); 0.000(2.6) |
| 0.90 | 2.08 | Example 59: $^1$H-NMR(600.1 MHz, d$_6$-DMSO): □ = 11.621(1.2); 9.290(4.6); 8.413(3.0); 8.398(3.1); 8.291(5.0); 7.371(3.0); 7.357(3.0); 4.364(0.4); 3.923 (16.0); 3.904(2.1); 3.774(1.1); 3.762(3.6); 3.750(3.6); 3.738(1.2); 3.485(1.1); 3.473(3.5); 3.460 (3.6); 3.448(1.2); 3.325(2.6); 3.172(3.2); 2.504(27.5); 1.237(4.2); 1.225(8.6); 1.214(6.9); 1.202 (8.3); 1.190(3.9); 0.000(0.8) |
| 2.39 | 2.37 | Example 60: $^1$H-NMR(400.0 MHz, d$_6$-DMSO): □ = 9.250(5.1); 8.250(5.5); 8.030(3.0); 8.007(3.3); 7.388(2.3); 7.365(2.2); 5.757(2.2); 5.248(1.3); 5.233 (1.3); 3.870(16.0); 3.575(1.1); 3.556(3.6); 3.538(3.7); 3.519(1.3); 3.322(31.7); 3.296(0.5); 3.235 (15.8); 2.550(7.4); 2.536(7.5); 2.503(39.6); 1.236(0.3); 1.172(3.7); 1.154(8.0); 1.135(3.7); 0.000 (11.4) |
| | 2.02 | Example 61: $^1$H-NMR(400.0 MHz, d$_6$-DMSO): □ = 11.489(2.8); 9.297(4.4); 8.543(0.9); 8.521(5.6); 8.513(5.2); 8.491(0.9); 8.310(4.7); 4.056(0.7); 4.038 (2.1); 4.020(2.2); 4.003(0.7); 3.884(16.0); 3.648(1.0); 3.630(3.6); 3.611(3.5); 3.593(2.0); 3.569 (0.8); 3.320(269.6); 3.298(2.6); 3.279(0.8); 3.271(1.6); 3.260(0.9); 3.008(15.6); 2.675(0.7); 2.670 (1.0); 2.666(0.7); 2.523(2.3); 2.506(124.3); 2.501(164.0); 2.497(119.1); 2.333(0.7); 2.328(1.0); |

| logP-neutral | logP-acidic | |
|---|---|---|
| | | 2.324(0.7); 1.988(9.0); 1.284(5.8); 1.267(5.7); 1.192(2.6); 1.185(3.8); 1.175(5.3); 1.167(8.3); 1.157(2.8); 1.148(3.6); 0.000(8.3) |
| 2.47 | 2.54 | Example 62: $^1$H-NMR(400 MHz, d$_6$-DMSO): ☐ = 11.301(2.7); 9.315(4.0); 8.530(1.6); 8.508(5.1); 8.488(4.5); 8.466(1.5); 8.326(4.2); 8.324(4.3); 5.753 (0.6); 3.881(15.9); 3.669(0.9); 3.651(3.3); 3.632(3.3); 3.614(1.0); 3.316(68.8); 2.675(0.5); 2.671 (0.6); 2.666(0.5); 2.524(1.7); 2.510(34.5); 2.506(71.8); 2.501(96.1); 2.497(69.9); 2.492(33.9); 2.333(0.5); 2.328(0.6); 2.324(0.4); 2.285(0.5); 2.173(16.0); 1.234(0.5); 1.188(3.6); 1.169(8.2); 1.151(3.6); 0.008(2.1); 0.000(62.0); −0.008(2.4) |
| | 2.60 | Example 63: $^1$H-NMR(400.0 MHz, d$_6$-DMSO): ☐ = 12.689(2.0); 9.304(4.2); 8.602(1.7); 8.580(1.6); 8.312(4.7); 4.038(0.8); 4.020(0.8); 3.908(16.0); 3.711(1.0); 3.692(3.4); 3.674(3.5); 3.655(1.1); 3.354(108.5); 3.344(170.1); 3.336(128.4); 3.331 (129.7); 2.743(5.0); 2.675(0.8); 2.671(1.0); 2.667(0.8); 2.524(2.1); 2.506(128.7); 2.502(167.3); 2.498 (123.2); 2.329(0.9); 2.324(0.7); 1.988(3.4); 1.398(0.7); 1.236(0.6); 1.205(3.6); 1.187(8.2); 1.175 (2.4); 1.168(3.7); 1.157(1.0); 0.008(1.1); 0.000(35.9) |
| 2.49 | 2.55 | Example 64: $^1$H-NMR(400.0 MHz, d$_6$-DMSO): ☐ = 9.246(2.4); 8.247(2.1); 8.033(1.8); 8.010(1.9); 7.021(1.8); 6.998(1.7); 4.039(0.4); 4.021(0.4); 3.870 (8.4); 3.580(0.6); 3.562(1.8); 3.544(1.9); 3.525(0.6); 3.362(178.0); 3.351(136.0); 3.349(147.2); 3.158(16.0); 2.673(0.4); 2.527(0.8); 2.513(21.4); 2.509(45.6); 2.504(61.9); 2.500(45.6); 2.331 (0.4); 1.989(1.7); 1.194(0.4); 1.173(2.1); 1.155(4.1); 1.136(1.8); 0.000(0.5) |
| 2.78 | 2.94 | Example 65: $^1$H-NMR(400.0 MHz, d$_6$-DMSO): ☐ = 11.399(2.3); 9.292(3.3); 8.581(1.9); 8.558(3.4); 8.502(3.0); 8.480(1.8); 8.303(3.5); 4.039(0.8); 4.021 (0.8); 3.877(12.5); 3.634(0.7); 3.616(2.4); 3.597(2.4); 3.579(0.8); 3.324(48.4); 3.015(0.4); 2.999 (0.6); 2.979(0.7); 2.962(0.5); 2.810(0.9); 2.789(0.8); 2.777(1.2); 2.756(1.0); 2.713(0.3); 2.698 (0.3); 2.681(0.5); 2.583(0.4); 2.566(0.5); 2.557(1.1); 2.550(0.5); 2.542(1.2); 2.524(2.2); 2.510(18.4); 2.506(36.6); 2.502(47.9); 2.497(35.8); 2.493(18.5); 2.476(0.6); 2.072(16.0); 2.051(4.8); 1.988 (3.3); 1.398(1.0); 1.190(5.9); 1.184(3.9); 1.173(6.4); 1.165(6.9); 1.158(1.5); 1.147(2.9); 1.136(2.2); 1.119(2.1); 0.008(0.5); 0.000(11.5); −0.008(0.5) |
| 2.58 | 2.60 | Example 66: $^1$H-NMR(400.0 MHz, d$_6$-DMSO): ☐ = 10.761(3.0); 9.306(3.9); 9.297(4.4); 9.292(4.5); 8.761(4.5); 8.756(4.4); 8.659(2.4); 8.637(5.2); 8.601 (4.2); 8.579(2.0); 8.311(4.0); 8.309(4.1); 4.056(0.5); 4.038(1.7); 4.021(1.7); 4.003(0.6); 3.941 (16.0); 3.755(0.9); 3.737(3.2); 3.718(3.3); 3.700(1.0); 3.322(207.0); 2.675(0.4); 2.671(0.6); 2.666 (0.4); 2.524(1.4); 2.511(33.6); 2.506(69.9); 2.502(93.1); 2.497(68.1); 2.493(33.4); 2.333(0.4); 2.329(0.6); 2.324(0.4); 1.989(7.6); 1.235(0.7); 1.225(3.6); 1.207(8.1); 1.193(2.7); 1.188(3.6); 1.175 (4.0); 1.157(2.0); 0.000(6.8) |
| 2.14 | 2.14 | Example 67: $^1$H-NMR(400.0 MHz, d$_6$-DMSO): ☐ = 9.256(4.2); 8.267(4.5); 7.948(3.0); 7.926(3.2); 7.418(2.6); 6.772(3.3); 6.749(3.2); 3.828(16.0); 3.502 (1.0); 3.484(3.3); 3.465(3.4); 3.447(1.0); 3.316(40.1); 2.675(0.4); 2.670(0.5); 2.666(0.4); 2.523 (1.2); 2.510(28.4); 2.506(58.8); 2.501(79.0); 2.497(58.7); 2.492(29.6); 2.332(0.3); 2.328(0.5); 2.324(0.4); 2.073(1.3); 1.153(3.5); 1.134(8.0); 1.116(3.4); 0.146(0.3); 0.008(2.5); 0.000(70.1); −0.008 (2.9); −0.150(0.3) |
| 2.99 | 2.96 | Example 68: $^1$H-NMR(400.0 MHz, d$_6$-DMSO): ☐ = 12.293(0.3); 11.562(3.1); 9.297(4.6); 8.518(1.3); 8.495(5.1); 8.481(4.7); 8.459(1.3); 8.305(4.9); 7.360(0.9); 7.346(10.2); 7.340(5.7); 7.330(5.4); 7.310(2.6); 7.293(2.0); 7.281(0.9); 7.275(1.3); 7.262 (3.7); 7.244(2.1); 3.880(16.0); 3.799(8.9); 3.638(1.0); 3.619(3.4); 3.601(3.3); 3.582(1.1); 3.558 (5.0); 3.319(57.2); 2.671(0.6); 2.506(83.4); 2.502(107.6); 2.498(81.7); 2.329(0.6); 1.989(0.5); 1.398(1.6); 1.174(3.9); 1.156(8.2); 1.137(3.6); 0.008(1.5); 0.000(39.5) |
| 2.10 | 2.11 | Example 69: $^1$H-NMR(601.6 MHz, d$_6$-DMSO): ☐ = 9.285(3.4); 8.483(3.2); 8.468(3.7); 8.311(1.0); 8.292(3.7); 8.246(3.3); 8.232(2.9); 6.232(0.3); 3.916 (16.0); 3.755(1.0); 3.742(3.4); 3.730(3.3); 3.718(1.1); 3.455(16.6); 3.315(545.9); 2.619(0.6); 2.616 (1.2); 2.613(1.8); 2.610(1.4); 2.522(2.8); 2.519(3.3); 2.516(3.2); 2.507(87.5); 2.504(193.9); 2.501(272.8); 2.498(200.1); 2.495(95.3); 2.448(0.5); 2.446(0.5); 2.385(2.0); 2.382(1.4); 2.350(0.4); 2.342(15.7); 1.215(3.6); 1.202(7.9); 1.190(3.6); 0.097(0.4); 0.005(2.2); 0.000(90.8); −0.006 (3.9); −0.100(0.5) |
| 1.68 | 1.63 | Example 70: $^1$H-NMR(400.0 MHz, d$_6$-DMSO): ☐ = 11.622(2.6); 9.296(3.7); 8.534(8.8); 8.310(3.9); 4.136(1.9); 4.103(2.5); 3.933(2.6); 3.902(11.8); 3.884(14.4); 3.672(0.8); 3.653(2.9); 3.635(3.0); 3.616(0.9); 3.395(0.4); 3.322(224.0); 2.710(16.0); 2.675(0.5); 2.670(0.6); 2.666(0.5); 2.524(1.3); 2.510(35.5); 2.506(75.5); 2.501(102.4); 2.497(75.2); 2.492(37.1); 2.333(0.4); 2.328(0.6); 2.324(0.5); 2.176(0.7); 1.235(0.4); 1.190(3.3); 1.172(7.4); 1.153(3.2); 0.000(5.3) |
| 2.46 | 2.44 | Example 71: $^1$H-NMR(400.0 MHz, d$_6$-DMSO): ☐ = 9.277(2.6); 8.630(1.7); 8.607(2.2); 8.454(0.9); 8.431(0.7); 8.291(2.8); 4.056(0.4); 4.038(1.2); 4.020 (1.2); 4.003(0.4); 3.852(0.6); 3.833(2.1); 3.816(10.1); 3.796(0.7); 3.318(63.7); 2.671(0.4); 2.523 (1.1); 2.506(48.3); 2.501(67.7); 2.497(53.7); 2.361(16.0); 2.317(7.8); 1.989(5.2); 1.398(2.7); 1.243 (2.1); 1.225(4.7); 1.206(2.1); 1.192(1.4); 1.175(2.7); 1.157(1.3); 0.008(0.6); 0.000(17.2) |
| 1.92 | 1.87 | Example 72: $^1$H-NMR(400.0 MHz, d$_6$-DMSO): ☐ = 11.740(2.3); 9.300(5.0); 8.572(1.4); 8.551(4.2); 8.530(3.6); 8.508(1.3); 8.315(5.3); 4.487(7.1); 3.887 (16.0); 3.824(0.8); 3.677(1.1); 3.659(3.7); 3.641(3.8); 3.622(1.2); 3.411(0.3); 3.371(0.5); 3.320 (512.6); 3.288(0.9); 3.206(14.6); 2.671(2.4); 2.560(0.4); 2.505(329.6); 2.501(378.9); 2.433(0.4); 2.328(2.4); 1.193(3.9); 1.174(8.4); 1.156(3.9); 1.131(0.4); 0.147(0.4); 0.004(42.3); 0.001(81.9); 0.000(87.0); −0.026(0.4); −0.148(0.5) |
| 3.37 | 3.37 | Example 73: $^1$H-NMR(400.0 MHz, d$_6$-DMSO): ☐ = 11.683(3.2); 9.310(4.4); 8.669(2.7); 8.647(4.2); 8.572(3.7); 8.549(2.4); 8.313(5.0); 8.076(4.6); 8.055 (5.0); 7.951(3.8); 7.946(1.4); 7.929(4.1); 7.625(5.1); 7.603(4.5); 7.579(4.1); 7.557(3.5); 4.038 (0.4); 4.021(0.4); 3.919(16.0); 3.707(1.0); 3.689(3.4); 3.670(3.4); 3.652(1.1); 3.323(131.1); 2.671 (0.9); 2.506(116.8); 2.502(145.0); 2.498(105.3); 2.333(0.7); 2.329(0.9); 2.325(0.7); 1.989(1.6); 1.351(0.3); 1.213(3.7); 1.195(8.4); 1.176(4.2); 1.158(0.5); 0.008(1.8); 0.000(44.2); −0.008(2.1) |

| logP-neutral | logP-acidic | |
|---|---|---|
| 1.96 | | Example 74: $^1$H-NMR(400.0 MHz, d$_6$-DMSO): □ = 9.243(3.9); 8.247(4.2); 7.991(3.4); 7.968(3.7); 7.443(1.8); 7.420(1.7); 5.755(1.7); 5.054(5.3); 3.855 (16.0); 3.554(0.9); 3.536(3.1); 3.517(3.2); 3.499(1.0); 3.320(160.6); 3.293(15.6); 2.675(0.5); 2.670 (0.7); 2.666(0.5); 2.524(1.8); 2.519(2.7); 2.510(38.7); 2.506(82.9); 2.501(117.0); 2.497(87.9); 2.492(42.1); 2.333(0.5); 2.328(0.7); 2.323(0.5); 1.163(3.3); 1.145(7.6); 1.126(3.2); 0.008(1.3); 0.000(42.5); −0.009(1.5) |

Use Examples

*Phaedon cochleariae*-Spray Test
Solvent: 78.0 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: 1, 2, 3, 4, 6, 7, 8, 10, 13, 14, 15, 16, 21, 22, 24, 26, 27, 31, 32, 36, 37, 38, 40, 43, 46, 51, 52, 53, 54, 55, 56, 57, 60, 61, 62, 63, 64, 65, 66, 67, 68, 69, 70, 72, 74

In this test, for example, the following compounds from the preparation examples show an efficacy of 83% at an application rate of 500 g/ha: 9, 20

In this test, for example, the following compounds from the preparation examples show an efficacy of 100% at an application rate of 100 g/ha: 73

In this test, for example, the following compounds from the preparation examples show an efficacy of 83% at an application rate of 100 g/ha: 33

*Spodoptera frugiperda*-Spray Test
Solvent: 78.0 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Leaf disks of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compounds from the preparation examples show an efficacy of 100% at an application rate of 500 g/ha: 21, 40, 62, 64, 67

In this test, for example, the following compounds from the preparation examples show an efficacy of 83% at an application rate of 500 g/ha: 10

*Myzus persicae* Spray Test
Solvent: 78 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that no aphids have been killed.

In this test, for example, the following compounds from the preparation examples show an efficacy of 100% at an application rate of 500 g/ha: 3, 4, 16, 24, 31, 52, 55, 56, 61, 65, 70, 72

In this test, for example, the following compounds from the preparation examples show an efficacy of 90% at an application rate of 500 g/ha: 2, 7, 8, 9, 10, 13, 14, 20, 21, 34, 36, 37, 38, 43, 44, 53, 57, 63, 64, 67, 69, 74

In this test, for example, the following compounds from the preparation examples show an efficacy of 100% at an application rate of 100 g/ha: 59

In this test, for example, the following compounds from the preparation examples show an efficacy of 90% at an application rate of 100 g/ha: 60, 66

*Tetranychus urticae*-Spray Test, OP-Resistant
Solvent: 78.0 parts by weight of acetone
  1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 500 g/ha: 31, 34, 67

In this test, for example, the following compounds from the preparation examples show an efficacy of 90% at an application rate of 500 g/ha: 24, 33, 56, 58, 62, 74

In this test, for example, the following compounds from the preparation examples shows an efficacy of 90% at an application rate of 100 g/ha: 60

*Meloidogyne incognita*-Test
Solvent: 125.0 parts by weight of acetone

To produce a suitable preparation of active compound, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples shows an efficacy of 100% at an application rate of 20 ppm: 56, 65

In this test, for example, the following compounds from the preparation examples shows an efficacy of 90% at an application rate of 20 ppm: 11, 14, 18, 29, 62

*Boophilus microplus*-Injection Test
Solvent: dimethyl sulphoxide

To produce a suitable preparation of active compound, 10 mg of active compound are mixed with 0.5 ml of solvent and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 80% at an application rate of 20 µg/animal: 14, 22

*Ctenocephalides felis*-Oral Test
Solvent: dimethyl sulphoxide

To produce a suitable preparation of active compound, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: 8, 14, 22

*Lucilia cuprina* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: 8, 10, 14 In this test, for example, the following compounds from the preparation examples show an efficacy of 90% at an application rate of 100 ppm: 22

*Musca domestica* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: 8, 22

In this test, for example, the following compounds from the preparation examples show an efficacy of 90% at an application rate of 100 ppm: 10

*Myzus persicae* Spray Test
Solvent: 7 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bell pepper plants (*Capsicum annuum*) severely infested with the green peach aphid (*Myzus persicae*) are treated by spraying with the active compound preparation in the desired concentration.

After 6 days, the kill in % is determined. 100% means that all of the aphids have been killed; 0% means that none of the aphids have been killed.

In this test, for example, the following compounds from the preparation examples shows an efficacy of 100% at an application rate of 100 ppm: 22, 40

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 μl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm², given homogeneous distribution, an area-based dose of 5 μg/cm² is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 μg/cm². 100% efficacy means that all the fleas were dead or moribund. 0% efficacy means that no fleas were harmed.

In this test, for example, the following compounds from the preparation examples show an efficacy of 100% at an application rate of 5 μg/cm² (500 g/ha): 22

*Anopheles* Test (ANPHGB Surface Treatment)
Solvent: acetone+2000 ppm rapeseed oil methyl ester (RME)

To produce an appropriate active compound formulation, the active compound is dissolved in the solvent (2 mg/ml). The active compound formulation is pipetted onto a glazed tile and, after it has dried off, adult mosquitoes of the species *Anopheles gambiae* strain RSPH (homozygot kdr) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m²: 14

In this test, for example, the following compounds from the preparation examples show efficacy of 80-100% at an application rate of 20 mg/m²: 14

*Anopheles* Test (ANPHFU Surface Treatment)
Solvent: acetone+2000 ppm rapeseed oil methyl ester (RME)

To produce an appropriate active compound formulation, the active compound is dissolved in the solvent (2 mg/ml). The active compound formulation is pipetted onto a glazed tile and, after it has dried off, adult mosquitoes of the species *Anopheles funestus* strain FUMOZ-R (Hunt et al., Med Vet Entomol. 2005 September; 19(3):271-5) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m²: 14

In this test, for example, the following compounds from the preparation examples show efficacy of 80-100% at an application rate of 20 mg/m²: 14

*Aedes* Test (AEDSAE Surface Treatment)
Solvent: acetone+2000 ppm rapeseed oil methyl ester (RME)

To produce an appropriate active compound formulation, the active compound is dissolved in the solvent (2 mg/ml). The active compound formulation is pipetted onto a glazed tile and, after it has dried off, adult mosquitoes of the species *Aedes aegypti* strain MONHEIM are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m²: 14

In this test, for example, the following compounds from the preparation examples show efficacy of 80-100% at an application rate of 20 mg/m²: 14

The invention claimed is:

1. A compound of formula (I)

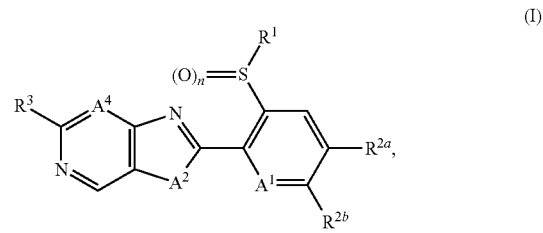

wherein
$A^1$ represents nitrogen,
$A^2$ represents N—$R^5$,
$A^4$ represents C—H,
$R^1$ represents methyl, ethyl, n-propyl, isopropyl, n-butyl, isobutyl or tert-butyl,
$R^{2a}$ represents hydrogen,
$R^{2b}$ represents a group selected from
—C(=O)—$R^8$ (Q1), where $R^8$ represents methoxy or ethoxy,
—C(=O)—$NR^{11}R^{12}$ (Q3), where $R^{11}$ represents hydrogen or methyl and $R^{12}$ represents hydrogen, methyl, ethyl, n-propyl, isopropyl, n-butyl, isobutyl, tert-butyl or cyclopropyl,
—C(=S)—$NR^{11}R^{12}$ (Q4), where $R^{11}$ represents hydrogen or methyl and $R^{12}$ represents methyl, ethyl, n-propyl, isopropyl, n-butyl, isobutyl, tert-butyl or cyclopropyl,
—S(O)$_m$—$R^{13}$ (Q5), where m represents 0, 1 or 2 and $R^{13}$ represents methyl, ethyl, n-propyl, isopropyl, n-butyl, isobutyl, tert-butyl, phenyl or benzyl,
—S=O(=NH)—$R^{13}$ (Q6), where $R^{13}$ represents methyl, ethyl, n-propyl, isopropyl, n-butyl, isobutyl or tert-butyl,
—S(=N—CN)—$R^{13}$ (Q8), where $R^{13}$ represents methyl, ethyl, n-propyl, isopropyl, n-butyl, isobutyl or tert-butyl,
—S(O)$_2$—$NR^{11}R^{12}$ (Q9), where $R^{11}$ represents hydrogen, methyl, ethyl, n-propyl, isopropyl or cyclopropyl and $R^{12}$ represents hydrogen, methyl, ethyl, n-propyl, isopropyl, n-butyl, isobutyl, tert-butyl or cyclopropyl,
—$NR^{11}R^{12}$ (Q10), where $R^{11}$ represents hydrogen, methyl, ethyl, n-propyl, isopropyl or cyclopropyl and R$^{12}$ represents hydrogen, methyl, ethyl, n-propyl, isopropyl, n-butyl, isobutyl, tert-butyl or cyclopropyl, —NR$^{11}$—NR$^{11}$R$^{12}$ (Q11), where R$^{11}$ represents hydrogen, methyl, ethyl, n-propyl, isopropyl, cyclopropyl or COmethyl (acetyl) and R$^{12}$ represents hydrogen, methyl, ethyl, n-propyl, isopropyl, n-butyl, isobutyl, tert-butyl, cyclopropyl or COmethyl (acetyl), —NR$^{11}$—C(=O)—R$^{8}$ (Q12), where R$^{11}$ represents hydrogen or methyl and R$^{8}$ represents methyl, ethyl, n-propyl, isopropyl (where R$^{8}$ represents methyl, ethyl, n-propyl, or isopropyl only if R$^{11}$ does not represent hydrogen), trifluoromethyl, CHF$_2$, CF$_2$CF$_3$, CF$_2$CHF$_2$, CH$_2$OCH$_3$, CH$_2$SCH$_3$, CH$_2$OC$_2$H$_5$, CH$_2$SOCH$_3$, CH$_2$SO$_2$CH$_3$, CH(CH$_3$)CH$_2$SCH$_3$, CH(CH$_3$)CH$_2$SOCH$_3$, CH(CH$_3$)CH$_2$SO$_2$CH$_3$, C$_2$H$_4$OC$_2$H$_5$, C$_2$H$_4$S C$_2$H$_5$, C$_2$H$_4$OC$_2$H$_5$, C$_2$H$_4$SOC$_2$H$_5$, C$_2$H$_4$SO$_2$C$_2$H$_5$, CH(CH$_3$)CH$_2$SC$_2$H$_5$, CH(CH$_3$)CH$_2$SOC$_2$H$_5$, CH(CH$_3$)CH$_2$SO$_2$C$_2$H$_5$, cyclopropyl, cyclopropylmethyl (—CH$_2$-cyclopropyl), phenyl, benzyl,

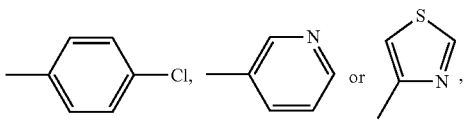

NR$^{11}$—C(=S)—R$^{8}$ (Q13), where R$^{8}$ represents methyl, ethyl, n-propyl, isopropyl, n-butyl, isobutyl, tert-butyl or cyclopropyl and R$^{11}$ represents hydrogen, methyl, ethyl, n-propyl, isopropyl or cyclopropyl, —NR$^{11}$—S(O)$_2$—R$^{13}$ (Q14), where R$^{11}$ represents hydrogen, methyl, ethyl, n-propyl, isopropyl, methylsulphonyl or cyclopropyl and R$^{13}$ represents methyl, ethyl, n-propyl, isopropyl, n-butyl, isobutyl, tert-butyl, cyclopropyl or trifluoromethyl, and —O—R$^{13}$ (Q17), where R$^{13}$ represents trifluoromethyl-1H-pyrazol-5-yl

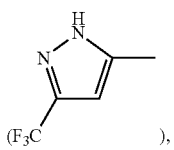

with the proviso that if R$^{2b}$ represents Q5, Q6, Q8 or Q9, then n represents 2, R$^{3}$ represents fluoromethyl, difluoromethyl, trifluoromethyl, fluoroethyl, difluoroethyl, trifluoroethyl, tetrafluoroethyl or pentafluoroethyl, R$^{5}$ represents methyl, ethyl or isopropyl, and n is 0, 1 or 2.

2. The compound of formula (I) according to claim 1 wherein

A$^{1}$ represents nitrogen,

A$^{2}$ represents N—R$^{5}$,

A$^{4}$ represents C—H,

R$^{1}$ represents ethyl,

R$^{2a}$ represents hydrogen,

R$^{2b}$ represents a group selected from

Q1, where R$^{8}$ represents methoxy,

Q3, where R$^{11}$ represents hydrogen and R$^{12}$ represents hydrogen, methyl, ethyl or cyclopropyl, Q4, where R$^{11}$ represents hydrogen and R$^{12}$ represents methyl, ethyl or cyclopropyl, Q5, where m represents 0, 1 or 2 and R$^{13}$ represents methyl, ethyl, isopropyl, phenyl or benzyl, Q6, where R$^{13}$ represents ethyl, Q8, where R$^{13}$ represents methyl, Q9, where R$^{11}$ represents hydrogen or methyl and R$^{12}$ represents methyl, ethyl or isopropyl, Q10, where R$^{11}$ represents hydrogen or methyl and R$^{12}$ represents hydrogen, methyl or ethyl, Q11, where R$^{11}$ represents hydrogen, methyl or COmethyl (acetyl) and R$^{12}$ represents hydrogen, methyl or COmethyl (acetyl), Q12, where R$^{11}$ represents hydrogen or methyl and R$^{8}$ represents methyl (only if R$^{11}$ does not represent hydrogen), trifluoromethyl, CHF$_2$, CF$_2$CF$_3$, CF$_2$CHF$_2$, CH$_2$OCH$_3$, CH$_2$SCH$_3$, CH$_2$OC$_2$H$_5$, CH$_2$SOCH$_3$, CH$_2$SO$_2$CH$_3$, CH(CH$_3$)CH$_2$SCH$_3$, CH(CH$_3$)CH$_2$SOCH$_3$, CH(CH$_3$)CH$_2$SO$_2$CH$_3$, cyclopropyl, cyclopropylmethyl (—CH$_2$-cyclopropyl), phenyl, benzyl,

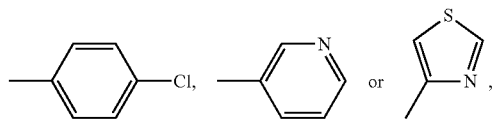

Q13, where R$^{8}$ represents methyl and R$^{11}$ represents hydrogen,

Q14, where R$^{11}$ represents hydrogen or methylsulphonyl and R$^{13}$ represents methyl, ethyl or trifluoromethyl, and Q17, where R$^{13}$ represents trifluoromethyl-1H-pyrazol-5-yl

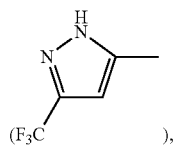

with the proviso that if R$^{2b}$ represents Q5, Q6, Q8 or Q9, then n represents 2, R$^{3}$ represents trifluoromethyl or pentafluoroethyl, R$^{5}$ represents methyl, and n is 0, 1 or 2.

3. The compound of formula (I) according to claim 1 wherein

A$^{1}$ represents nitrogen,

A$^{2}$ represents N—R$^{5}$,

A$^{4}$ represents C—H,

R$^{1}$ represents methyl, ethyl, n-propyl, isopropyl, n-butyl, isobutyl or tert-butyl, R$^{2a}$ represents hydrogen, R$^{2b}$ represents a group selected from the group consisting of

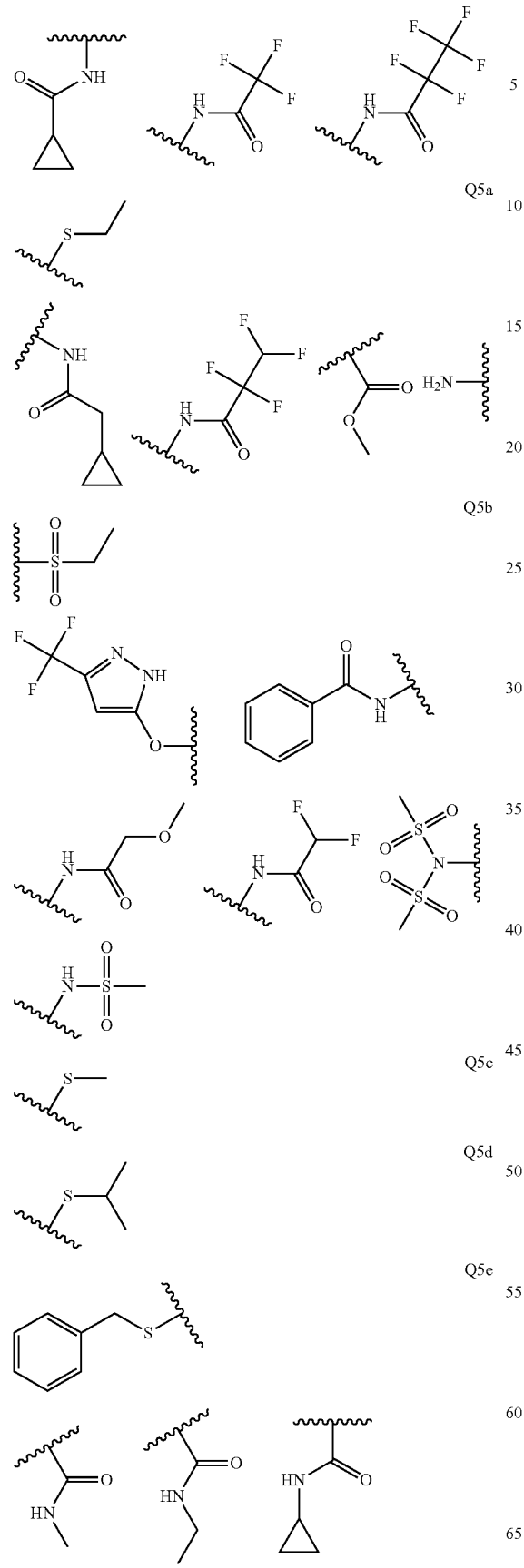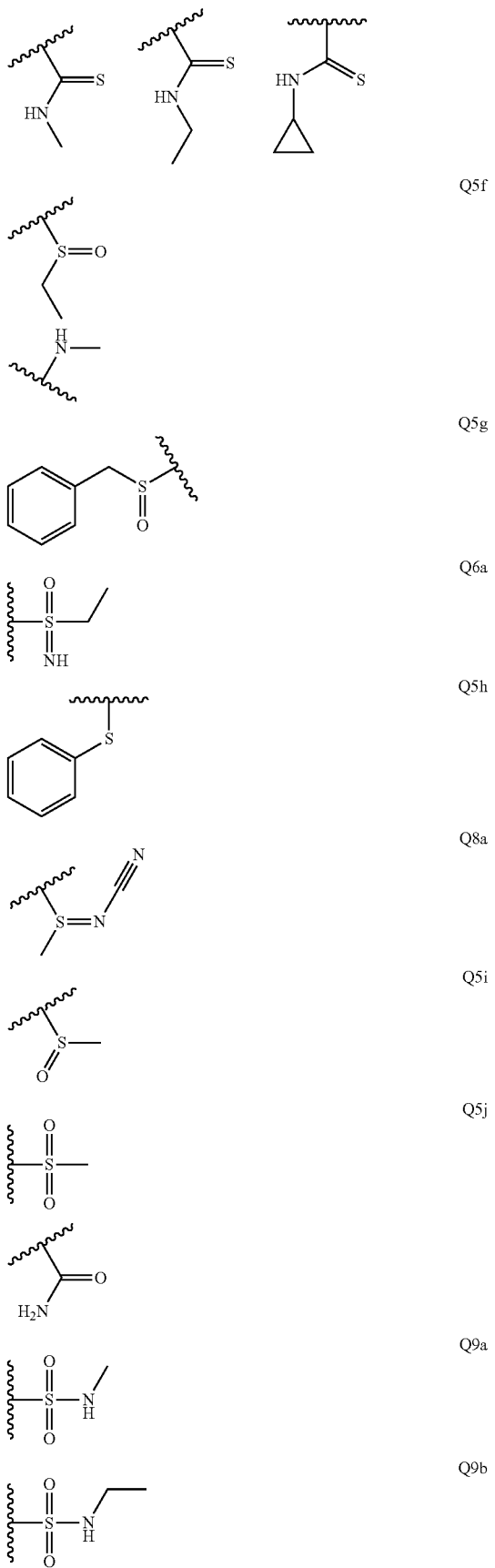

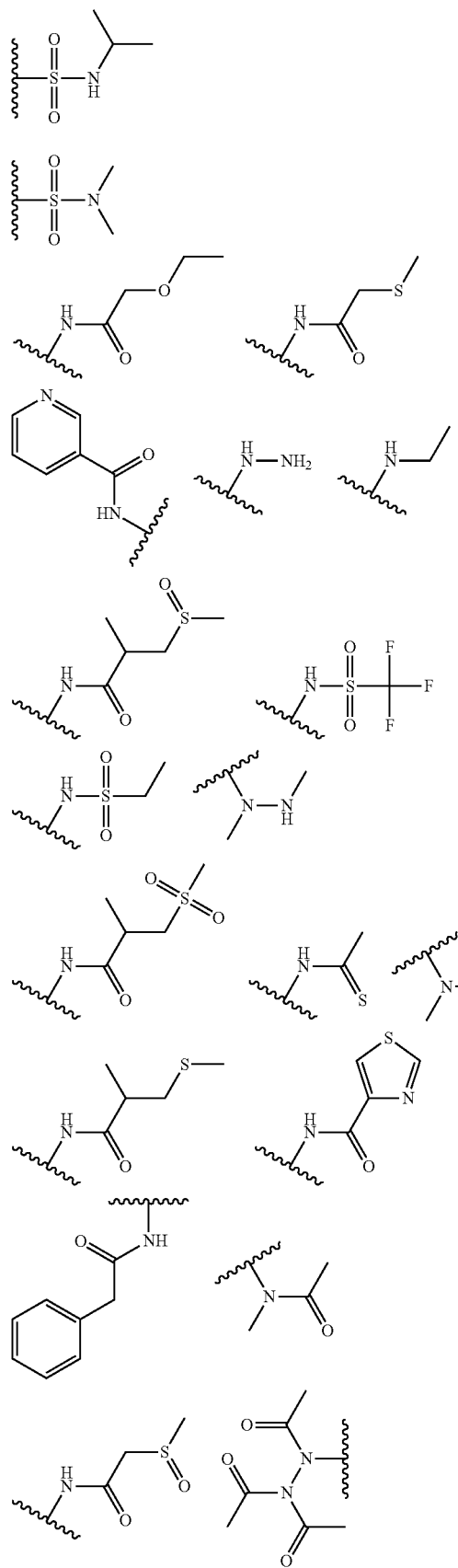

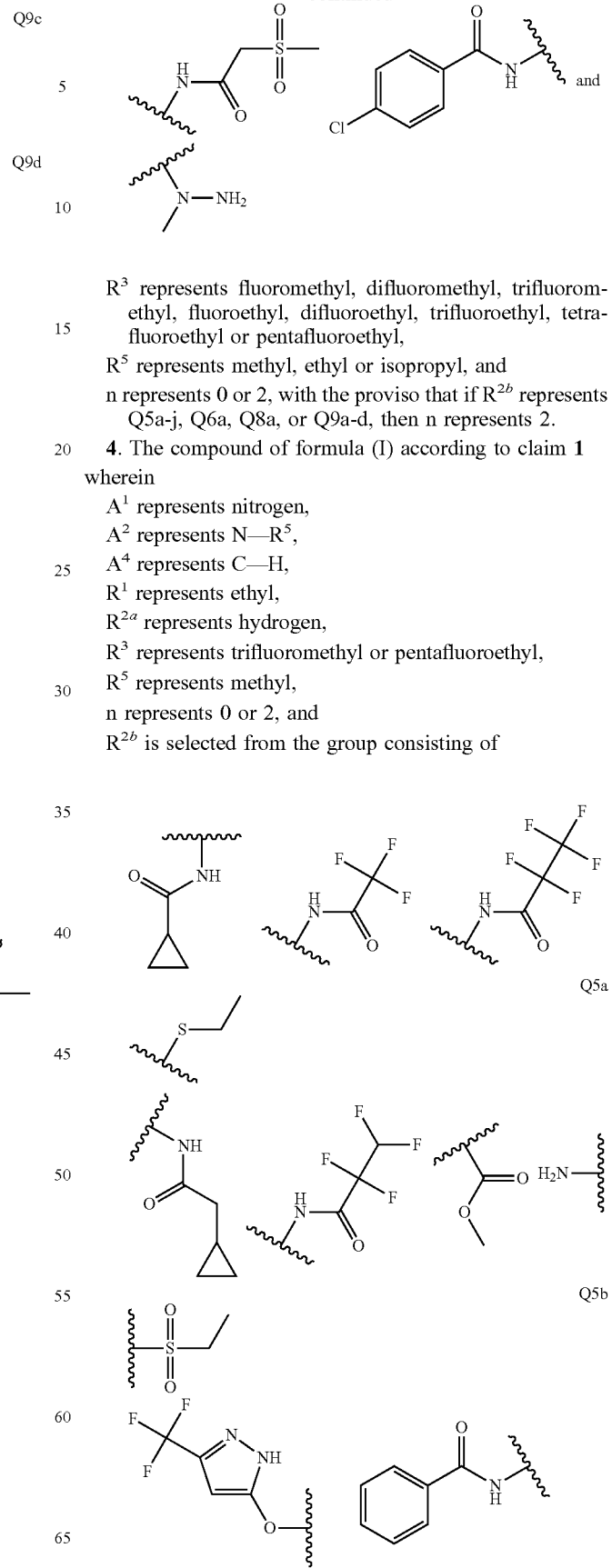

R[3] represents fluoromethyl, difluoromethyl, trifluoromethyl, fluoroethyl, difluoroethyl, trifluoroethyl, tetrafluoroethyl or pentafluoroethyl, R[5] represents methyl, ethyl or isopropyl, and n represents 0 or 2, with the proviso that if R[2b] represents Q5a-j, Q6a, Q8a, or Q9a-d, then n represents 2.

4. The compound of formula (I) according to claim 1 wherein

A[1] represents nitrogen,

A[2] represents N—R[5],

A[4] represents C—H,

R[1] represents ethyl,

R[2a] represents hydrogen,

R[3] represents trifluoromethyl or pentafluoroethyl,

R[5] represents methyl, n represents 0 or 2, and

R[2b] is selected from the group consisting of

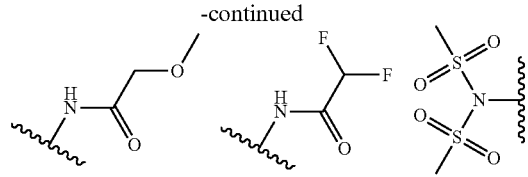
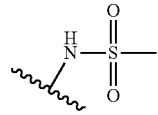
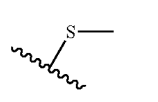
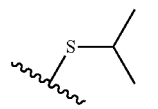
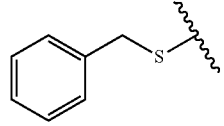
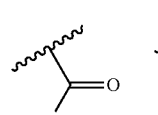
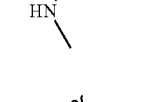
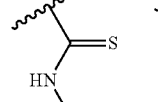
Q5c
Q5d
Q5e
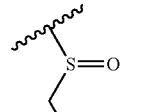
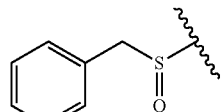
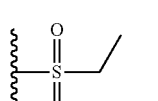
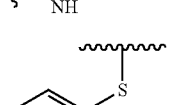
Q5f
Q5g
Q5h
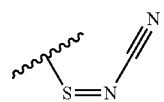
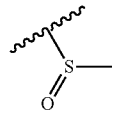
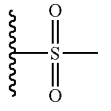
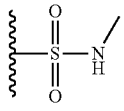
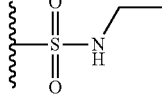
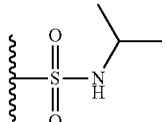
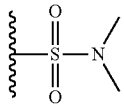
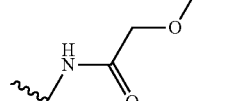
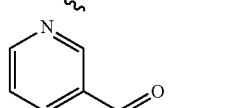
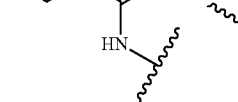
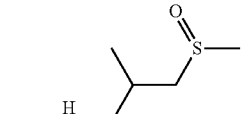
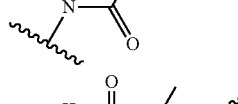
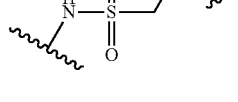
Q8a
Q5i
Q5j
Q9a
Q9b
Q9c
Q9d

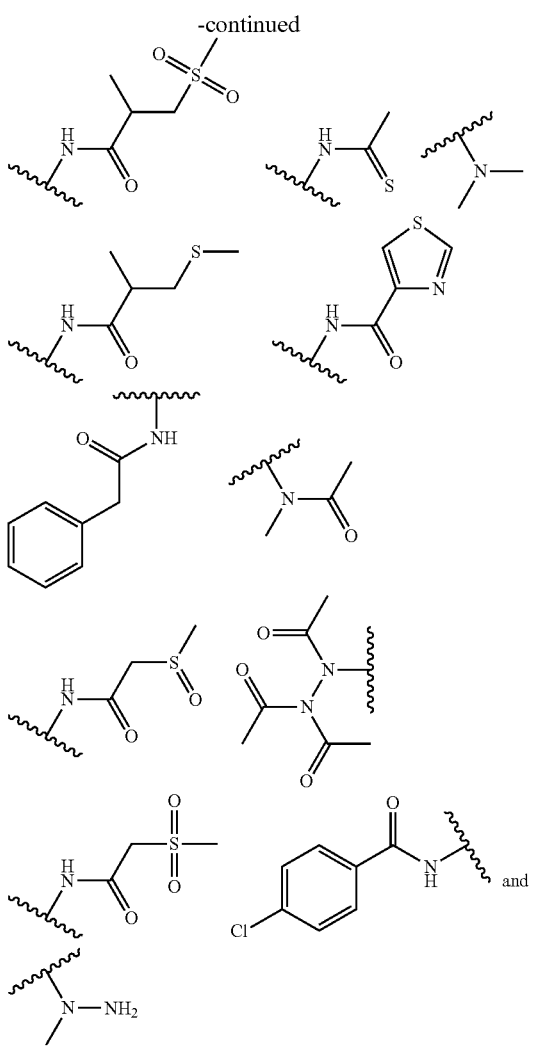

with the proviso that if $R^{2b}$ represents Q5a-j, Q6a, Q8a or Q9a-d, then n represents 2.

5. The compound of formula (I) according to claim 1 wherein $R^1$, $R^{2a}$, $R^{2b}$, $R^3$, $A^1$, $A^2$, $A^4$ and n have the meanings given in the table:

| $R^1$ | n | $A^4$ | $A^2$ | $A^1$ | $R^{2a}$ | $R^3$ | $R^{2b}$ |
|---|---|---|---|---|---|---|---|
| ethyl | 2 | CH | N-methyl | N | H | CF$_3$ | 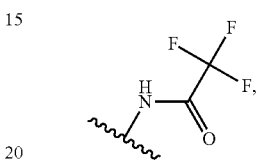 |
| ethyl | 2 | CH | N-methyl | N | H | CF$_3$ | 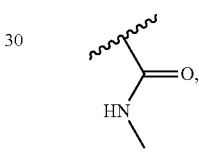 |

6. An agrochemical formulation comprising one or more compounds of formula (I) according to claim 1 and one or more extenders and/or surfactants.

7. The agrochemical formulation according to claim 6, additionally comprising a further agrochemically active compound.

8. A method for controlling one or more animal pests, comprising allowing a compound of formula (I) according to claim 1 or an agrochemical formulation thereof to act on the animal pests and/or a habitat thereof.

9. A product comprising one or more compounds of formula (I) according to claim 1 or one or more agrochemical formulations thereof for controlling animal pests.

10. The compound of formula (I) according to claim 1, wherein
$R^{2b}$ represents

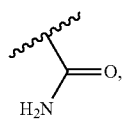

$R^3$ represents trifluoromethyl, and
n is 2.

11. The compound of formula (I) according to claim 1, wherein
$R^{2b}$ represents

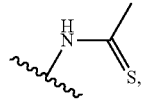

$R^3$ represents trifluoromethyl, and
n is 2.

12. The compound of formula (I) according to claim 1, wherein
$R^{2b}$ represents $R^3$ represents trifluoromethyl, and
n is 2.

13. The compound of formula (I) according to claim 1, wherein
$R^{2b}$ represents $R^3$ represents trifluoromethyl, and
n is 2.

* * * * *